United States Patent
Bilgicer et al.

(10) Patent No.: US 11,116,848 B2
(45) Date of Patent: Sep. 14, 2021

(54) SELECTIVE UV CROSSLINKING OF PEPTIDES AND FUNCTIONAL MOIETIES TO IMMUNOGLOBULINS

(71) Applicant: University of Notre Dame du Lac, South Bend, IN (US)

(72) Inventors: Zihni Basar Bilgicer, Granger, IN (US); Nathan J. Alves, South Bend, IN (US)

(73) Assignee: University of Notre Dame du Lac, South Bend, IN (US)

( * ) Notice: Subject to any disclaimer, the term of this patent is extended or adjusted under 35 U.S.C. 154(b) by 0 days.

(21) Appl. No.: 16/450,615

(22) Filed: Jun. 24, 2019

(65) Prior Publication Data
US 2019/0328896 A1  Oct. 31, 2019

Related U.S. Application Data

(62) Division of application No. 14/775,323, filed as application No. PCT/US2014/027788 on Mar. 14, 2014, now abandoned.
(Continued)

(51) Int. Cl.
*C07K 16/46* (2006.01)
*G01N 33/543* (2006.01)
*A61K 47/68* (2017.01)
*C07K 16/28* (2006.01)
*C07K 16/00* (2006.01)
(Continued)

(52) U.S. Cl.
CPC ........ *A61K 47/6889* (2017.08); *A61K 31/337* (2013.01); *A61K 47/6803* (2017.08); *C07K 16/00* (2013.01); *C07K 16/2887* (2013.01); *G01N 33/531* (2013.01);
(Continued)

(58) Field of Classification Search
CPC ............ A61K 47/6889; A61K 47/6803; A61K 31/337; C07K 16/46; C07K 16/2887; G01N 33/531; G01N 33/532; G01N 33/533
See application file for complete search history.

(56) References Cited

U.S. PATENT DOCUMENTS 5,596,081 A   1/1997  Haley et al.
5,693,764 A  12/1997  Haley et al.
(Continued)

OTHER PUBLICATIONS

Alves, Nathan J., et al., "Oriented antibody immobilization by site-specific UV photocrosslinking of biotin at the conserved nucleotide binding site for enhanced antigen detection," Biosensors and Bioelectronics, 2013, 387-397, 49.
(Continued)

*Primary Examiner* — Tracy Vivlemore
*Assistant Examiner* — Nam P Nguyen
(74) *Attorney, Agent, or Firm* — Haukaas Fortius PLLC; Michael H. Haukaas

(57) ABSTRACT

A method of crosslinking a hetero-bifunctional photo cross-linking compound to an immunoglobulin having at least one heterocyclic photo reactive group and at least one non-photo reactive group where the non-photo reactive group is coupled to an effector molecule and the photo reactive group is coupled to the nucleotide binding site of an immunoglobulin. Alternatively, the photo crosslinker contains an orthogonal reactive group such as a thiol, which can be coupled to an effector molecule or functionalized ligand.

19 Claims, 35 Drawing Sheets

Related U.S. Application Data

(60) Provisional application No. 61/851,962, filed on Mar. 14, 2013.

(51) Int. Cl.
  *G01N 33/531* (2006.01)
  *A61K 31/337* (2006.01)
  *G01N 33/532* (2006.01)
  *G01N 33/533* (2006.01)

(52) U.S. Cl.
  CPC ......... *G01N 33/532* (2013.01); *G01N 33/533* (2013.01); *G01N 33/54353* (2013.01)

(56) References Cited

U.S. PATENT DOCUMENTS

| | | | |
|---|---|---|---|
| 5,800,991 | A | 9/1998 | Haley et al. |
| 6,207,195 | B1 | 3/2001 | Walsh et al. |
| 6,238,667 | B1 | 5/2001 | Kohler |
| 9,598,460 | B2 | 3/2017 | Bilgicer et al. |
| 2006/0094039 | A1* | 5/2006 | Rosenfeld ............ G01N 33/689 435/6.12 |
| 2017/0166607 | A1 | 6/2017 | Bilgicer et al. |

OTHER PUBLICATIONS

Alves, Nathan J., et al., "Oriented Surface Immobilization of Antibodies at the Conserved Nucleotide Binding Site for Enhanced Antigen Detection," Langmiur, 2012, 9640-9648, 28.

Alves, Nathan J., et al., "Selective photocrosslinking of functional ligands to antibodiesvia the conserved nucleotide binding site," Biomaterials, 2013, 5700-5710, 34.

Extended Search Report of the European Patent Office dated Jan. 30, 2017 in EP Application No. 14768752.9; 10pgs.

Handlogten et al., "Design of a Heterobivalent Ligand to Inhibit IgE Clustering on Mast Cells," Chem Biol, 18 (9):1179-1188, Sep. 2011.

International Search Report and Written Opinion of the ISA/US dated Aug. 28, 2014 in International Application No. PCT/US2014/020910; 14pgs.

Partial Search Report of the European Patent Office dated Oct. 14, 2016 in EP Application No. 14768752.9; 6pgs.

Pavlinkova, Gabriela, et al., "Site-Specific Photobiotinylation of Immunoglobulins, Fragments and Light Chain Dimers," J. Immunol. Methods; 201:77-78; Feb. 14, 1997.

Rajagopalan, Krishnan, et al., "Novel Unconventional Binding Site in the Variable Region of Immunoglobulins," Proc. Natl. Acad. Sci. USA; 93(12):6019-6024; Jun. 11, 1996.

Russ et al., "Photo-activated Affinity-site Cross-linking of Antibodies Using Tryptophan Containing Peptides," J Immunol Methods, 304(1-2):100-106, Sep. 2005.

Song, Fayi, et al., "Principles of conjugating quantum dots to proteins via carbodiimide chemistry," Nanotechnology, 2011, 8 pages, 22.

Zimmermann, Julia L., et al., "Thiol-based, site-specific and covalent immobilization of biomolecules for single-molecule experiments," Nature Protocols, 2010, 978-985, 5.

Pattison et al., "Photo-oxidation of Proteins," Photochem Photobiol Sci., 11(1):38-53, Jan. 2012.

* cited by examiner

1. IBA-Thiol in PBS pH 6.8
2. 254 nm UV

R = Biotin, Fluorescence, Peptide, Drug...

SELECTIVE UV CROSSLINKING OF PEPTIDES AND FUNCTIONAL MOIETIES TO IMMUNOGLOBULINS

RELATED APPLICATIONS

This application is a divisional of U.S. patent application Ser. No. 14/775,323 filed Sep. 11, 2015, which is a National Stage filing under 35 U.S.C. § 371 of International Application No. PCT/US2014/027788 filed Mar. 14, 2014, which claims priority under 35 U.S.C. § 119(e) to U.S. Provisional Patent Application No. 61/851,962 filed Mar. 14, 2013, which applications are incorporated herein by reference in their entirety.

GOVERNMENT SUPPORT

This invention was made with government support under CBET-1263713 awarded by the National Science Foundation. The government has certain rights in the invention.

BACKGROUND OF THE INVENTION

Immunoglobulins are secreted by plasma cells and are used by the immune system to identify and neutralize objects foreign to the host. The immunoglobulin recognizes a unique part of the foreign object known as an antigen. Due to their exceptional specificity and nearly limitless diversity, immunoglobulins are extensively used in an array of diagnostic and therapeutic applications. When utilizing immunoglobulins, it is often necessary to conjugate them with various functional ligands to make them amenable for the specific application. For example, when immunoglobulins are implemented in diagnostic assays, they are commonly conjugated to reporters such as affinity tags, fluorescent probes, and enzymes to enhance antigen detection efficiency and sensitivity. Similarly, in therapeutic applications, pharmaceutical immunoglobulins are conjugated with peptides or cytotoxic drugs to achieve enhanced tumor targeting, tissue penetration, and improved therapeutic index. For the success of any application, functionalizing the immunoglobulins with high conjugation efficiency, while preserving its activity, is critical.

Currently, the standard method for functionalizing immunoglobulins involves the non-specific chemical ligation to lysine side chains (Lys-$\epsilon$-$NH_3^+$) that are scattered across the entire immunoglobulin surface. Coupling to lysine side chains can be accomplished using a number of amine specific chemistries, among which N-hydroxysuccinimide (NHS) ester coupling being the most commonly used. However, it is not possible to control the number and sites of conjugation with this method, which results in a heterogeneous immunoglobulin population. This method, due to its lack of specificity, can reduce immunoglobulin activity as a result of conjugations at the complementarity determining region (CDR, i.e., the region located at the end of the immunoglobulin Fab domain implicated in selective binding to the antigen). Furthermore, conjugations at the Fc domain can prevent binding of secondary immunoglobulins used for quantification in diagnostic assays and can also inhibit immunoglobulin-dependent cellular cytotoxicity (ADCC) when the immunoglobulin is used as a pharmaceutical agent. Therefore, non-site-specific conjugation methods often have a negative impact on the outcome of immunoglobulin-based detection assays by decreasing sensitivity and reproducibility. For these reasons, immunoglobulin-based assays would benefit greatly from a site-specific immunoglobulin functionalization method that maintains immunoglobulin activity without impacting antigen binding or Fc recognition.

Several site-specific covalent conjugation methods have been developed in an attempt to preserve immunoglobulin activity, including partial reduction of disulfides for sulfur chemistry and targeting immunoglobulin glycosylation sites for carbohydrate chemistry. However, these methods often require complicated chemical procedures with variable outcomes, and also risk denaturing the immunoglobulin and reducing its activity due to exposure to chemically harsh reaction conditions. In addition, the complexity of these methods results in a high overall cost for preparation of immunoglobulin conjugates. Taken together, these highlight the need for the development of a practical and reproducible method for site-specific conjugation of functional ligands to immunoglobulins.

Accordingly, there is a need for a method of functionalizing immunoglobulins that is simple, gentle to the immunoglobulin and cost effective. Here, the Applicants describe a method for site-specific conjugation of functional moieties to immunoglobulins at the nucleotide binding site (NBS) while preserving antigen binding activity without impeding Fc mediated interactions.

SUMMARY

The invention provides for a method of site specific photo crosslinking an immunoglobulin comprising the steps of:

a) providing an immunoglobulin or a fragment thereof with a conserved nucleotide binding site that is located away from the antigen binding site of the $F_V$ domain of the immunoglobulin or fragment; and b) providing a hetero-bifunctional photo-reactive crosslinker where the hetero-bifunctional photo-reactive crosslinker has at least one photo reactive heterocyclic functional group that interacts with the conserved nucleotide binding site of the immunoglobulin or fragment, and at least one non-photo reactive functional group; and c) mixing the immunoglobulin or fragment with the hetero-bifunctional photo-reactive crosslinker to provide a mixture; and d) exposing the mixture to ultra-violet light so that the at least one photo reactive functional group of the hetero-bifunctional photo-reactive crosslinker is covalently coupled within the nucleotide binding site of the immunoglobulin or fragment. As described herein below, reference to an immunoglobulin with a conserved nucleotide binding site can include a fragment of an immunoglobulin with a conserved nucleotide binding site.

In a preferred embodiment, the at least one heterocyclic functional group is an indole compound.

In a preferred embodiment, the heterocyclic functional group is indole-3-butyric acid.

In a preferred embodiment, the at least one non-photo reactive functional group is coupled to a surface in an orientation specific manner whereby the antigen binding sites are oriented away from the surface and available for antigen binding such that the immunoglobulin retains about 90%-100% antigen binding activity.

In another preferred embodiment, the at least one non photo-reactive functional group is coupled to an effector molecule.

In a preferred embodiment, the immunoglobulin is coupled to a surface where the surface is a drug delivery system selected from the group comprising a liposome, a micelle, a nanoparticle, a quantum dot or dendrimer.

In yet another preferred embodiment, the effector molecule is a labeling molecule, an affinity tag, a chemotherapeutic, a cytotoxic agent, an active peptide, a contrast reagent, a radiolabel, DNA, or a small molecule inhibitor. In another embodiment, the effector molecule is biotin.

In another embodiment, the biotin is bound to streptavidin, where the streptavidin at least partially coats a surface.

In another embodiment, the surface is a nanoparticle, bead, microfluidic device, ELISA plate or microarray device.

In another embodiment, the immunoglobulin is a full length immunoglobulin molecule or a fragment thereof containing the nucleotide binding site of an immunoglobulin.

In still another embodiment, the active peptide is selected from the group consisting of cell internalization sequences, receptor targeting sequences and mimitopes.

In another embodiment, the labeling molecule has fluorescent, absorbent, contrast, or radiolabel function.

In another embodiment, the chemotherapeutic is paclitaxel, the labeling molecule is FITC and the active peptide is a cyclic iRGD.

Another embodiment of the invention provides for a site specific photo crosslinking of an orthogonally reactive functional group to an immunoglobulin comprising the steps of:

a) providing an immunoglobulin, the immunoglobulin having a conserved nucleotide binding site located away from the antigen binding site of the $F_V$ domain of the immunoglobulin;

b) providing a hetero-bifunctional crosslinker having at least a first functional group and at least a second functional group where the first functional group is a heterocyclic photo-reactive functional group and the second functional group is a thiol functional group;

c) mixing the immunoglobulin with the hetero-bifunctional crosslinker to produce a mixture;

d) exposing the mixture to ultra-violet light so that the first functional group is covalently coupled within the nucleotide binding site of the immunoglobulin; and e) reacting the thiol functional group with a functionalized ligand, thereby providing an immunoglobulin having site specific thiolation.

In one embodiment, the heterocyclic photo reactive functional group is an indole compound. In another embodiment, the heterocyclic photo reactive functional group is indole-3-butyric acid. In another embodiment, the thiol functional group is a cysteine residue. In yet another embodiment, the functionalized ligand is coupled to a thiol reactive surface.

In another embodiment, the thiol functional group is coupled to a surface in an orientation specific manner whereby the antigen binding sites are oriented away from the surface and available for antigen binding such that the immunoglobulin retains about 90% to about 100% antigen binding activity.

In another embodiment, the at least one non-photo reactive functional group is coupled to an effector molecule.

In another embodiment, the functionalized surface is a drug delivery system chosen from the group consisting of a liposome, a micelle, a nanoparticle, a quantum dot or dendrimer.

In yet a further embodiment, the functionalized ligand is selected from the group consisting of a labeling molecule, an affinity tag, a chemotherapeutic, a cytotoxic agent, an active peptide, a contrast agent, a radiolabel, DNA, or a small molecule inhibitor.

In another embodiment, the affinity tag is biotin.

In another embodiment, the biotin is coupled to streptavidin, where the streptavidin at least partially coats a surface.

In another embodiment, the coated surface is nanoparticles, beads, microfluidic devices, ELISA plates or a microarray devices.

In another embodiment, immunoglobulin is a full length immunoglobulin molecule or a fragment thereof containing the nucleotide binding site of an immunoglobulin.

In one embodiment, the active peptide is selected from the group consisting of cell internalization sequences, receptor targeting sequences and mimitopes. In some embodiments, the chemotherapeutic is paclitaxel. In another embodiment, the labeling molecule has fluorescent, absorbent, contrast, or radiolabel function. In yet another embodiment, the labeling molecule is FITC.

Another embodiment provides for an isolated immunoglobulin-ligand conjugate comprising an immunoglobulin having a conserved nucleotide binding site located away from the antigen binding site of the $F_V$ domain of the immunoglobulin, the ligand being a hetero-bifunctional crosslinker, the ligand having at least one functional group that is a heterocyclic photo reactive functional group, the ligand also having at least one non-photo reactive functional group, where the at least one heterocyclic photo reactive functional group being coupled to the nucleotide binding site and the at least one non-photo reactive functional group being coupled to an effector molecule.

In another embodiment, the immunoglobulin-ligand conjugate has a non-photo reactive functional group is an orthogonal reactive functional group.

In another embodiment, the immunoglobulin-ligand conjugate has an orthogonal reactive functional group is a thiol group.

In another embodiment, the immunoglobulin-ligand conjugate has at least one photo reactive heterocyclic functional group that is an indole.

In another embodiment, the immunoglobulin-ligand conjugate is coating as least a portion of a surface.

In another embodiment, the immunoglobulin-ligand conjugate has an effector molecule that is a labeling molecule, an affinity tag, a chemotherapeutic, a cytotoxic agent, active peptide, a radiolabel, DNA, or a small molecule inhibitor.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
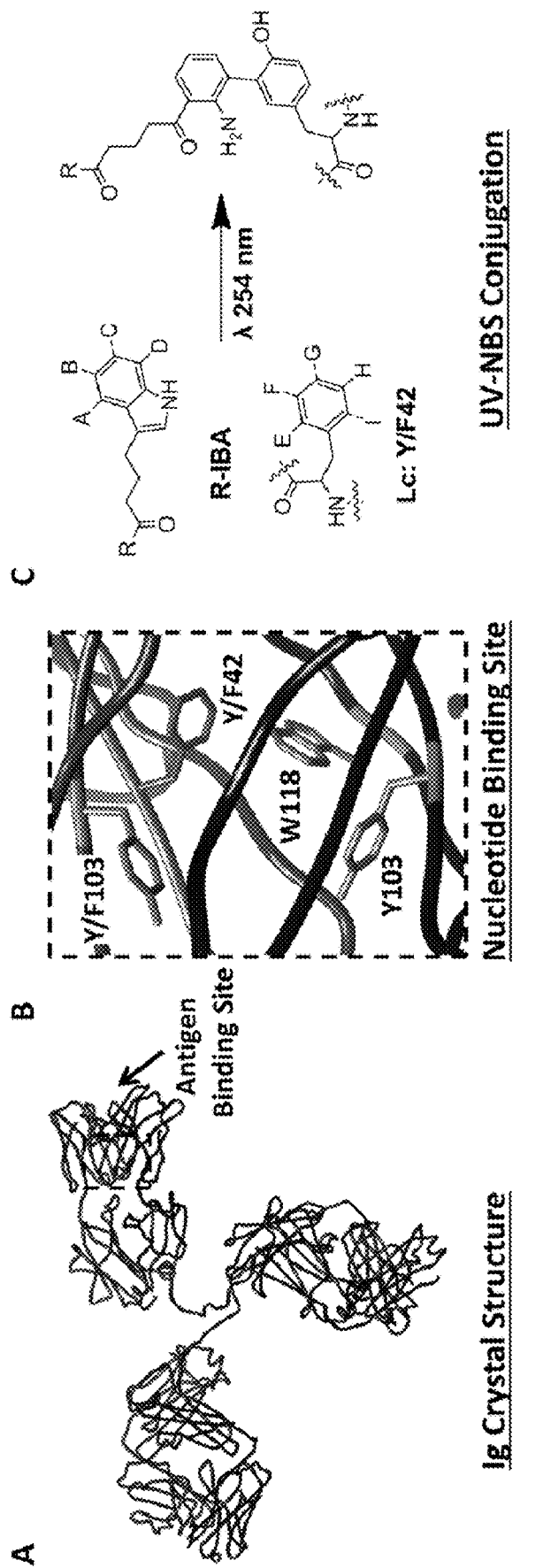
FIG. 1. A) IgG immunoglobulin crystal structure, light chains, heavy chains, and Nucleotide Binding Site (NBS, boxed). B) Rituximab (PDB: 2OSL) with the four NBS residue side chains depicted, two on the light chain and two on the heavy chain, site of conjugation highlighted in purple. C) A UV-NBS crosslinking reaction between the IBA-ligand (R-IBA) and NBS light chain residue Y/F42, according to an embodiment.

Immunoglobulins are extensively used in diagnostic arrays and therapeutic applications due to their exceptional specificity and nearly limitless diversity. This often required the conjugation of the immunoglobulins with a functional ligand. Current methods of conjugating functional ligands to immunoglobulins often suffer from reduced immunoglobulin binding efficiency, reduced access to the Fc domain, complicated and harsh chemical reactions and high overall cost for producing immunoglobulin conjugates. Therefore, a need exists for a cost effective, gentle site selective method to conjugate functional ligands to immunoglobulins without compromising immunoglobulin activity.

The instant application discloses a method of selectively photocrosslinking a functional ligand to an immunoglobulin at the conserved nucleotide binding site (NBS) within the variable region of the Fab arm of the immunoglobulin. This allows the cross-linking of any selected functional ligand to full-length immunoglobulins or an NBS containing immunoglobulin fragment or NBS containing protein. The site of cross-linking is located away from the antigen binding site in the Fv domain avoiding compromising antigen recognition. Thus, the present disclosure provides for a method of site specific affinity crosslinking an immunoglobulin comprising the steps of: a) providing an immunoglobulin, the immunoglobulin having a conserved nucleotide binding site located away from the antigen binding site of the F$_V$ domain of the immunoglobulin; and b) providing a hetero-bifunctional photo-reactive crosslinker, the hetero-bifunctional photo-reactive crosslinker having at least one photo reactive functional group that interacts with the conserved nucleotide binding site of the immunoglobulin, and at least one non-photo reactive functional group; and c) mixing the immunoglobulin with the hetero-bifunctional photo-reactive crosslinker; and d) exposing the mixture to ultra-violet light so that the at least one photo reactive functional group of the heterocyclic photo-reactive crosslinker is covalently coupled within the nucleotide binding site of the immunoglobulin.

In another embodiment, a method is provided for selectively crosslinking a functionalized ligand to the NBS of an immunoglobulin using a photocrosslinker and having a thiol functional group comprising the steps of: a) providing an immunoglobulin, the immunoglobulin having a conserved nucleotide binding site located away from the antigen binding site of the F$_V$ domain of the immunoglobulin; and b) providing a hetero-bifunctional crosslinker having at least a first functional group and at least a second functional group where the first functional group is a heterocyclic photo reactive functional group and the second functional group is a thiol functional group; and c) mixing the immunoglobulin with the hetero-bifunctional crosslinker; and d) exposing the mixture to ultra-violet light so that the first functional group is covalently coupled within the nucleotide binding site of the immunoglobulin; and e) reacting the thiol functional group with a functionalized ligand.

Rajagopolan et al. (*PNAS*, 93:6019-24, 1996) first described the affinity site on immunoglobulins for ATP and Adenosine. This site is referred to as the nucleotide binding site (NBS). The NBS is hydrophobic pocket formed by regions of the heavy chain and light chain and is located away from the antigen binding site. The structure of the NBS was further elucidated by directly implicating four conserved amino acid residues in forming the NBS, two residues from the heavy chain (one tyrosine and one tryptophan residues) and two residues from the light chain (two residues can be either tyrosine or phenylalanine) The rich abundance of aromatic amino acids in the NBS provides an excellent site for photo-crosslinking. Exposing the immunoglobulin to UV light (254 nm wavelength) results in the activation of reactive radicals allowing the formation of covalent bonds with compounds bound to the NBS. The NBS thus provides a useful site for selective conjugation of small compounds containing aromatic rings to immunoglobulins. Any immunoglobulin or fragment thereof having an NBS can be used in the methods according to the instant disclosure. These methods can also be used on non-immunoglobulin proteins having an NBS or NBS-like structure.

The term "immunoglobulin" as used herein, collectively means proteins, whether natural or wholly or partially synthetically produced, that participate in the body's protective immunity by selectively acting against antigens. Immunoglobulins are composed of two identical light chains and two identical heavy chains. The light and heavy chains comprise variable and constant regions. There are five distinct types of heavy chains based on differences in the amino acid sequences of their constant regions: gamma (γ), mu (μ), alpha (α), delta (δ) and epsilon (ε) types, and the heavy chains include the following subclasses: gamma 1 (γ1), gamma 2 (γ2), gamma 3 (γ3), gamma 4 (γ4), alpha 1 (α1) and alpha 2 (α2). Also, there are two types of light chains based on differences in the amino acid sequences of their constant regions: kappa (κ) and lambda (λ) types (Coleman et al., *Fundamental Immunology*, 2nd Ed., 1989, 55-73). According to the features of the constant regions of the heavy chains, immunoglobulins are classified into five isotypes: IgG, IgA, IgD, IgE and IgM.

Immunoglobulins are known to generate several structurally different fragments, which include Fab, F(ab'), F(ab')2, Fv, scFv, Fd and Fc. Among the immunoglobulin fragments, Fab contains the variable regions of the light chain and the heavy chain, the constant region of the light chain and the first constant region ($C_H1$) of the heavy chain, and has a single antigen-binding site. The Fab' fragments differ from the Fab fragments in terms of having the hinge region containing one or more cysteine residues at the C-terminus (carboxyl terminus) of the heavy chain $C_H1$ domain. The F(ab')2 fragments are produced as a pair of the Fab' fragments by disulfide bonding formed between cysteine residues of the hinge regions of the Fab' fragments. Fv is the minimum immunoglobulin fragment that contains only the heavy-chain variable region and the light-chain variable region. The scFv (single-chain Fv) fragments comprise the heavy-chain variable region and the light-chain variable region that are linked to each other by a peptide linker and thus are present in a single polypeptide chain. Also, the Fd fragments comprise only the variable region and $C_H1$ domain of the heavy chain.

The term "Fc fragment", as used herein, is produced when an immunoglobulin molecule is digested with papain, and is a region of an immunoglobulin molecule except for the variable region ($V_L$) and the constant regions ($C_L$) of the light chain and the variable region ($V_H$) and the constant region 1 ($C_H1$) of the heavy chain. An Fc fragment is suitable for use as a drug carrier because it is biodegraded in vivo. Also, an Fc fragment is beneficial in terms of preparation, purification and yield of a complex with the Fc fragment because it has a small molecular weight relative to whole immunoglobulin molecules. Further, since the Fab region, which displays high non-homogeneity due to the difference in amino acid sequence between immunoglobulins, is removed, the Fc fragment has greatly increased substance homogeneity and a low potential to induce serum antigenicity. The Fc fragment may further include the hinge region at the heavy-chain constant region. Also, the Fc fragment may be substantially identical to a native form, or may be an extended Fc fragment that contains a portion or the whole of the heavy-chain constant region 1 ($C_H1$) and/or the light-chain constant region 1 ($C_L1$) as long as it has an improved effect. Also, the Fc fragment may be a fragment having a deletion in a relatively long portion of the amino acid sequence of $C_H2$ and/or $C_H3$. A preferred Fc fragment is an IgG or IgM-derived Fc fragment.

The Fc fragment according to the present invention may be a combination or hybrid, in detail, a combination or hybrid of Fc fragments derived from IgG, IgA, IgD, IgE and IgM. The term "combination" means a dimeric or multimeric polypeptide in which single-chain Fc fragments of the same origin are linked to a single-chain Fc fragment of a different origin to form a dimer or multimer. The term "hybrid" means a polypeptide in which two or more domains of different origin is present in a single-chain Fc fragment. For example, a hybrid may be composed of one to four domains selected from among $C_H1$, $C_H2$, $C_H3$ and $C_H4$ domains contained in IgG1 Fc, IgG2 Fc, IgG3 Fc and IgG4 Fc.

The Fc fragment may be derived from humans or other animals including cows, goats, swine, mice, rabbits, hamsters, rats and guinea pigs, and preferably humans. The human-derived Fc fragment is sometimes preferable to a non-human derived Fc fragment, which may act as an antigen in the human body and cause undesirable immune responses such as the production of a new immunoglobulin against the antigen.

Photocrosslinking Compounds.

The methods described herein require the use of a photocrosslinker that binds to the NBS, forming a covalent bond with the NBS with exposure to UV light. The most useful photocrosslinkers are small, hydrophobic compounds that can associate within the hydrophobic NBS pocket. Moreover, it is preferable that the small photocrosslinker compound has high affinity for the NBS. Preferably, the binding affinity (Kd) of the small photocrosslinking compounds with the NBS is about less than 50 μM, more preferably about less than 10 μM, and still more preferably about less than 8 μM.

In some embodiments, the preferred photocrosslinker is an indole containing compound or indole-like compound. As used herein, the term "indole" refers to an aromatic heterocyclic organic compound having a bicyclic structure that includes a six-membered benzene ring fused to a five-membered nitrogen-containing pyrrole ring, which rings can be substituted. Some examples of indole containing or indole-like compounds include, but are not limited to indole-3-butyric acid, indole-3-acetic acid, 7-methyltryptamine, tryptophan, tryptamine and 5-methylindole-3-carboxaldehyde. In further embodiments, the photocrosslinker can be a bicyclic or tricyclic compound. For example, 1-naphthaleneacetic acid, serotonin hydrochloride, enamine, 2-naphthaleneacetic acid, 2-naphthoic acid, 3-isoquinolinecarboxylic acid hydrate, vitasmlab, 4-oxo-1,4-dihydrobenzo(h)quinolone-3-carboxylic acid, 9-methyl-9h-fluorine-2-carboxylic acid, 9-fluorenone-2-carboxylic acid, (2-(2-benzimidazolylamino)-1-ethanol, and sinefugin can be used with the methods described herein.

In some embodiments, the photocrosslinking compound can have chemical adducts that increase photo reactivity, including examples such as azide moieties, diazirine, aryl azide, fluorinated aryl azide and benzophenone.

Conjugation of Ligands to Indole Compounds.

The compounds of the invention, such as immunoglobulin-ligand conjugate, linkers, and functional ligands, are prepared by conventional methods of organic and bioorganic chemistry. See, for example, Larock, *Comprehensive Organic Transformations*, Wiley-VCH, New York, N.Y., U.S.A. Suitable protective groups and their methods of addition and removal, where appropriate, are described in Greene et al., *Protective Groups in Organic Synthesis*, 2$^{nd}$ ed., 1991, John Wiley and Sons, New York, N.Y., US.

In the methods described herein, generally the photo crosslinker-effector molecule coupling is performed prior to photo crosslinking. In preferred embodiments, the photo crosslinker is an indole or indole-like compound. Preferably, the indole compound is indole-3-butyric acid (IBA). IBA is desirable because it is small and has a high affinity for the nucleotide binding site ($K_a$ between 1-8 µM). Moreover, IBA has a free carboxylic acid group that can be reacted with a myriad of other molecules including effector molecules and functionalized ligands.

The effector molecules and functionalized ligands may be directly attached to the photo affinity compound, or attachment may be accomplished using peptide or non-peptide coupling agent. Peptide linkers are often composed of flexible amino acid residues such as, but not limited to glycine (gly) and serine (ser), often times in repeats. For example, a short peptide linker may be a gly-ser, gly-ser-gly-ser, gly-ser-gly-ser-gly-ser, gly-gly-ser-gly or any combination and multiple thereof as determined by the skilled artisan. The peptide linker may also contain other amino acid residues as required by the skilled artisan. A proline-rich peptide linker can be used if coupling of the ligand to immunoglobulin requires more rigidity. Moreover, short peptide linker sequences can be introduced into a functional ligand as a result of the chemical synthesis process. Suitable linkers also include, for example, cleavable and non-cleavable linkers. A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit), a phenylalanine-lysine (phe-lys) linker, or maleimidocaproic-valine-citruline-p-aminobenzyloxycarbonyl (mc-Val-Cit-PABA) linker. Other suitable linkers include linkers hydrolyzable at a specific pH or a pH range, such as a hydrazone linker. Additional suitable cleavable linkers include disulfide linkers.

Examples of such non peptide linkers include by way of example ethylene glycol, polyethylene glycol, $EG_{11}$-amine, SPDP, IT, dimethyl adipimidate HCl, active esters such as disuccinimidyl suberate, aldehydes such as glutaraldehyde, bis-azido compounds, bis-diazonium derivatives such as bis-(p-diazonium benzoyl)-ethylenediamine, diisocyanates such as tolylene 2,6-diisocyanate, and bis-active fluorine compounds such as 1,5-difluoro-2,4-ditrobenzene.

In some embodiments, an IBA derivative is IBA-$EG_{11}$-amine (although any suitable and effective length of EG may be used). The IBA-$EG_{11}$-amine derivative can be easily reacted with an amine reactive maleic anhydride molecule. As an example, maleic anhydride molecules can be used to coat various surfaces of interest, such as, for example, microtiter plates used in ELISA assays. The IBA-$EG_{11}$-amine can then be directly coupled to the maleic anhydride coated surface. Alternatively, IBA-$EG_{11}$-amine can be reacted with an effector molecule having an amine reactive maleic anhydride. Moreover, an effector molecule can, in some instances, be modified to incorporate a maleic anhydride to react with IBA-$EG_{11}$-amine.

In other embodiments, IBA-$EG_{11}$-amine can be directly coupled to biotin, which can be used in a biotin-streptavidin binding system. Avidin is a small protein having a strong affinity for biotin, a co-factor that plays a role in multiple eukaryotic biological processes. Avidin and other biotin-binding proteins, including streptavidin and NeutrAvidin Protein, have the ability to bind up to four biotin molecules. The avidin-biotin complex is the strongest known non-covalent interaction ($K_d=10^{-15}$M) between a protein and ligand. The bond formation between biotin and avidin is very rapid, and once formed, is unaffected by extremes of pH, temperature, organic solvents and other denaturing agents. Streptavidin is useful for, but not limited to coating of surfaces, protein purification, immunoglobulin detection and protein labeling.

In still other embodiments, IBA can be coupled to various known effector molecules using methods known to a person of ordinary skill in the art prior to photo activation and coupling to the NBS site. In addition to IBA-biotin conjugates, some embodiments include, but are not limited to IBA-FITC, IBA-iRGD, IBA-paclitaxel and IBA-CD20 mimotope.

In some instances, where functional ligands are UV sensitive, it may be necessary to use an orthogonal reactive group to photocrosslink UV sensitive moieties to the NBS. Orthogonal reactive groups are molecules that have different reactive groups on each end of the crosslinker. Examples of orthogonal chemistries include, but are not limited to maleimide/thiol chemistry, click chemistry and other orthogonal chemistries to primary amine chemistry, for example, ketones, aldehydes, azides, and/or alkynes.

In some embodiments, an IBA derivative has an orthogonal thiol group. By synthesizing, for example, an IBA conjugated version of cysteine, the thiol group can be used as an orthogonally reactive site to conjugate various types of functional ligands that possess thiol reactive groups through disulfide bond formation or reaction with a maleimide functionalized ligand. This conjugation strategy has near limitless uses across various diagnostic and therapeutic applications for the preparation of site specific conjugation of affinity tags, fluorescent molecules, peptides and chemotherapeutics to immunoglobulins.

A non-exhaustive list of functional ligands that can be used to make immunoglobulin-functional ligand conjugates is listed below.

In some embodiments, the effector molecule or functionalized ligand is a labeling molecule, an affinity tag, a chemotherapeutic, a cytotoxic agent, or an active peptide.

A "chemotherapeutic agent" as used herein is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, immunoglobulins, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N, N-dimethyl-ethanamine, NOLVADEX®, ISTUB AL®, VALODEX®), and doxorubicin (ADRIAMYCIN®), Akti-1/2, HPPD, and rapamycin.

Additional examples of suitable chemotherapeutic agents include: oxaliplatin (ELOXATIN®, Sanofi), bortezomib (VELCADE®, Millennium Pharm.), sutent (SUNITINIB®, SU1 1248, Pfizer), letrozole (FEMARA®, Novartis), imatinib mesylate (GLEEVEC®, Novartis), XL-518 (MEK inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAV AR®, BAY43-9006, Bayer Labs), gefitinib (IRESS A®, AstraZeneca), irinotecan (C AMPTOS AR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gammall, calicheamicin omegall (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (T-2 toxin, verracurin A, roridin A and anguidine); urethan; vindesine; dacarbazine; mannomustine; mitobronitol; mitolactol; pipobroman; gacytosine; arabinoside (Ara-C); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELOD A®, Roche); ibandronate; CPT-I1; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (NOLVADEX®; tamoxifen citrate), raloxifene, droloxifene, 4-hydroxytamoxifen, trioxifene, keoxifene, LY1 17018, onapristone, and FARESTON® (toremifene citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

In some embodiments, the effector molecules may also include cytotoxins or cytotoxic agents including any agent that is detrimental to (e.g. kills or inhibits the growth or division of) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Some embodiments may also include physiologically active peptides as the functional ligand. Such physiologically active polypeptides include various physiologically active peptides used for treating or preventing human diseases, which are exemplified by hormones, cytokines, enzymes, immunoglobulins, growth factors, transcription regulatory factors, coagulation factors, vaccines, structural proteins, ligand proteins or receptors, cell surface antigens and receptor antagonists, and derivatives and analogues thereof. Other peptides include homophillic peptide sequences, cell internalization sequences, receptor targeting sequences and mimitopes.

In detail, non-limiting examples of the drugs include human growth hormone, growth hormone releasing hormone, growth hormone releasing peptide, interferons and interferon receptors (e.g., interferon-α, -β and -γ, water-soluble type I interferon receptor, etc.), granulocyte colony stimulating factor (G-CSF), granulocyte-macrophage colony stimulating factor (GM-CSF), glucagon-like peptides (e.g., GLP-1, etc.), G-protein-coupled receptor, interleukins (e.g., interleukin-1, -2, -3, -4, -5, -6, -7, -8, -9, -10, -11, -12, -13, -14, -15, -16, -17, -18, -19, -20, -21, -22, -23, -24, -25, -26, -27, -28, -29, -30, etc.) and interleukin receptors (e.g., IL-1 receptor, IL-4 receptor, etc.), enzymes (e.g., glucocerebrosidase, iduronate-2-sulfatase, alpha-galactosidase-A, agalsidase alpha and beta, alpha-L-iduronidase, butyrylcholinesterase, chitinase, glutamate decarboxylase, imiglucerase, lipase, uricase, platelet-activating factor acetylhydrolase, neutral endopeptidase, myeloperoxidase, etc.), interleukin and cytokine binding proteins (e.g., IL-18 bp, TNF-binding protein, etc.), macrophage activating factor, macrophage peptide, B cell factor, T cell factor, protein A, allergy inhibitor, cell necrosis glycoproteins, immunotoxin, lymphotoxin, tumor necrosis factor, tumor suppressors, metastasis growth factor, alpha-1 antitrypsin, albumin, alpha-lactalbumin, apolipoprotein-E, erythropoietin, highly glycosylated erythropoietin, angiopoietins, hemoglobin, thrombin, thrombin receptor activating peptide, thrombomodulin, factor VII, factor VIIa, factor VIII, factor IX, factor XIII, plasminogen activating factor, fibrin-binding peptide, urokinase, streptokinase, hirudin, protein C, C-reactive protein, renin inhibitor, collagenase inhibitor, superoxide dismutase, leptin, platelet-derived growth factor, epithelial growth factor, epidermal growth factor, angiostatin, angiotensin, bone growth factor, bone stimulating protein, calcitonin, insulin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factors (e.g., nerve growth factor, cilliary neurotrophic factor, axogenesis factor-1, brain-natriuretic peptide, glial derived neurotrophic factor, netrin, neurophil inhibitor factor, neurotrophic factor, neuturin, etc.), parathyroid hormone, relaxin, secretin, somatomedin, insulin-like growth factor, adrenocortical hormone, glucagon, cholecystokinin, pancreatic polypeptide, gastrin releasing peptide, corticotropin releasing factor, thyroid stimulating hormone, autotaxin, lactoferrin, myostatin, receptors (e.g., TNFR(P75), TNFR (P55), IL-1 receptor, VEGF receptor, B cell activating factor receptor, etc.), receptor antagonists (e.g., IL1-Ra etc.), cell surface antigens (e.g., CD 2, 3, 4, 5, 7, 11a, 11b, 18, 19, 20, 23, 25, 33, 38, 40, 45, 69, etc.), monoclonal immunoglobulins, polyclonal immunoglobulins, immunoglobulin fragments (e.g., scFv, Fab, Fab', F(ab')2 and Fd), vaccines, and virus derived vaccine antigens.

Still other effector molecules may include detectable substances useful for example in diagnosis. Examples of detectable substances include various enzymes, prosthetic groups, fluorescent materials, luminescent materials, contrasting agents, absorbent agents, bioluminescent materials, DNA molecules, RNA molecules, radioactive nuclides such as $^{111}$In, $^{125}$I, $^{131}$I, $^{90}$Y, Lu$^{177}$, Bismuth$^{213}$, Californium$^{252}$, Iridium$^{192}$ and Tungsten$^{188}$/Rhenium$^{18}$, positron emitting metals (for use in positron emission tomography), and nonradioactive paramagnetic metal ions. See generally U.S. Pat. No. 4,741,900 (Alvarez et al.) for metal ions which can be conjugated to immunoglobulins for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

Reaction Conditions.

Figure 19:
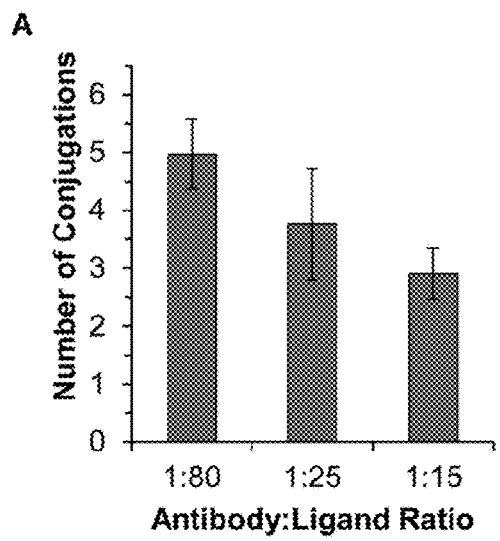
FIG. 19. All samples were exposed to 2 $J/cm^2$ of UV energy to provide for the highest number of conjugations to better demonstrate the effects that buffer conditions and IBA-ligand concentration can have on the number of conjugations. Rituximab was used as a representative IgG immunoglobulin for this study. A) Keeping the immunoglobulin concentration constant at 20 µM and increasing the IBA-FITC concentration from 300-1600 µM results in an increase in the number of non-specific conjugations as indicated by an increase in the total number of conjugations approaching 5. This result was expected due to the hydrophobic nature of the IBA moiety and increased concentrations promoting non-specific interactions of IBA-FITC to the immunoglobulin surface, and upon UV exposure, there was an increase in the non-site specific conjugations. B) The immunoglobulin concentration (20 µM) and IBA-FITC concentration (300 µM) were kept constant and the pH of the buffer was varied to determine its effect on the number of conjugations. Reducing the pH reduces the number of conjugations while increasing the pH increases the number of conjugations. This result is consistent with the known increase in photo-reactivity of amino acids, such as histidine and lysine, at elevated pH values. C) The addition of Tween 20 to PBS pH 7.4 has little effect on the number of conjugations. Tween 20 does not inhibit NBS binding because addition of Tween 20 may be necessary to increase the coupling yield of larger moieties to the NBS. All data represents means (±SD) of triplicate experiments.
Figure 19:
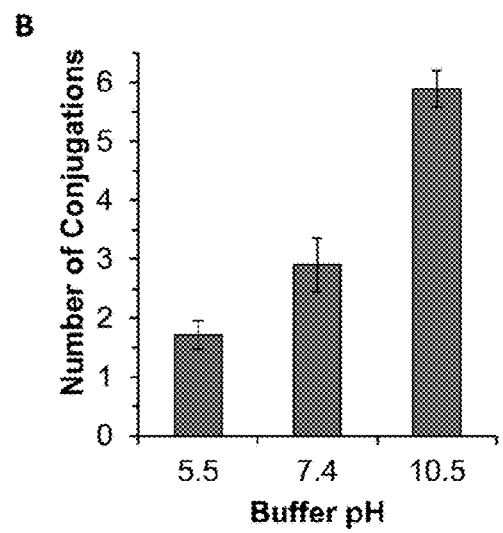
Figure 19:
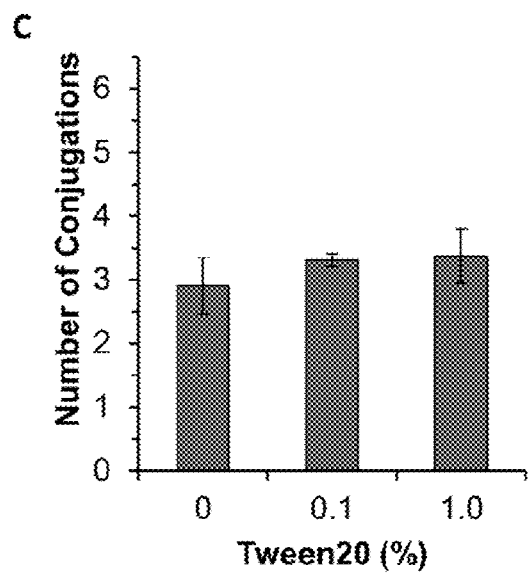

The efficiency of photo crosslinking can also be controlled by varying the experimental conditions under which the reaction is performed. For example, the UV energy, pH, IBA-ligand concentration, IBA-ligand to immunoglobulin ratio, salt concentration and the presence of surfactants can all influence the efficiency of the crosslinking (see FIG. 19).

In a preferred embodiment, the intensity of the UV energy should be an amount that maximizes photo-incorporation obtained in a minimum amount of time without appreciable change in temperature or damage to the immunoglobulin or functional ligand. Photocrosslinking can be performed using any wavelength in the UV spectrum. Preferably the photocrosslinking is achieved at 254 nm with a UV light source. The UV light source can be from any UV source capable of providing the necessary amount of energy that is known to a person of ordinary skill in the art. Preferably, the samples are places about 2-8 inches from the UV source. More preferably, the samples are about 3-4 inches from the UV light source. The UV intensity is preferably about 100-1500 µW/cm$^2$, and more preferably about 500 µW/cm$^2$.

UV light is essential for the activation of the photocrosslinker, but only a low energy UV light is necessary. The energy of the UV light can range from 0.1-10 J/cm², or preferably 0.1-5 J/cm², or even more preferably 0.1-3 J/cm². The preferred photo activation time ranges from approximately 5-240 seconds. Each immunoglobulin contains two NBS's. Preferably then, the amount of UV energy applied to the crosslinking reactions is such that two ligands are conjugated to the immunoglobulin (one at each NBS). Tables 1-4 below show the UV energy levels to reach a conjugation average of two ligands per immunoglobulin.

TABLE 1

Number of UV conjugations per immunoglobulin with varying UV energy exposure from 0-3.0 J/cm² at an IBA-FITC concentration of 300 μM.

| UV Energy | Average Number of Conjugations Per Immunoglobulin | | | |
|---|---|---|---|---|
| (J/cm2) | Rituximab | SD | IgG$^{DNP}$ | SD |
| 0 | 0.1 | 0.01 | 0 | 0.01 |
| 0.1 | 0.5 | 0.01 | 0.7 | 0.06 |
| 0.5 | 1.2 | 0.01 | 1.7 | 0.00 |
| 1.0 | 2.1 | 0.03 | 2.3 | 0.10 |
| 2.0 | 2.9 | 0.44 | 2.9 | 0.46 |
| 3.0 | 3.2 | 0.65 | 3.4 | 0.55 |

TABLE 2

Number of UV conjugations per immunoglobulin with varying IBA-FITC concentration from 0-300 μM at 1 J/cm².

| IBA-FITC Conc. | Average Number of Conjugations Per Immunoglobulin | | | |
|---|---|---|---|---|
| (μM) | Rituximab | SD | IgG$^{DNP}$ | SD |
| 0 | 0 | 0.01 | 0 | 0.01 |
| 15 | 0.1 | 0.01 | 0.1 | 0.01 |
| 50 | 0.6 | 0.04 | 0.7 | 0.02 |
| 100 | 1.2 | 0.07 | 1.4 | 0.08 |
| 200 | 2.2 | 0.10 | 2.4 | 0.36 |
| 300 | 2.5 | 0.32 | 2.6 | 0.55 |

TABLE 3

Number of UV conjugations per immunoglobulin varying UV energy exposure from 0-2.0 J/cm² for IBA-iRGD and IBA-paclitaxel at a ligand concentration of 300 μM.

| | UV Energy | Average Number of Conjugations Per Immunoglobulin | | | |
|---|---|---|---|---|---|
| | (J/cm2) | Rituximab | SD | IgG$^{DNP}$ | SD |
| IBA-iRGD | 0 | 0 | 0.06 | 0 | 0.07 |
| | 0.5 | 0.2 | 0.05 | 0.4 | 0.10 |
| | 1.0 | 1.1 | 0.12 | 1.2 | 0.17 |
| | 2.0 | 2.0 | 0.10 | 2.1 | 0.24 |
| IBA-paclitaxel | 0 | 0 | 0.05 | 0 | 0.06 |
| | 0.5 | 0.4 | 0.08 | 0.1 | 0.03 |
| | 1.0 | 0.8 | 0.11 | 0.4 | 0.11 |
| | 2.0 | 1.1 | 0.05 | 1.0 | 0.17 |

TABLE 4

Number of UV conjugations per immunoglobulin with varying UV energy exposure from 0-1.5 J/cm² at an IBA-FITC or IBA-Thiol (300 μM), via fluorescein-5-maleimide.

| UV Energy | Average Number of Conjugations Per Immunoglobulin | | | |
|---|---|---|---|---|
| (J/cm²) | IBA-FITC | SD | IBA-Thiol | SD |
| 0 | 0 | 0.01 | 0 | 0.02 |
| 0.5 | 0.61 | 0.01 | 0.80 | 0.03 |
| 1.0 | 1.23 | 0.02 | 1.24 | 0.03 |
| 1.5 | 1.71 | 0.08 | 1.41 | 0.03 |

In a preferred embodiment, the pH of the reaction varies according to the functionalized ligand. Preferably, the pH range is about 6-8, or more preferably about 6.8-7.4. When using a thiol functional group, however, keeping the pH about 6.8 will aid in preventing the spontaneous formation of disulfide bridges.

The concentration of IBA-ligand has an effect on the efficiency of photo crosslinking. In a preferred embodiment, the concentration of IBA-ligand is greater than 100 μM and more preferably about 100 μM-400 μM. Moreover, the ratio of immunoglobulin to IBA-ligand is preferably about 1:10-1:20.

Additionally, surfactants may influence the efficiency of photo crosslinking to the immunoglobulin molecule. Surfactants are compounds that lower the surface tension between two liquids or between a liquid and a solid. Surfactants contain both hydrophobic and hydrophilic groups. Surfactants can be useful in reducing undesired non-specific hydrophobic interactions between proteins. This is especially useful when the IBA-ligand is a peptide or chemotherapeutics compound. Examples of ionic and non-ionic surfactants that can be used are n-Octyl β-D-Glucopyranoside, Polyethylene Glycol Mono-4-octylphenyl Ether, Polyethylene Glycol Monocetyl Ether, Polyethylene Glycol Monododecyl Ether, Tween 20, Tween 40, Tween 60, Tween 80, Tween 85, Sodium Deoxycholate, Lithium Dodecyl Sulfate, Sodium Dodecyl Sulfate, Sodium Cholate, Sodium N-Lauroylsarcosinate Hydrate, Lauryl Sulfobetaine, Caprylyl Sulfobetaine, n-Octyl Sulfobetaine, Palmityl Sulfobetaine and Myristyl Sulfobetaine Drug Delivery Systems.

Drug delivery is the method or process of administering a pharmaceutical or biologically active compounds to achieve a therapeutic effect in humans or animals. The most common routes of administration include the oral, topical, transmucosal and inhalation routes. Despite recent advances in technology, many medications such as peptides, immunoglobulins, vaccines and other gene based drugs generally may not be delivered using these routes because they might be susceptible to enzymatic degradation or cannot be absorbed into the systemic circulation efficiently due to molecular size and charge issues to be therapeutically effective.

The methods of the instant application can be used to coat the surfaces of various drug delivery systems including, but not limited to liposomes, preliposomes, micelle, dendrimers, microspheres, gold nanoparticles, polymer nanoparticles, metallic nanoparticles, ceramic nanoparticles, quantum dots, magnetic, metallic, nanoshells, ceramic, carbon nanotubes, viral-based nanoparticle and silica beads.

Diagnostic Assays.

Ideally, several diagnostic assay methods, including ELISA, Dipstick tests, lateral flow, microfluidic devices, and microarrays can be used to detect an antigen of interest.

ELISA assays are widely used methods for the detection of specific antigens in a biological sample. It involves the immobilization of an immunoglobulin (primary immunoglobulin) to a solid support surface such as plastic microplates, and detecting a specific antigen via binding to the immobilized immunoglobulin, followed by addition of secondary immunoglobulin or immunoglobulins, the latter usually being conjugated to enzymes such as alkaline phosphatase or horseradish peroxidase in order to facilitate detection. Addition of a chemical substrate of the enzyme results in the development of a colored reaction product, which indicates the presence of the antigen of interest in the sample.

Hence, according to a preferred embodiment, the immune affinity procedure may be an ELISA immunoassay selected from the group consisting of direct enzyme-linked immunosorbent assays, indirect enzyme-linked immunosorbent assays, direct sandwich enzyme-linked immunosorbent assays, indirect sandwich enzyme-linked immunosorbent assays, and competitive enzyme-linked immunosorbent assays.

In one embodiment, detection is effected through capture ELISA. Capture ELISA (also known as "sandwich" ELISA) is a sensitive assay to quantify picogram to microgram quantities of substances (such as hormones, cell signaling chemicals, infectious disease antigens and cytokines.). This type of ELISA is particularly sought after when the substance to be analyzed may be too dilute to bind to the microtiter plate (such as a protein in a cell culture supernatant) or does not bind well to plastics (such as a small organic molecule). Optimal dilutions for the capture immunoglobulins, samples, controls, and detecting immunoglobulins as well as incubation times are determined empirically and may require extensive titration. Ideally, one would use an enzyme-labeled detection immunoglobulin. However, if the detection immunoglobulin is unlabeled, the secondary immunoglobulin should not cross-react with either the coating immunoglobulin or the sample. Optimally, the appropriate negative and positive controls should also be included.

The capture or coating immunoglobulin to be used should be diluted in carbonate-bicarbonate buffer or PBS. Capture immunoglobulins are typically plated at 0.2 to 10 µg/mL. It is preferable to use affinity purified immunoglobulins or at a minimum use an IgG fraction. Generally samples are diluted in PBS (the more sensitive the assay, the less sample is required).

The immunoglobulins may be labeled directly or indirectly by a detectable moiety.

As used herein in the specification, the term "detectable moiety" refers to any atom, molecule or a portion thereof, the presence, absence or level of which may be monitored directly or indirectly. One example includes radioactive isotopes. Other examples include (i) enzymes which can catalyze color or light emitting (luminescence) reactions and (ii) fluorophores, (iii) surface plasmon resonance (SPR), (iv) waveguides, and (v) impedance to quantify bound antigen. The detection of the detectable moiety can be direct provided that the detectable moiety is itself detectable (i.e. can be directly visualized or measured), such as, for example, in the case of fluorophores. Alternatively, the detection of the detectable moiety can be indirect. In the latter case, a second moiety that reacts with the detectable moiety, itself being directly detectable is preferably employed. The detectable moiety may be inherent to the immunoglobulin. For example, the constant region of an immunoglobulin can serve as an indirect detectable moiety to which a secondary immunoglobulin having a direct detectable moiety can specifically bind.

Thus, secondary immunoglobulins are particular suitable means for the detection of the primary immunoglobulin in the method of the invention. This secondary immunoglobulin may be itself conjugated to a detectable moiety. One of the ways in which an immunoglobulin in accordance with the present invention can be detectably labeled is by linking the same to an enzyme. The enzyme, in turn, when exposed to an appropriate substrate, will react with the substrate in such a manner as to allow its detection, for example by producing a chemical moiety which can be detected, for example, by spectrophotometric, fluorometric or by visual means. Enzymes which can be used to label the immunoglobulin include, but are not limited to, horseradish peroxidase, alkaline phosphatase, malate dehydrogenase, staphylococcal nuclease, delta-5-steroid isomerase, yeast alcohol dehydrogenase, alpha-glycerophosphate dehydrogenase, triose phosphate isomerase, asparaginase, glucose oxidase, beta-galactosidase, ribonuclease, urease, catalase, glucose-6-phosphate dehydrogenase, glucoamylase and acetylcholinesterase, or any other enzyme which can be conjugated to an immunoglobulin and its reaction with a substrate, measured (or detected).

The detection can be accomplished by colorimetric methods, which employ a chromogenic substrate for the enzyme. Detection may also be accomplished by visual comparison of the extent of enzymatic reaction of a substrate in comparison with similarly prepared standards.

Figure 38:
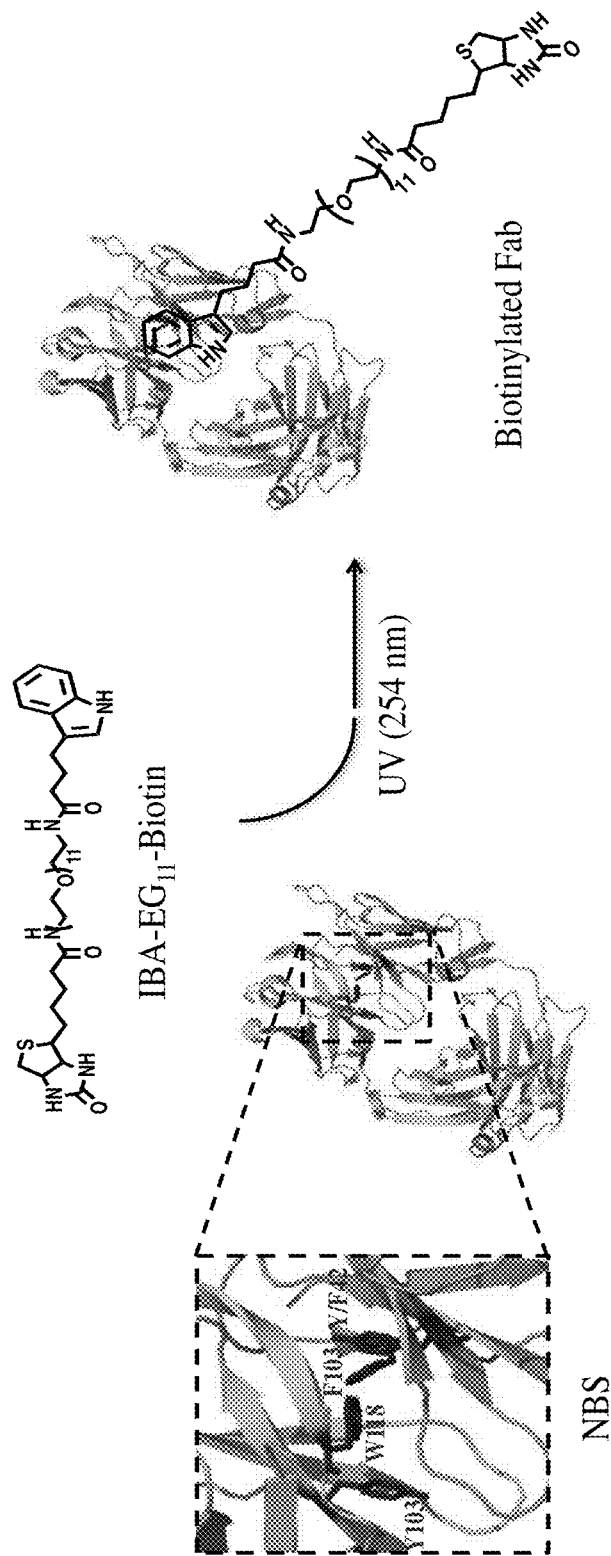
FIG. 38. Schematic representation of UV-NBS$^{Biotin}$ crosslinking method. Blue labeled and magnified residues represents the nucleotide binding site (NBS) on an anti-Ebola KZ52 Fab fragment. A covalent bond is formed between the IBA-EG$_{11}$-Biotin and Fab Fragment at the NBS site upon UV exposure preserving Fab fragment's antigen binding activity. The biotinylated Fab fragment can then bind to NeutrAvidin coated plate, immobilizing the Fab fragments to the surface.

The solid support surface to which the first immunoglobulin is bound may be any water-insoluble, solid support. Examples of suitable solid support include, but are not limited to, are large beads, e.g., of polystyrene, filter paper, slides, chips, test tubes, and microtiter plates. The first immunoglobulin may be bound to the solid support surface as described above. For example, the immunoglobulin may be bound to the surface through a biotin-streptavidin interaction, or through the interaction with and amine reactive maleic anhydride (see FIGS. 38 and 40).

The solid support surface mentioned above can include polymers, such as polystyrene, agarose, Sepharose (a cross-linked, beaded-form of agarose), cellulose, glass beads and magnetizable particles of cellulose or other polymers. The solid-support can be in the form of large or small beads or particles, tubes, plates, slides, chips or other forms. As a solid support surface, use is preferably made of a test tube, or a microtiter plate the inner walls of which are coated with a first immunoglobulin.

In a further embodiment, Dipstick assays can be used to detect an antigen of interest. Dipstick assays use the well-established lateral flow format, wherein capture immunoglobulins are striped or banded onto nitrocellulose membrane and a wicking pad draws the sample up through the dipstick, whereby the antigen of interest interact with the appropriate immunoglobulin. Other immunoglobulins specific to other antigens of interest can be included. Subsequent analysis of enzyme activity and protein quantity can be done using standard methods known to a person skilled in the art, or as discussed above regarding ELISAs.

In another preferred embodiment, Microfluidic devices, which may also be referred to as "lab-on-a-chip" systems, biomedical micro-electro-mechanical systems (bioMEMs), or multicomponent integrated systems, can be used for detecting an antigen of interest. Such systems miniaturize and compartmentalize processes that allow for detection of antigens of interest, and other processes such as SPR, waveguide, and impedance quantification.

Array-based assays and bead-based assays can be used with microfluidic devices. For example, an immunoglobulin can be coupled to beads and the binding reaction between the coated beads and antigen of interest can be performed in a microfluidic device. Multiplexing, or detecting more than one antigen of interest at once, can also be performed using a microfluidic device. Different compartments can comprise different immunoglobulin populations for different antigens of interest, where each population has a different target antigen.

In another embodiment, microarrays are used to detect antigens of interest. Microarrays are typically small, high throughput chips generally made of a solid support structure, typically glass slides, nitrocellulose, or microtiter plates. Generally, immunoglobulins to antigen of interest are bound to the solid support surface. Detection of the captured antigen can be accomplished as discussed above for ELISA detection, or through any method known to a person of ordinary skill in the art.

Commercial Kits.

The present disclosure is also directed to a kit or system useful for practicing the methods described herein. The kit may be a packaged combination of one or more containers, devices, or the like holding the necessary reagents, and usually including written instructions for the performance of assays. The kit may include containers to hold the materials during storage, use or both. The kit of the present invention may include any configurations and compositions for performing the various assays described herein, including, but not limited to a means of detecting an antigen of interest and a means to detect the recognition of the detection. Alternatively, a kit may only include a detection device having a means for detecting an antigen of interest, and a means for recognition of the detection. Alternatively, the kit may only include a detection device having a means for detecting an antigen of interest. A means of detection may be an immunoglobulin specific to an antigen of interest.

In a further embodiment of the kit provided herein, at least one reagent is provided for the detection of the recognition of the means of detecting the antigen of interest, which is accomplished by suitable means. Suitable means may be an immune affinity procedure, an enzymatic assay, or means for detecting a structural feature, amongst others.

In another further embodiment, the detection of the recognition of at least one means of detecting an antigen of interest is achieved through an immune affinity procedure is any one of enzyme-linked immunosorbent assay (ELISA), Western Blot, immuno-precipitation, FACS, Biochip array, Lateral Flow, Time Resolved Fluorometry, immuno-fluorochemistry, ECL procedures, or any other procedure based on immune recognition.

In some embodiments, the kit may comprise a detection device having at least one compartment. One compartment may have an array of at least one means of detection wherein each means of detection is located in a defined position in the array. The term "array" as used by the methods and kits of the invention refers to an "addressed" spatial arrangement of the recognition means. Each "address" of the array is a predetermined specific spatial region containing a recognition agent. For example, an array may be a plurality of vessels (test tubes), plates, micro-wells in a micro-plate each containing a different immunoglobulin. An array may also be any solid support holding in distinct regions (dots, lines, columns) different and known recognition agents, for example immunoglobulins. The array preferably includes built-in appropriate controls, for example, regions without the sample, regions without the immunoglobulin, regions without either, namely with solvent and reagents alone and regions containing synthetic or isolated proteins or peptides, corresponding to the antigen of interest (positive control). Solid support surfaces used for the array of the invention will be described in more detail herein after, in connection with the kits provided by the invention.

A solid support surface suitable for use in the kits of the present invention is typically substantially insoluble in liquid phases. Solid support surfaces of the current invention are not limited to a specific type of support surface. Rather, a large number of supports are available and are known to one of ordinary skill in the art. Thus, useful solid supports include solid and semi-solid matrixes, such as aerogels and hydrogels, resins, beads, biochip arrays (including thin film coated biochips), microfluidic devices, a silicon chip, multi-well plates (also referred to as micro-titer plates or microplates), lateral flow devices, membranes, filters, dip stick tests, conducting and non-conducting metals, glass (including microscope slides) and magnetic support surfaces. More specific examples of useful solid support surfaces include silica gels, polymeric membranes, particles, derivatized plastic films, glass beads, cotton, plastic beads, alumina gels, and polysaccharides such as Sepharose, nylon, latex bead, magnetic bead, paramagnetic bead, super-paramagnetic bead, starch and the like. It should be further noted that any of the reagents included in any of the methods and kits of the invention may be provided as reagents embedded, linked, connected, attached placed or fused to any of the solid support surfaces described above.

An exemplary kit disclosed herein may contain, for example, any combination of:

(a) at least one immunoglobulin prepared according to the methods described herein to detect an antigen of interest;
(b) at least one reagent that allows the detection of the immunoglobulin-antigen interaction;
(c) a detection device;
(d) a reaction compartment containing at least one means to detect the antigen of interest;
(e) a control sample;
(f) an IBA-ligand of interest;
(g) an IBA-linker-ligand of interest;
(h) an IBA-thiol-ligand of interest;
(i) an IBA-linker-thiol-ligand of interest;
(j) an IBA-thiol; and/or
(k) a ligand with maleimide/thiol functionality.

In a preferred embodiment, the supplied immunoglobulin is specific to the prostate specific antigen (PSA), also known as Kaillikrein-3. PSA is a 30-34 kDa glycoprotein enzyme whose serum levels have been implicated in the early detection of prostate cancer. Detection of PSA using the methods described herein have shown an increase of dynamic detection range, lower limit of detection, higher antigen sensitivity and higher signal intensity when compared to detection methods known to the skilled artisan (see FIGS. 43-44).

In further embodiments, the kit may contain an IBA conjugated compound. For example, the kit may contain the IBA conjugates: IBA-linker-biotin, IBA-linker-MAL/Cys, IBA-linker-FITC, IBA-linker-hexa histadine tag, IBA-linker-peptide, IBA-PEG200-lipid, IBA-Lys-FITC, IBA-EG$_{11}$-amine, IBA-EG$_2$-Lys-Lys-Cys, IBA-EG$_2$-His$_6$-Lys-FITC and IBA-thiol-FITC. The kit may also include the above listed IBA conjugates pre-coupled to an immunoglobulin of interest. The kit may also contain IBA-chemotherapeutics, IBA-cytotoxic agents, IBA-contrasting agents, IBA-active peptides, IBA-thiol-chemotherapeutics, IBA-thiol-cytotoxic agents, IBA-thiol-contrasting agents and IBA-thiol-active peptides. The kit can further contain ligands that are thiol reactive such as maleimide-FITC.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase "one or more" is readily understood by one of skill in the art, particularly when read in context of its usage.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

As used herein, an "active peptide" refers to a short amino acid sequences, produced either naturally or synthetically that have hormone or drug like activity that can modulate physiological function through interaction with a target molecule.

As used herein, "photo reactive" refers to crosslinking molecules that are capable of forming a covalent bond with another molecule after exposure to ultra-violet light.

As used herein, an "immunoglobulin-ligand conjugate" refers to an immunoglobulin that is conjugated to one or more effector molecules.

As used herein, "antigen binding site" refers to the part of an immunoglobulin molecule that binds antigen specifically.

As used herein, the terms "contrast agent" or "contrasting agent" refers to a substance used to enhance the contrast of structures, cells or fluids within the body in diagnostic and medical imaging.

As used herein, the term "fragment" refers to a peptide or polypeptide comprising an amino acid sequence of at least 2 contiguous amino acid residues, at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of a primary or secondary effector molecule.

As used herein, the term "isolated" in the context of a peptide, polypeptide, fusion protein, antibody or antigen-binding antibody fragment refers to a peptide, polypeptide, fusion protein, antibody or antigen-binding antibody fragment which is substantially free of cellular material or contaminating proteins from the cell or tissue source from which it is derived or obtained, or substantially free of chemical precursors or other chemicals when chemically synthesized. The language "substantially free of cellular material or contaminating protein" includes preparations of a peptide, polypeptide, fusion protein, antibody or antigen-binding antibody fragment in which the peptide, polypeptide, fusion protein, antibody or antigen-binding antibody fragment is separated from cellular components of the cells from which it is isolated or recombinantly produced. Thus, a peptide, polypeptide, fusion protein, antibody or antigen-binding antibody fragment that is substantially free of cellular material or contaminating protein includes preparations of a peptide, polypeptide, fusion protein, antibody or antigen-binding antibody fragment having less than about 30%, about 20%, about 10%, or about 5% (by dry weight) of other protein. When the peptide, polypeptide, fusion protein, antibody or antigen-binding antibody fragment is recombinantly produced, it is also preferably substantially free of culture medium, i.e., culture medium represents less than about 20%, about 10%, or about 5% of the volume of the protein preparation. When the peptide, polypeptide, fusion protein, antibody or antigen-binding antibody fragment is produced by chemical synthesis, it is preferably substantially free of chemical precursors or other chemicals, i.e., it is separated from chemical precursors or other chemicals which are involved in the synthesis of the peptide, polypeptide, fusion protein, antibody or antigen-binding antibody fragment. Accordingly, such preparations of a peptide, polypeptide, fusion protein, antibody or antigen-binding antibody fragment have less than about 30%, about 20%, about 10%, about 5% (by dry weight) of chemical precursors or compounds other than the peptide, polypeptide, fusion protein, antibody The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Nucleotide Binding Site Conjugation

The nucleotide binding site (NBS) provides a useful site for selective conjugation of immunoglobulins to small ligands that contain aromatic rings to selectively bind this site. To identify such small molecules with a high binding affinity and selectivity for the NBS, we performed an in silico screening by docking various small molecules from the ZINC database at the NBS. The top scoring molecules were then experimentally investigated for their binding affinity to the NBS with indole-3-butyric acid (IBA) emerging as the highest affinity binding nucleotide analogue, with $K_d$ values ranging between 1 and 8 µM depending on the immunoglobulin. Consequently, the IBA conjugated versions of functional ligands (IBA-ligand)—such as affinity tags, fluorescent molecules, peptides, and chemotherapeutics can be photocrosslinked to immunoglobulins site-specifically at the NBS.

In this example we have particularly demonstrated the site-specific functionalization of immunoglobulins with biotin (IBA-biotin), fluorescein (IBA-FITC), iRGD cyclic peptide (IBA-iRGD), and paclitaxel (IBA-paclitaxel) using the UV-NBS photocrosslinking method. We identified UV energy, IBA-ligand concentration, immunoglobulin concentration, and buffer conditions to be key factors that impact the photocrosslinking efficiency. By manipulating these factors, we can control the specificity and the precise number of UV conjugations per immunoglobulin, establishing this method as an adaptable platform for numerous applications. Through an in-depth mass spectrometry analysis and detailed docking minimization, the precise location of the covalent bond formation was also determined and a mechanism of photocrosslinking was proposed.

Materials.

IBA, N,N-Diisopropylethylamine (DIEA), 1-fluoro-2,4-dinitrobenzene, N,N'-Dicyclohexyl carbodiimide (DCC), 4-(Dimethylamino)pyridine (DMAP), and paclitaxel were purchased from Sigma-Aldrich (St. Louis, Mo.). Streptavidin-HRP, HRP-conjugated IgG Fcγ specific goat anti-mouse, goat anti-rat and goat anti-human were purchased from Jackson ImmunoResearch (West Grove, Pa.). Heat shock isolated bovine serum albumin (BSA), mouse anti-FITC ($IgG^{FITC}$, clone: DE3), Amicon Ultra centrifugal filters (0.5 mL, 10K), Coomassie R-250, and C18 Ziptips were purchased from EMD Millipore (Billerica, Mass.). Amplex Red Assay Kit, rat anti-DNP ($IgG^{DNP}$, clone: LO-DNP-2), tissue culture grade L-glutamine, and β-mercaptoethanol were purchased from Invitrogen (Grand Island, N.Y.). RMPI-1640 media was purchased from Cell-Gro (Manassas, Va.). Hyclone Fetal Bovine Serum (FBS) and maleic anhydride amine reactive 96-well plates were purchased from Thermo Scientific (Rockford, Ill.). NovaPEG Rink Amide resin, Biotin NovaTag Resin, Fmoc-Cys(Trt)-Wang Resin, and all other amino acids were purchased from Novabiochem (Billerica, Mass.). Fmoc-N-amido-dPEG$_2$-acid was purchased from Quanta Biodesign (Powell, Ohio). Tris-gly running buffer, transfer buffer, and tris buffered saline (TBS) were purchased from Boston Bioproducts (Ashland, Mass.). IM9, U266, H929, and MM.1S cell lines were obtained from American Type Culture Collection (Rockville, Md.). L-glutamine, penicillin, and streptomycin were purchased from Gibco (Carlsbad, Calif.). Rituximab (chimeric human anti-CD20) was a gift from Dr. Rudolph Navari (Indiana University School of Medicine, South Bend, Ind.).

Photocrosslinking of IBA-Conjugated Ligands (IBA-Ligand) to Immunoglobulins.

The purity of both the immunoglobulin and the ligand being conjugated to the immunoglobulin were critical to determine the optimal conditions for UV conjugation. All immunoglobulins undergoing photocrosslinking were purchased as purified immunoglobulins with no protein stabilizers. Sodium azide, a very UV reactive preservative, and other small molecule additives were removed prior to UV exposure via membrane filtration. Immunoglobulins were incubated with the IBA-ligands for 1 h prior to UV exposure at room temperature (RT). Strict control over the UV energies delivered to the samples was achieved using a Spectroline UV Select Series Crosslinker from Spectronics at a wavelength of 254 nm at a fixed distance from the light source.

Synthesis of BSA-DNP and BSA-FITC.

BSA-DNP was synthesized in methanol and water by combining 20 molar equivalents of 1-fluoro-2,4-dinitrobenzene to 1 molar equivalent of BSA. BSA-FITC was synthesized in PBS by the addition of 20 molar equivalents of FITC. The reactions were carried out overnight at RT with continuous agitation. The products were purified with Amicon spin concentrators (10 kDa MW cutoff, Millipore) to remove unconjugated ligands and to exchange buffer to PBS pH 7.4. BSA-DNP product was analyzed by observing absorbance signals at 280 nm for BSA and at 350 nm for DNP. Similarly, BSA-FITC product was analyzed by observing the absorbance signals at 280 nm for BSA and at 494 nm for FITC. By comparing the absorbance values at the two wavelengths and using the extinction coefficients, we quantified the average number of BSA conjugations for both DNP and FITC.

Synthesis of Cyclic CD20 Mimotope.

Figure 10:
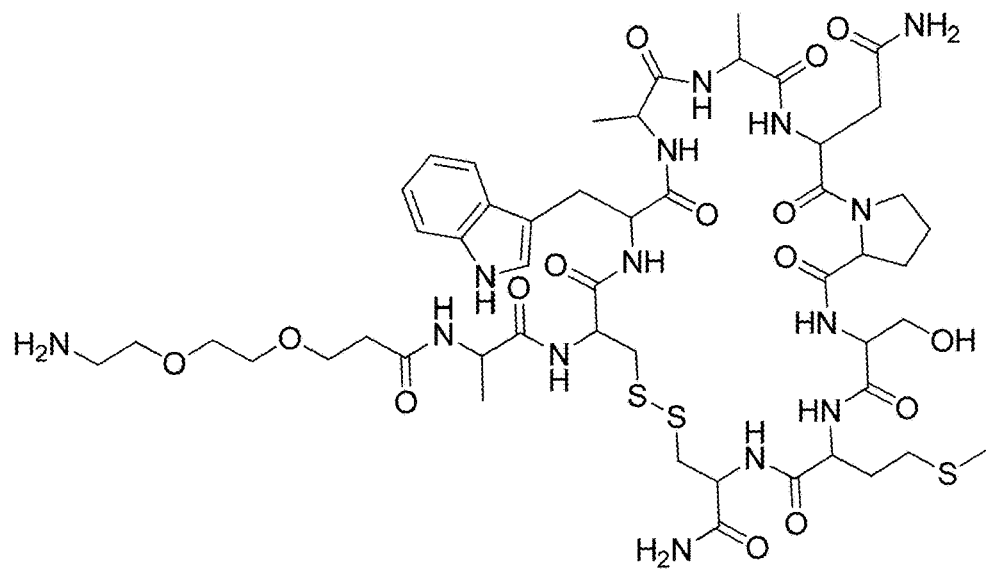
FIG. 10. The calculated exact mass for the cyclic CD20 mimotope ($C_{50}H_{76}N_{14}O_{15}S_3$) was 1208.48 Da; found 1209.50 Da. The cyclic CD20 mimotope synthesized for this study was purified via reverse phase HPLC on a Zorbax 300SB-C18 semi-preparative 9.4×250 mm 5-micron column with increasing acetonitrile as the mobile phase. The purified fractions were collected and mass verified via MALDI-TOF-MS on a Bruker Autoflex III mass spectrometer in reflectron mode. The samples were spotted in 2,5-dihydroxy benzoic acid (DHB) on a stainless steel MALDI target plate. The exact masses were calculated using ChemBioDraw Ultra (Version: 12.0.2.1076). Cyclization was also confirmed via MALDI-TOF-MS indicated by a loss of 2 Da [linear ($C_{50}H_{78}N_{14}O_{15}S_3$) found 1211.37 Da; cyclic ($C_{50}H_{76}N_{14}O_{15}S_3$) found 1209.50 Da]. The purity was confirmed using RP-HPLC on an analytical Zorbax C18 column (>95%), and the yield was 50%.

The cyclic CD20 mimotope for Rituximab binding was synthesized using standard solid phase synthesis protocols on a NovaPEG Rink Amide resin and Fmoc chemistry. The following residues were HBTU activated and coupled following Fmoc deprotection in the following order: Cys(Trt), Met, Ser(tBu), Pro, Asn(Trt), Ala, Ala, Trp(Boc), Cys(Trt), Ala, and N-amido-dPEG$_2$-acid. Kaiser tests were performed between coupling steps to monitor synthesis progress. The peptide was cleaved from the resin in 92.5% TFA, 2.5% TIS, 2.5% EDT, and 2.5% D.I. water, purified via RP-HPLC on a Zorbax C18 column, and characterized using MALDI-TOF MS (FIG. 10). The yield was 50%, and product purity was confirmed using RP-HPLC on an analytical Zorbax C18 column to be >95%. The peptide was cyclized overnight in DMF with DIEA and verified via MALDI-TOF MS.

Synthesis of IBA-Biotin.

Figure 11:
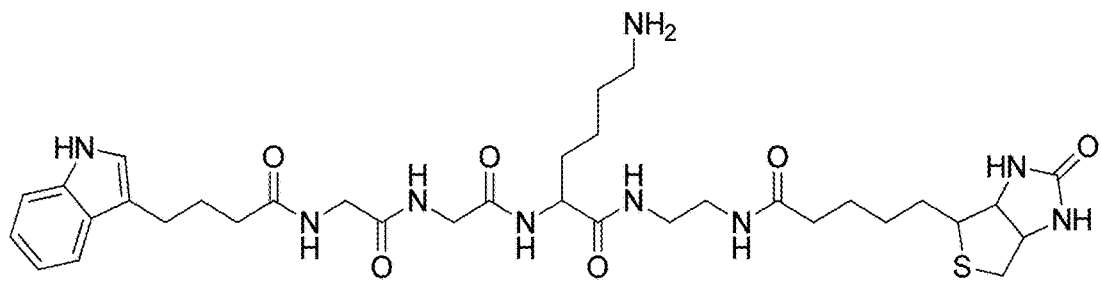
FIG. 11. The calculated exact mass for the IBA-biotin ($C_{34}H_{51}N_9O_6S$) was 713.37 Da; found 736.45 Da as the sodium adduct of IBA-biotin. The IBA-biotin molecule synthesized for this study was purified via reverse phase HPLC on a Zorbax 300SB-C18 semi-preparative 9.4×250 mm 5-micron column with increasing acetonitrile as the mobile phase. The purified fractions were collected and mass verified via MALDI-TOF-MS on a Bruker Autoflex III mass spectrometer in reflectron mode. The samples were spotted in 2,5-dihydroxy benzoic acid (DHB) on a stainless steel MALDI target plate. The exact masses were calculated using ChemBioDraw Ultra (Version: 12.0.2.1076). The purity was confirmed using RP-HPLC on an analytical Zorbax C18 column (>95%), and the yield was 60%.

IBA-Biotin was synthesized using standard solid phase synthesis protocols on a Biotin NovaTag Resin and Fmoc chemistry as described above. The following residues were coupled in order: Lys(Boc), Gly, Gly, IBA. IBA-biotin was cleaved from the resin in 95% TFA, 2.5% TIS, and 2.5% D.I. water, purified via RP-HPLC on a Zorbax C18 column, and characterized using MALDI-TOF MS (FIG. 11). The yield was 60%, and product purity was confirmed using RP-HPLC on an analytical Zorbax C18 column to be >95%.

Synthesis of IBA-FITC.

Figure 12:
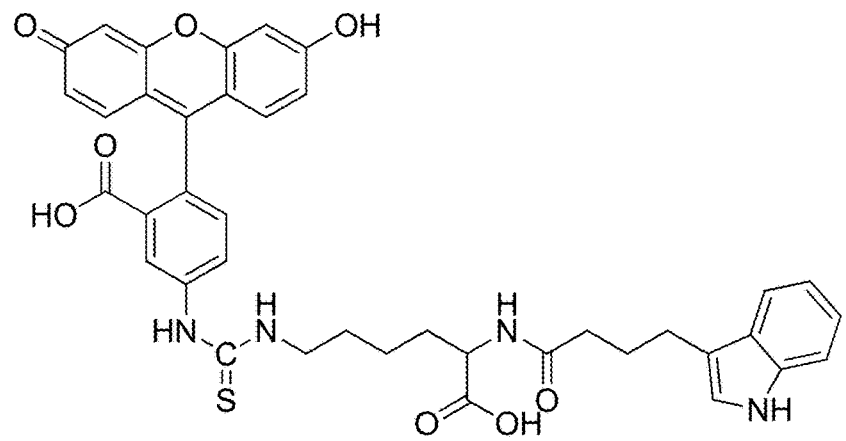
FIG. 12. The calculated exact mass for the IBA-FITC ($C_{39}H_{36}N_4O_8S$) was 720.22 Da; found 721.16 Da. The IBA-FITC molecule synthesized for this study was purified via reverse phase HPLC on a Zorbax 300SB-C18 semi-preparative 9.4×250 mm 5-micron column with increasing acetonitrile as the mobile phase. The purified fractions were collected and mass verified via MALDI-TOF-MS on a Bruker Autoflex III mass spectrometer in reflectron mode. The samples were spotted in 2,5-dihydroxy benzoic acid (DHB) on a stainless steel MALDI target plate. The exact masses were calculated using ChemBioDraw Ultra (Version: 12.0.2.1076). The purity was confirmed using RP-HPLC on an analytical Zorbax C18 column (>95%), and the yield was 75%.

IBA-FITC was synthesized by HBTU activation of IBA in DMF mixed in equimolar amounts of FITC and L-Lysine. The reaction was carried out overnight while shaking, purified via RP-HPLC on a Zorbax C18 column, and characterized using MALDI-TOF MS (FIG. 12). The yield was 75%, and product purity was confirmed using RP-HPLC on an analytical Zorbax C18 column to be >95%.

Synthesis of IBA-iRGD.

Figure 13:
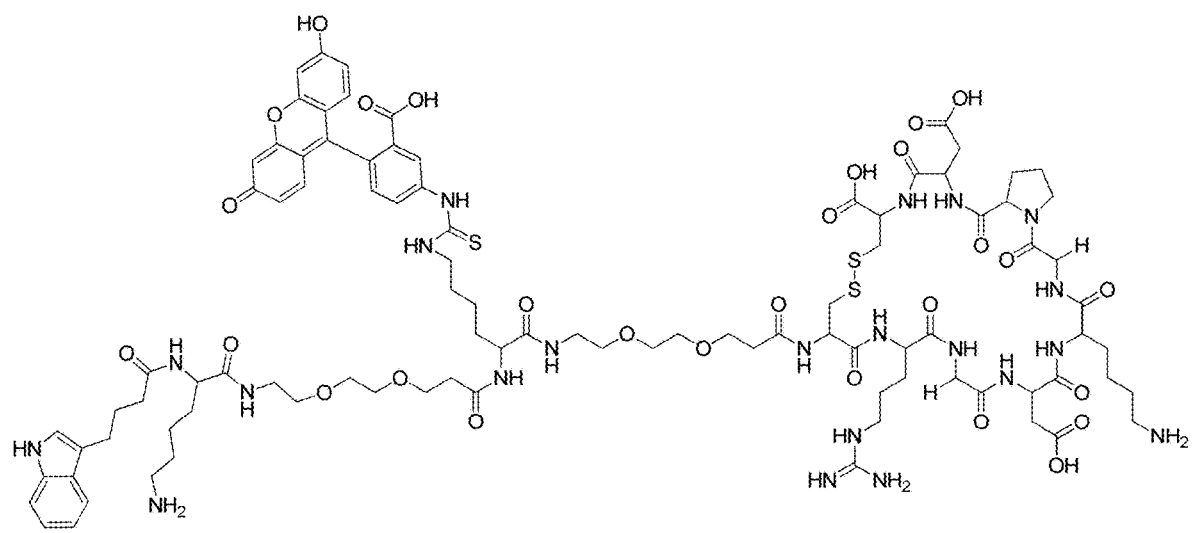
FIG. 13. The calculated exact mass for the cyclic IBA-iRGD ($C_{94}H_{129}N_{21}O_{28}S_3$) was 2095.85 Da; found 2096.42 Da. The IBA-iRGD molecule synthesized for this study was purified via reverse phase HPLC on a Zorbax 300SB-C18 semi-preparative 9.4×250 mm 5-micron column with increasing acetonitrile as the mobile phase. The purified fractions were collected and mass verified via MALDI-TOF-MS on a Bruker Autoflex III mass spectrometer in reflectron mode. The samples were spotted in 2,5-dihydroxy benzoic acid (DHB) on a stainless steel MALDI target plate. The exact masses were calculated using ChemBioDraw Ultra (Version: 12.0.2.1076). Cyclization was also confirmed via MALDI-TOF-MS indicated by a loss of 2 Da [linear ($C_{94}H_{131}N_{21}O_{28}S_3$) found 2099.27 Da; cyclic ($C_{94}H_{129}N_{21}O_{28}S_3$) found 2096.42 Da]. The purity was confirmed using RP-HPLC on an analytical Zorbax C18 column (>95%), and the yield was 40%.

The IBA-iRGD molecule was synthesized using standard solid phase synthesis protocols on a Fmoc-Cys(Trt)-Wang Resin and Fmoc chemistry as described above. The following residues were coupled in order: Asp(OtBu), Pro, Gly, Lys(Boc), Asp(OtBu), Gly, Arg(Pbf), Cys(Trt), N-amido-dPEG$_2$-acid, Lys(ivDde), N-amido-dPEG$_2$-acid, Lys(Boc), IBA. The ivDde protecting group was removed by 2% hydrazine in DMF. FITC was allowed to react for 3 h in DMF. The molecule was then cleaved from the resin in 92.5% TFA, 2.5% TIS, 2.5% EDT and 2.5% D.I. water, purified via RP-HPLC on a Zorbax C18 column, and characterized using MALDI-TOF MS (FIG. 13). The peptide was cyclized overnight in DMF with DIEA and cyclization was verified via MALDI-TOF MS. The yield was 40%, and product purity was confirmed using RP-HPLC on an analytical Zorbax C18 column to be >95%.

Synthesis of IBA-Paclitaxel.

Figure 14:
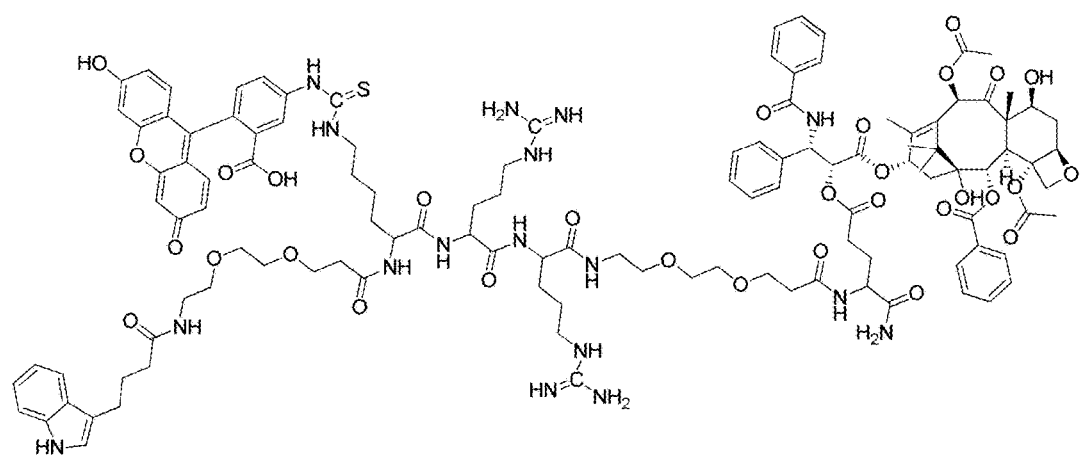
FIG. 14. The calculated exact mass for the IBA-paclitaxel ($C_{117}H_{143}N_{17}O_{31}S$) was 2313.99 Da; found 2315.67 Da. The IBA-paclitaxel molecule synthesized for this study was purified via reverse phase HPLC on a Zorbax SB-C3 semi-preparative 9.4×250 mm 5-micron column with increasing acetonitrile as the mobile phase. The purified fractions were collected and mass verified via MALDI-TOF-MS on a Bruker Autoflex III mass spectrometer in reflectron mode. The samples were spotted in 2,5-dihydroxy benzoic acid (DHB) on a stainless steel MALDI target plate. The exact masses were calculated using ChemBioDraw Ultra (Version: 12.0.2.1076). The purity was confirmed using RP-HPLC on an analytical Zorbax C18 column (>95%), and the yield was 50%.

The IBA-paclitaxel molecule was synthesized using standard solid phase synthesis protocols on a NovaPEG Rink Amide resin and Fmoc chemistry as described above. The following residues were coupled in order: Glu(OtBu), N-amido-dPEG$_2$-acid, Arg(Pbf), Arg(Pbf), Lys(ivDde), N-amido-dPEG$_2$-acid, IBA. The ivDde protecting group was removed by 2% hydrazine in DMF and FITC was allowed to react for 3 h in DMF. The molecule was then cleaved from the resin in 95% TFA, 2.5% TIS, and 2.5% D.I. water, purified via RP-HPLC on a Zorbax C18 column, and characterized using MALDI-TOF MS (FIG. 14). The resulting acid containing molecule was then activated with 2 equivalents of DCC, 1 equivalent of DMAP in DMF, and was added to 1 equivalent of Paclitaxel. After the reaction was carried out overnight at RT, the DMF was rotate evaporated. The molecule was purified via RP-HPLC on a Zorbax C3 column, and characterized using MALDI-TOF MS. The yield was 50%, and product purity was confirmed using RP-HPLC on an analytical Zorbax C18 column to be >95%.

Assessing Antigen Binding Activity, Fc Stability, and Biotinylation of the Immunoglobulin Via ELISA.

Figure 15:
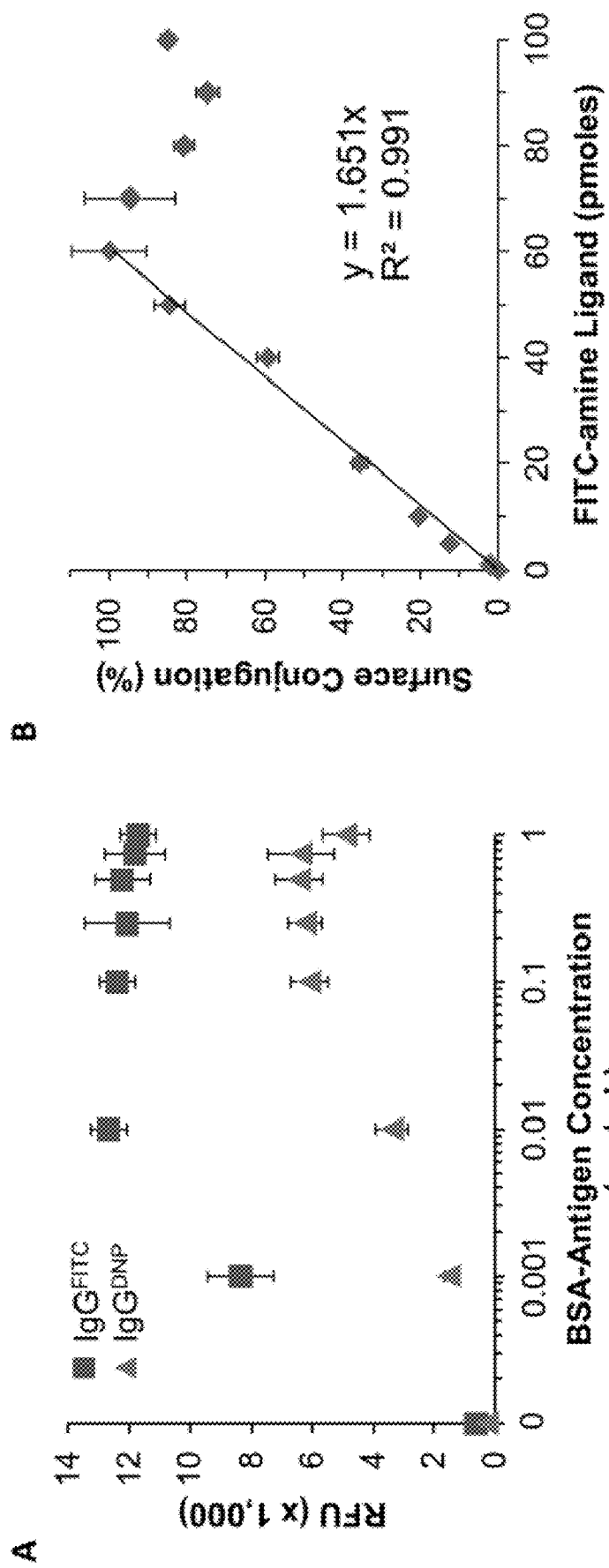
FIG. 15. A) Optimum concentration of BSA-DNP and BSA-FITC in 100 µL of pH 9.6 carbonate-bicarbonate coating buffer when incubated on a high bind ELISA plate. Increasing the antigen concentration while keeping the primary and secondary immunoglobulin concentrations constant results in a plateau for both $IgG^{FITC}$ and $IgG^{DNP}$ above 0.1 mg/mL BSA-antigen concentrations. It is important to note that the intensity of the secondary immunoglobulin for $IgG^{DNP}$ (rat immunoglobulin) is half that of $IgG^{FITC}$ (mouse immunoglobulin) when administered at the same concentration with the same enzymatic reaction time of 20 min. B) Conjugation efficiency of a FITC-amine ligand to a maleic anhydride amine reactive surface to determine optimal CD20 cyclic mimotope incubation for the antigen specific ELISA using Rituximab. To measure the percent surface conjugation, FITC-amine (FIG. 27) was synthesized and reacted with a maleic anhydride plate in 100 µL of PBS buffer at pH 8.0 for 2 h at room temperature (RT). The plate was washed with 6 cycles of 200 µL PBS 0.05% Tween 20 and fluorescence was measured to determine relative plate coating (ex. 494 nm em. 518 nm). The highest yield was achieved at ~62.5 pmoles of FITC-amine. This concentration was used for coating with the cyclic CD20 mimotope for the experiments described in this study. All data represents means (±SD) of triplicate experiments.

Antigen coated ELISA plates for (Rituximab, IgG$^{DNP}$ and IgG$^{FITC}$) were generated by adsorbing BSA-DNP or BSA-FITC (0.1 mg/mL) to high binding 96-well ELISA plates in 0.05 M carbonate-bicarbonate coating buffer at pH 9.6 for 2 hour at RT. Antigen coated ELISA plates for Rituximab were generated by covalently reacting the cyclic CD20 mimotope (60 pmoles) to a maleic anhydride amine reactive plate surface in PBS pH 8.0 for 2 hour at RT and any remaining reactive sites were then quenched using 50 mM Tris buffer with 100 mM NaCl at pH 8.0 for 1 h (FIG. 15). All plate surfaces were then blocked with BSA blocking buffer (100 µL of 5% BSA in PBS pH 7.4 with 0.1% Tween 20) for 1 hour. Each immunoglobulin (Rituximab, IgG$^{DNP}$, IgG$^{FITC}$) was exposed to UV in the presence or absence of IBA-biotin and were then incubated in the respective antigen coated plates. The plates were washed to remove any unbound components using an automated plate washer (three cycles of 200 µL PBS with 0.05% Tween 20 at pH 7.4). In an alternate assay, immunoglobulin exposed to UV energy in the presence or absence of IBA-biotin was directly adsorbed to a high binding 96-well ELISA plate in 0.05 M carbonate-bicarbonate coating buffer at pH 9.6 for 2 h at RT. In both assays, the wells were incubated with a 1:5,000 dilution of HRP-anti-Fc immunoglobulin (1.0 mg/mL stock) in BSA blocking buffer for 1 h to quantify the total amount of surface bound immunoglobulin (active Fc). To assess the degree of biotinylation for each sample, the wells were incubated with a 1:10,000 dilution of streptavidin-HRP (1.0 mg/mL stock) in BSA blocking buffer for 1 h. Amplex red, the HRP substrate, was added and fluorescent product formation was observed on a Molecular Devices SpectraMax M5 plate reader (ex. 570 nm, em. 592 nm). Control experiments performed without IBA-biotin were used as background for the biotin detection measurements. The results are reported as relative fluorescence units (RFU). All data represents means (±SD) of triplicate experiments.

Determination of Average Number of UV Conjugations Via Size Exclusion Chromatography (SEC).

Figure 16:
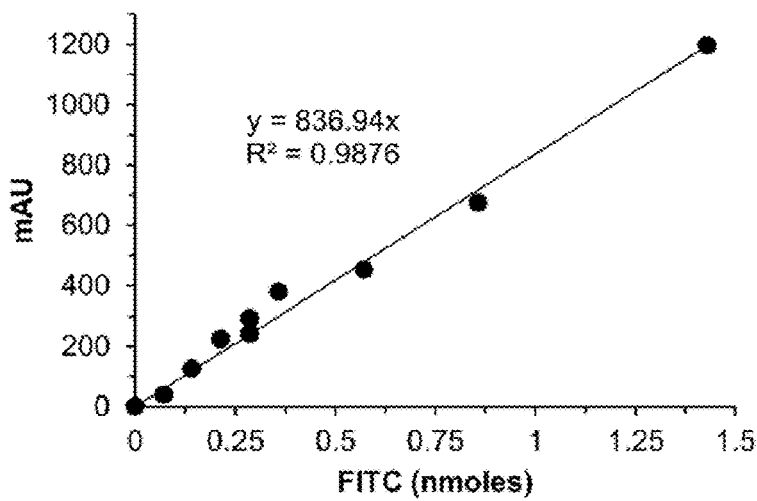
FIG. 16. FITC calibration curve to convert 494 nm peak integrations to nmoles of FITC when conjugated to Rituximab and $IgG^{DNP}$. Using this calibration curve, the average number of IBA-FITC conjugations to the immunoglobulin was determined in the presence of various concentrations of ligand and over a range of UV energies and buffer conditions. Each SEC run was achieved using a 25 min isocratic gradient of 50 mM sodium phosphate buffer at pH 6.8 with 370 mM NaCl and 0.1% Tween 20 on a Tosoh Biosciences $G4000SW_{XL}$ size exclusion column. Briefly, a known amount of FITC was injected on column and the elution peak was integrated using Agilent Chemstation LC software. The peak integrations were then plotted and fit by linear regression to produce the final calibration curve.

A Tosoh Biosciences G4000SW$_{XL}$ (7.8 mm ID×30 cm) size exclusion column was used to assess the average number of IBA-FITC conjugations to the immunoglobulin in the presence of various concentrations of ligand and over a range of UV energies and buffer conditions. Immunoglobulin samples were prepared as indicated, and 20 µL of each sample were analyzed on the SEC column. Each SEC run was achieved using a 25 min isocratic gradient of 50 mM PBS at pH 6.8 with 370 mM NaCl and 0.1% Tween 20. All samples were analyzed at 220 and 280 nm to detect immunoglobulin content and at 494 nm to detect covalently bound IBA-FITC. Each absorbance spectrum was integrated on Chemstation LC software and used to calculate total immunoglobulin content and total nmoles of covalently bound IBA-FITC compared to a calibration curve to determine the average number of IBA-FITC conjugations per immunoglobulin (FIG. 16).

Western Blot Analysis for Determination of the Photocrosslinking Site.

Immunoglobulin (Rituximab, IgG$^{DNP}$ and IgG$^{FITC}$) at 20 µM was incubated with excess IBA-biotin (300 µM) in PBS buffer at pH 7.4 and exposed to the indicated amount of UV energy. The samples were run on a 10% SDS-PAGE gel with a tris-glycine running buffer under reducing conditions at 110 V for 1 h and were transferred to a nitrocellulose membrane at 110 V for 90 min in a 10% MeOH transfer buffer. The membrane was blocked with 10% dry milk in TBS for 1 h and was then blotted with 1:10,000 dilution of streptavidin-HRP for 1 h at RT. A chemiluminescent HRP substrate was used to detect the location where IBA-biotin was covalently conjugated to the immunoglobulin. To verify transfer of all protein content to the membrane, both the SDS-PAGE gel (post transfer) and nitrocellulose membrane were coomassie blue stained in a solution of 10% acetic acid, 20% methanol, 0.15% Coomassie R-250 for 30 min and destained in a solution of 20% acetic acid, 20% methanol, 60% D.I. water for 1.5 h. Control experiments performed in the absence of UV exposure, or in the absence of IBA-biotin did not yield any detectable bands. Similarly, control experiments performed with only biotin did not yield any detectable bands.

Immunoglobulin Digestion and Mass Spectrometry Analysis for Determination of the Photocrosslinking Site.

Briefly, the immunoglobulins were reduced with DTT and alkylated with iodoacetamide. The immunoglobulin was exchanged into 1% formic acid (FA) for the pepsin digestion, digested for 3 h, a portion quenched, then digested overnight and pooled. The trypsin-digest fraction was proteolyzed in a 50 mM ammonium bicarbonate buffer. After digestion, samples and controls were quenched, dried and desalted using micro C18 Ziptips, according to manufacturer's instructions. Approximately 1 µg of each digest was analyzed by Nano UHPLC/MS/MS. Separation was performed over a 60 min gradient from 5-35% acetonitrile (0.1% FA) on a 100 µm×100 mm C18 BEH column (Waters) running at 700 nL/min. Acquisition was performed on an LTQ-Velos Orbitrap mass spectrometer running a TOP8 data dependent mode acquisition as described previously. Peak lists were generated using the RAW2MSM script from the Mann Lab and database searching was performed using Protein Pilot (AB Sciex) against a custom database containing Rituximab, common contaminants, and the FASTA sequence of yeast. In order to generate a likelihood of matching a stochastic modification, all search parameters were set to Thorough, Mods, and Biological Substitutions. This enabled the appropriate peptide to be identified and then manually sequenced to confirm the UV-conjugated modification.

Docking Minimization of IBA in the Rituximab NBS.

The modeling software used to perform the minimization was MOE (version 2011.10, Chemical Computing Group, Montreal, Canada). Crystallographic water molecules were removed from the X-ray crystal structure of Rituximab (PDB: 2OSL), then protonated using the Protonate3D module in MOE and AMBER99 to assign partial charges to receptor atoms. IBA was constructed using the Builder module in MOE. Protons were assigned, and AM1-BCC partial charges were computed for the ligand atoms. The MOE Dock module was used to generate a proposed binding mode of IBA to the NBS. The top-ranking ligand binding mode from the docking was minimized with the MOE Energy Minimize method, employing Steepest Descents, Conjugate Gradient, and Truncated Newton until the system converged (gradient <0.05). All receptor atoms were held in place with a fixed potential, and only the residues on the loop defined by Phe35-Pro45 were unfixed and allowed to move, to model any induced-fit of the receptor due to the binding of the IBA ligand.

Utilization of the UV-NBS Method for Flow Cytometry Applications.

IM9, U266, H929, and MM.1S cell lines were cultured in RPMI 1640 media containing 10% FBS, 2 mM L-glutamine, 100 U/mL penicillin, and 100 µg/mL streptomycin. IM9 served as a CD20 positive cell line, and all others were used as negative controls (as determined by Rituximab staining followed by a FITC-labeled secondary immunoglobulin, results not shown). IBA-FITC was photocrosslinked to Rituximab at the indicated UV energies. All cell lines were used at a density of 0.5×10$^6$ cells/mL in blocking buffer (1.5% BSA in PBS pH 7.4) and initially incubated for 30 min on ice. IBA-FITC photocrosslinked Rituximab was incubated with the cells on ice for 1 h at a final concentration of 200 nM. Samples were washed three times and analyzed on a Guava easyCyte 8HT flow cytometer.

Results and Discussion.

Optimization of UV Energy for Photocrosslinking of Functional Ligands to Immunoglobulins Via the UV-NBS Method.

Several parameters such as UV energy exposure, IBA-ligand concentration, immunoglobulin concentration, and buffer conditions are important factors effecting the optimization of the UV-NBS method for efficient photocrosslinking at the NBS. The amount of UV energy has to be sufficiently high to promote maximum crosslinking of the IBA without causing damage to the immunoglobulin such that the antigen binding and Fc related functions are preserved. The IBA-ligand and immunoglobulin concentrations are critical since the site-specific photocrosslinking is dependent on the non-covalent association between the IBA and NBS prior to UV exposure. The IBA-ligand concentration must be sufficiently high that all NBS are occupied by an IBA-ligand but not so high as to promote non-specific coupling to the immunoglobulin as a result of weak non-specific interactions. The buffer conditions also play a crucial role in the crosslinking efficiency by affecting the binding interactions between the IBA-ligand and NBS, as well as by enhancing or reducing photo-reactivity of the IBA since UV coupling can be highly dependent on pH. These parameters are assessed in greater detail throughout this manuscript providing for a nearly universal site-specific photocrosslinking method applicable to all immunoglobulins.

We first evaluated the effect of UV energy on IBA photocrosslinking to the immunoglobulin by using IBA-biotin. IBA-biotin was photocrosslinked to the immunoglobulin by first incubating Rituximab, IgG$^{DNP}$ or IgG$^{FITC}$ immunoglobulins (20 µM) with saturating concentrations of IBA-biotin (300 µM) in PBS pH 7.4 to allow for the non-covalent association between IBA and the NBS. The saturating concentration of IBA-biotin for the NBS was estimated to be >100 µM based on the previously reported $K_d$ for IBA/NBS interactions (1-8 µM). The samples were then exposed to increasing amounts of UV energy, from 0 to 10 J/cm$^2$, to enable IBA-biotin photocrosslinking at the NBS. The photocrosslinking efficiency was determined via an ELISA assay, where the IBA-biotin photocrosslinked immunoglobulins were incubated on plate surfaces coated with their respective antigens, and the degree of immunoglobulin biotinylation was determined using HRP conjugated streptavidin (see description below).

By modulating UV energy exposure, we found that increasing UV energy results in increased IBA-biotin photocrosslinking efficiency to the immunoglobulin, reaching a maximum at ~0.5 J/cm$^2$ (FIG. 2A). This maximum is maintained until ~5.0 J/cm$^2$ UV energy at which point there is a decline in the signal intensity presumably due to decreased antigen binding activity caused by UV damage to the immunoglobulin CDR. While the three immunoglobulins tested (Rituximab, IgG$^{DNP}$, and IgG$^{FITC}$) show similar trends, it is important to note that the effects of UV exposure depends upon the amount of UV sensitive amino acid residues that are present in the CDR that directly contribute to antigen binding. Therefore, the results we obtained represent the photocrosslinking efficiency combined with the antigen binding activity of the immunoglobulin. To confirm these results, we used another assay where the UV-exposed, IBA-biotin photocrosslinked immunoglobulins were directly adsorbed to a high binding ELISA plate, rather than binding to an antigen coated surface. The degree of immunoglobulin biotinylation was again detected using an HRP conjugated streptavidin. This assay also yielded very similar results, with IBA-biotin photocrosslinking efficiency reaching a maximum and a plateau at ~0.5 J/cm$^2$ (FIG. 2B). Based on these two ELISA assays, we determined 0.5-5.0 J/cm$^2$ to be an effective UV exposure that can be used for photocrosslinking of IBA-conjugated functionalities to immunoglobulins via the NBS, without damaging the antigen binding site. It is noteworthy that the plateau observed in these assays suggests the presence of a specific conjugation site on the immunoglobulin that becomes saturated with increasing UV energy, indicating that the photocrosslinking takes place at the NBS. If IBA-biotin was nonspecifically photocrosslinking to the immunoglobulins, it would be expected that the total biotinylation would continually rise with increasing UV energy.

Effect of IBA-Ligand Concentration on Photocrosslinking Efficiency.

Figure 2:
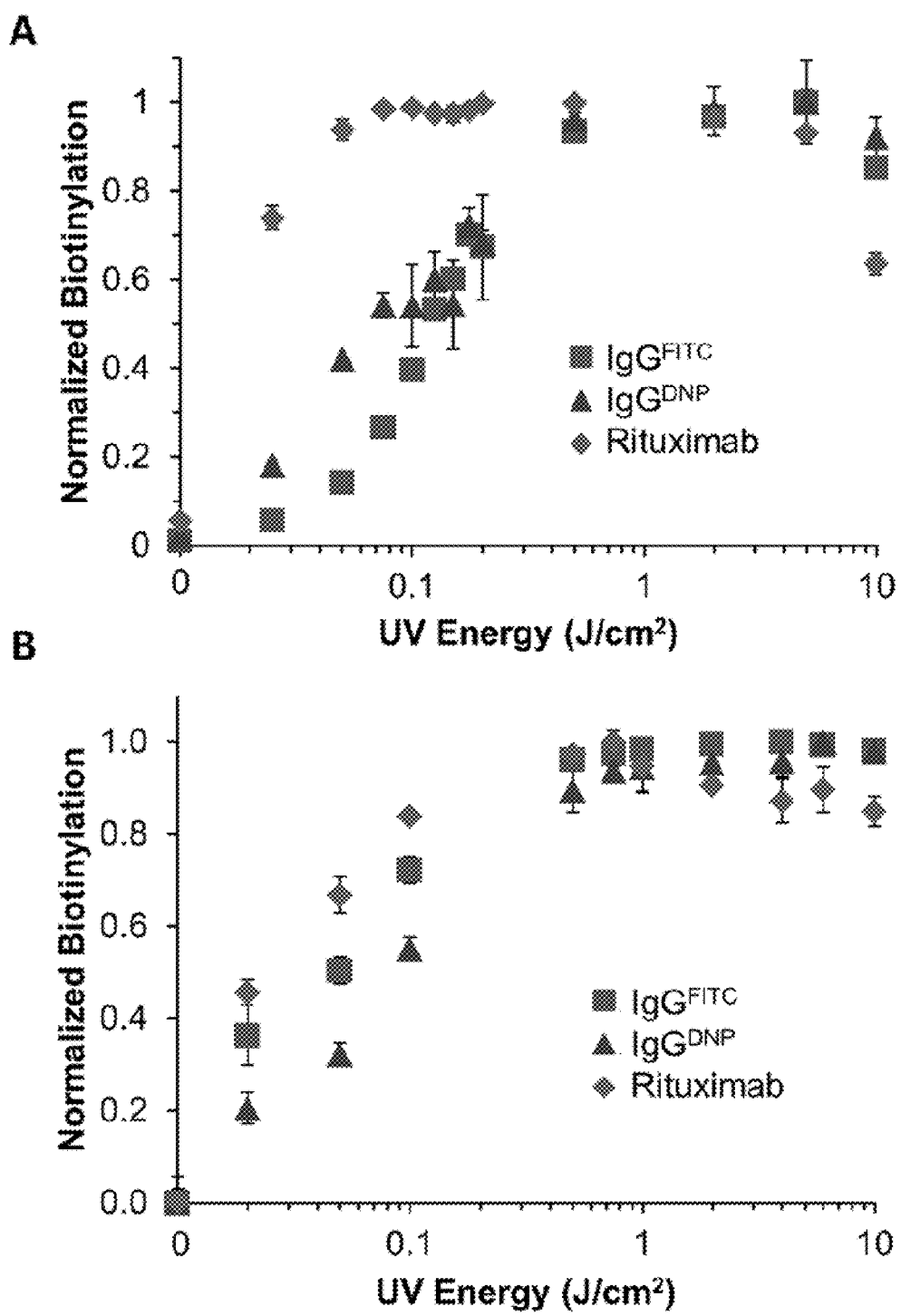
FIG. 2. A) Photocrosslinking efficiency of the IBA-biotin to the immunoglobulin at the NBS was determined by an indirect ELISA assay, where the total biotinylation levels of the indicated immunoglobulins (Rituximab, IgG$^{DNP}$, IgG$^{FITC}$) were detected after binding to their respective surface immobilized antigens. B) Photocrosslinking efficiency of the IBA-biotin to the immunoglobulin at the NBS was determined by directly adsorbing the biotinylated immunoglobulins to a high binding ELISA plate surface and evaluating the total biotinylation. In both cases streptavidin-HRP was used to assess the degree of biotinylation. All data represents means (±SD) of triplicate experiments.
Figure 3:
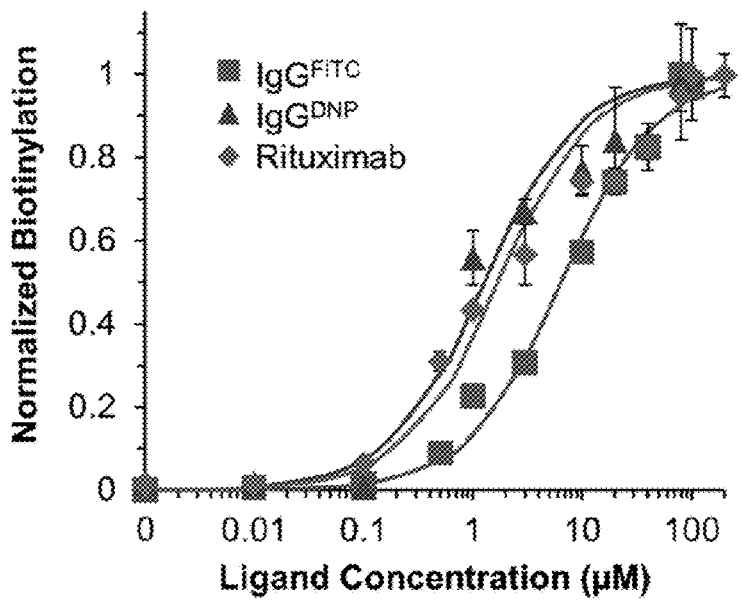
FIG. 3. Effect of ligand concentration on the photocrosslinking efficiency by the UV-NBS method. The indicated immunoglobulins were incubated with increasing concentrations of IBA-biotin and exposed to 1 J/cm$^2$ UV. IBA-biotin photocrosslinking efficiency at the NBS was determined by directly adsorbing the biotinylated immunoglobulins to a high binding ELISA plate surface and using streptavidin-HRP as a reporter. All data represents means (±SD) of triplicate experiments.

The IBA-ligand concentration plays a critical role in the efficiency of photocrosslinking since it determines the extent to which all NBS are bound to IBA prior to UV exposure. To assess the role that IBA-ligand concentration plays in crosslinking efficiency, an ELISA study was conducted in which the immunoglobulin concentration (20 µM) and the amount of UV energy exposure (1.0 J/cm$^2$) were held constant while the ligand, IBA-biotin, concentration was varied from 0-200 µM. For this analysis, a UV energy of 1.0 J/cm$^2$ was selected since this UV energy demonstrated efficient photocrosslinking without any reduction in antigen recognition or Fc damage to the immunoglobulins (FIG. 2). The IBA-biotin photocrosslinked immunoglobulins were adsorbed to high binding ELISA plates and HRP-streptavidin was used as the reporter to assess the degree of immunoglobulin biotinylation. Increasing the ligand concentration resulted in an increase in the UV crosslinking efficiency reaching a plateau at ~100 µM, as can be observed in FIG. 3. The curves were then fit to a sigmoid and an EC$_{50}$ (half maximum effective concentration) value was determined (FIG. 3). The EC$_{50}$ values for Rituximab, IgG$^{DNP}$ and IgG$^{FITC}$ were 1.7, 1.3 and 6.4 µM, respectively. While EC$_{50}$ do not directly correlate with dissociation constants ($K_d$), the EC$_{50}$ values reported here are very similar to the previously established $K_d$ values determined for IBA/NBS interactions (1-8 µM). Based on the similar trends observed between these assays, as well as the experimentally established ligand concentrations that yielded ~100% crosslinking at all NBS sites, we have determined that an IBA-ligand concentration of ≥100 µM enables maximum photocrosslinking efficiency.

Effect of UV Energy and IBA-Ligand Concentration on the Number of Conjugations Per Immunoglobulin.

For certain applications that require quantitative analysis, it is imperative to determine the average number of functional ligands conjugated to each immunoglobulin. When utilizing the UV-NBS photocrosslinking method we anticipate a maximum of two IBA-ligand conjugations per immunoglobulin as there are two NBS per immunoglobulin. Control over the number of photocrosslinked ligands via the UV-NBS method can be achieved by tuning conditions such as the amount of UV energy and the concentration of both the immunoglobulin and IBA-ligand to drive a particular outcome. To evaluate the effect of these parameters on the average number of ligands conjugated per immunoglobulin via the UV-NBS method, SEC was used. For quantification purposes, IBA-FITC was used as the ligand since FITC has a maximum absorbance at 494 nm, which is well outside the range of typical protein adsorption.

Figure 4:
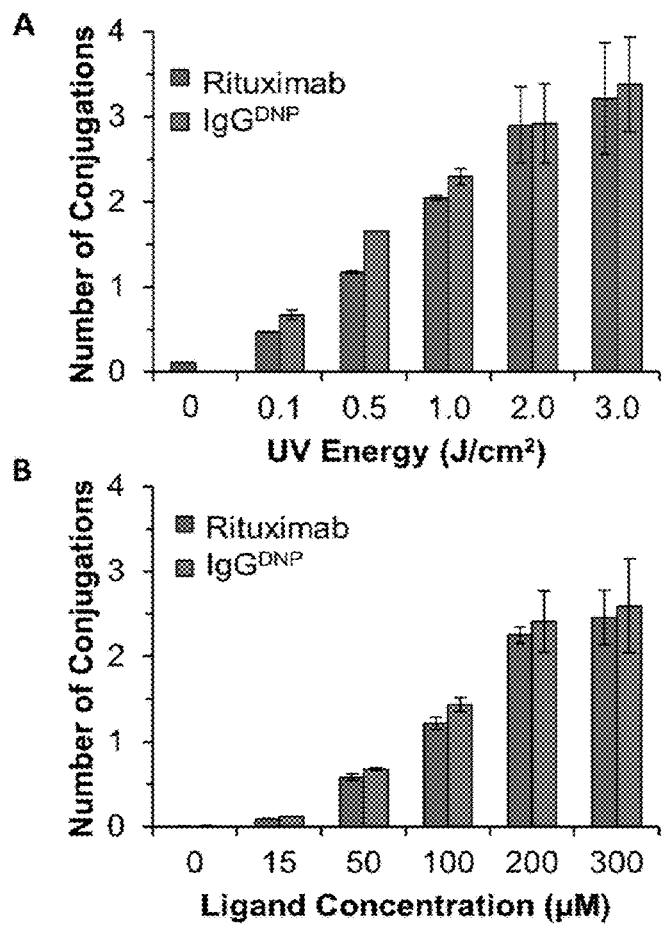
FIG. 4. A) The effect of UV energy on the average number of IBA-FITC conjugations per immunoglobulin at fixed ligand and immunoglobulin concentrations of 300 µM and 20 µM, respectively. B) The effect of IBA-FITC ligand concentration on the average number of conjugations at a constant immunoglobulin concentration (20 µM) and 1 J/cm$^2$ UV energy exposure. Number of conjugations was determined from absorbance at 494 nm SEC peak integrations. All data represents means (±SD) of triplicate experiments.
Figure 17:
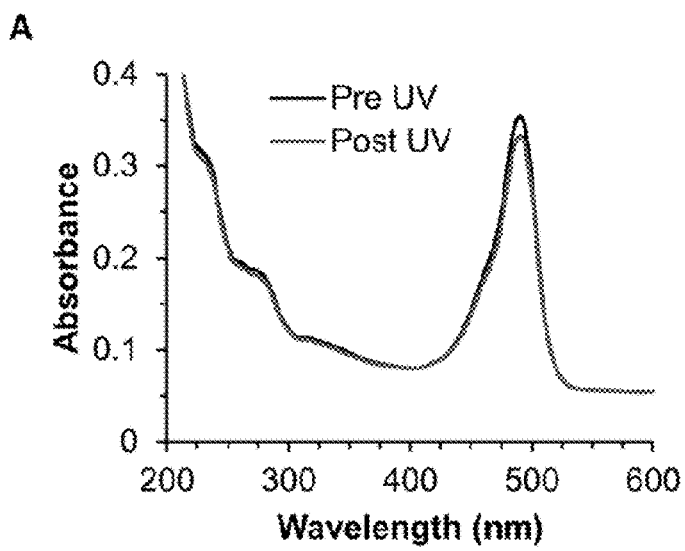
FIG. 17. A) Absorbance scans of IBA-FITC (200-600 nm) in PBS before and after 2 $J/cm^2$ UV exposure. B) Fluorescence emission scans of IBA-FITC before and after 2 $J/cm^2$ UV exposure at a constant excitation wavelength of 494 nm. There is a minimal impact to both the FITC absorbance at 494 nm and emission spectra as a result of UV exposure at 254 nm.
Figure 17:
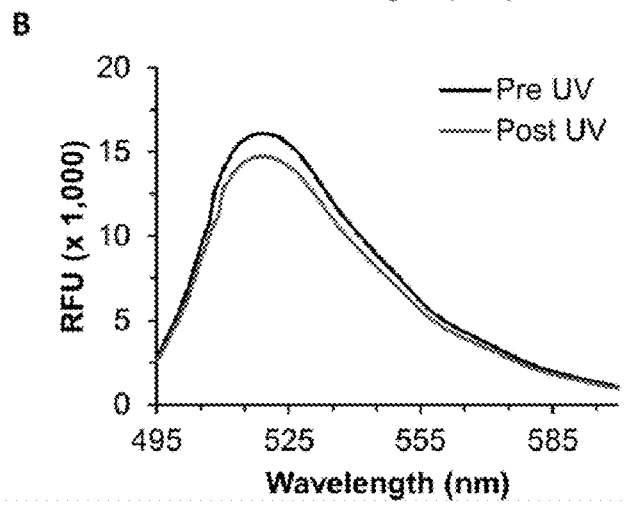
Figure 18:
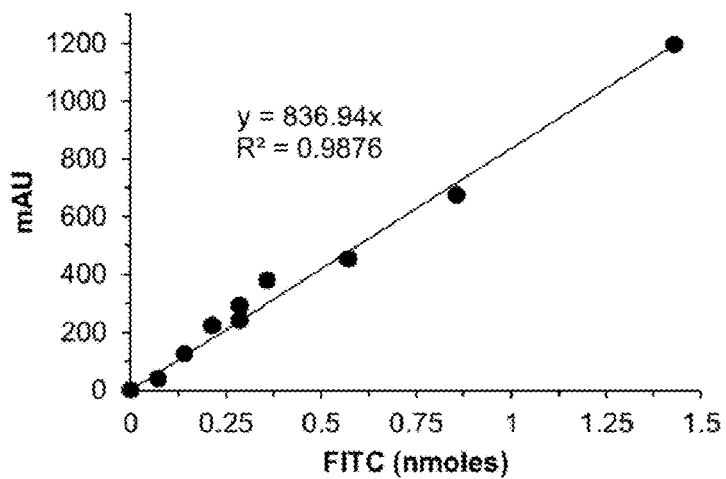
FIG. 18. Absorbance scan of IBA-FITC in PBS (trace that includes the left peak), fixed 254 nm excitation with fluorescence emission scan (trace that includes the lowest of the three peaks), and fixed 494 nm excitation with fluorescence emission scan (trace that includes the right peak). This data demonstrates that 254 nm, the wavelength used in the photocrosslinking reactions, is not sufficiently high to excite the FITC to result in damage to the fluorophore or for any significant photo bleaching to occur.

The effect of UV energy on the average number of IBA conjugations per immunoglobulin was evaluated first by incubating IBA-FITC at 300 µM, a concentration that promoted complete association with the immunoglobulin, and was then exposed to the indicated UV energy (FIG. 4A). The IBA-FITC conjugated immunoglobulin was then injected on an SEC column where non-conjugated IBA-FITC ligand eluted separately from the conjugated and non-conjugated immunoglobulin. We generated a calibration curve for FITC (494 nm, FIG. 16) and immunoglobulin (220 and 280 nm), to determine the average number of IBA-FITC conjugations per immunoglobulin (FIG. 4A). As expected there was an average of two covalent conjugations at 1 J/cm$^2$ UV energy. This was the anticipated maximum number of conjugations per immunoglobulin and 1 J/cm$^2$ was also determined to be the UV energy level that yielded the maximum crosslinking efficiency while retaining overall immunoglobulin binding activity (FIG. 2). As UV energy was increased, the number of conjugates increased with a maximum of 3 total conjugations per immunoglobulin at 3.0 J/cm$^2$ UV exposure. These are likely caused by an increase in the number and diversity of UV activated radical-IBA moieties resulting in non-site-specific conjugations. Importantly, the number of non-specific conjugations remains low, i.e., ≤1 at 3 J/cm$^2$, due to the short life span of the UV activated IBA radical. The specific photocrosslinking reaction between the NBS and IBA-ligand occurs much more rapidly than the non-specific photocrosslinking due to the proximity of the IBA to reactive moieties when bound to the NBS and the enhanced photo reactivity of the aromatic rich NBS. No crosslinking was observed in the absence of IBA or in the absence of UV energy, as expected. The 254 nm UV exposures to initiate photocrosslinking between the IBA and the immunoglobulin had minimal impact on the adsorption or fluorescence profile of the conjugated FITC at the UV energy levels used throughout these experiments (FIGS. 17 and 18).

Figure 20:
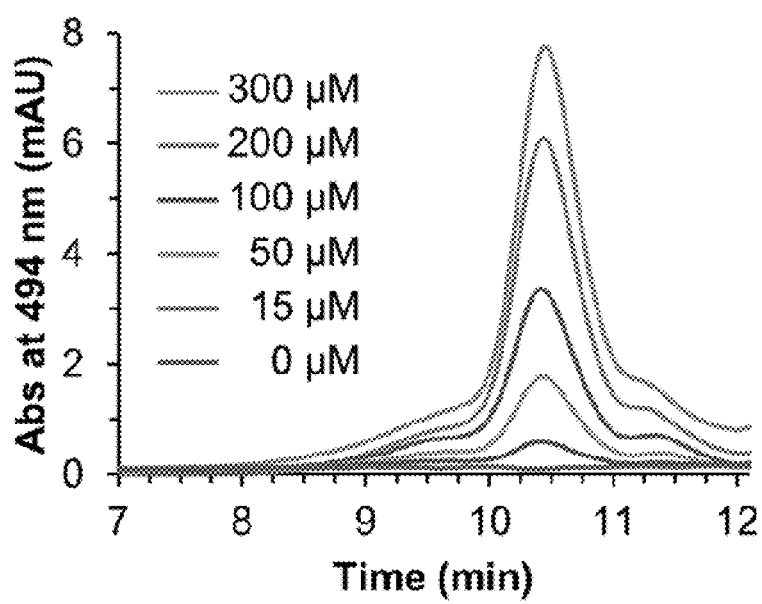
FIG. 20. SEC chromatograms (494 nm absorbance wavelength) demonstrating the effect of IBA-FITC concentration on the average number of conjugations to $IgG^{DNP}$ at a constant immunoglobulin concentration (20 µM) and constant UV energy exposure of 1 $J/cm^2$. The elution peaks were integrated and correlated to a calibration curve to determine the nmoles of FITC (FIG. 16) and was divided by the nmoles of immunoglobulin injected on the column indicated by peak integrations at 220 and 280 nm providing for a straight forward method of quantifying the average number of IBA-FITC conjugations per immunoglobulin. These 494 nm traces represent the raw data for FIG. 4B ($IgG^{DNP}$) in example 1.

In a separate experiment, we evaluated the effect of IBA-ligand concentration on the number of conjugations to the immunoglobulin by carrying out SEC analysis. For this assay the UV energy was kept constant at 1 J/cm$^2$ while the IBA-FITC ligand concentration was varied from 0 to 300 µM. With increasing ligand concentration, the fraction of NBS occupied with IBA increased, which resulted in an increase in the average number of covalent conjugations upon UV exposure. The number of conjugations approached 2 conjugations at 100 µM ligand concentration and reached a plateau at ~2 conjugations per immunoglobulin at a 200 µM ligand concentration (FIG. 4B). At very high ligand concentrations (>500 µM), we observed a marked increase in non-specific UV photocrosslinking, likely resulting from weak hydrophobic interactions of the IBA-ligand with the immunoglobulin surface (FIG. 19A). The SEC chromatograms (494 nm) for IgG$^{DNP}$ at varying IBA-ligand concentrations can be found in FIG. 20. A summary of the average number of UV conjugations can also be found in Tables 1 and 2 above. Taken together, our results demonstrated that to facilitate efficient and specific photocrosslinking of an IBA-ligand to the NBS, the IBA-ligand concentration must range between 100-400 µM with an immunoglobulin to IBA-ligand ratio between 1:10-1:20.

Effect of UV Energy on Immunoglobulin Binding Activity and Fc Recognition.

UV exposure is an essential step in photocrosslinking of functional groups to immunoglobulins via the UV-NBS method. However, too much UV exposure has potentially damaging effects to the immunoglobulin's structure, which may lead to: i) loss in the immunoglobulin's ability to recognize its antigen, and/or ii) loss in Fc domain recognition by a secondary immunoglobulin. To ensure that the UV energies necessary to initiate covalent bond formation did not render the immunoglobulin inactive, we evaluated the effect of UV energy on immunoglobulin activity and Fc recognition. Rituximab, IgG$^{DNP}$ and IgG$^{FITC}$ were exposed to increasing UV energies in the presence of 300 µM IBA-biotin and evaluated for their antigen binding activity as well as their recognition by Fc-specific secondary immunoglobulins. For this assay, the respective antigens for each immunoglobulin were first immobilized onto an ELISA plate surface through either physical adsorption (BSA-FITC, BSA-DNP) or covalent lysine side chain immobilization (cyclic CD20 mimotope). Next, the UV-exposed, IBA-biotin photocrosslinked immunoglobulins were incubated on the antigen-coated plates and allowed to bind to their respective antigens. To assess immunoglobulin antigen binding activity and Fc recognition simultaneously, an HRP conjugated secondary immunoglobulin specific for the Fc was used with a fluorescent amplex red substrate to determine the total amount of surface-bound active immunoglobulin. Our results demonstrated no observable effect on immunoglobulin structure up to a UV energy of 2.0 J/cm$^2$, with only a slight decrease in the signal intensity at greater UV energies (FIG. 5A). With the exception of IgG$^{DNP}$, both Rituximab and IgG$^{FITC}$ maintained a greater than 87% immunoglobulin activity at 5 J/cm$^2$, well above the necessary UV energy to facilitate efficient photocrosslinking at the NBS.

In an alternative assay, we evaluated the effect of UV exposure on Fc structural integrity of IBA-biotin photocrosslinked immunoglobulins by directly adsorbing them to high binding ELISA plates and then using an anti-Fc secondary immunoglobulin as a reporter (FIG. 5B). Our results demonstrated no detectable damage to the Fc domains of IgG$^{DNP}$ and IgG$^{FITC}$ at UV energies of 1.0 J/cm$^2$, while Rituximab retained Fc activity through 4.0 J/cm$^2$, all values well within the necessary UV energies to achieve efficient photocrosslinking. It is noteworthy that in both assays, IgG$^{DNP}$ demonstrated reduced Fc recognition with ~75% activity at 2.0 J/cm$^2$, significantly lower when compared to Rituximab and IgG$^{FITC}$. The most likely cause for the increased sensitivity of IgG$^{DNP}$ to UV exposure is a result of damage to the Fc domain, causing decreased recognition by the secondary immunoglobulin. According to the results of the biotinylation assays, depicted in FIG. 2A, there was no reduction in biotinylation intensity for IgG$^{DNP}$ up to UV energies of 5 J/cm$^2$, demonstrating that the antigen binding activity of IgG$^{DNP}$ is preserved even at high UV energies. These results demonstrate that while the exact amount of UV energy an immunoglobulin can be exposed to and remain active depends on the particular immunoglobulin, the UV energies necessary for effective photocrosslinking of IBA-ligands to the NBS (<2.0 J/cm$^2$) has a minimal impact on both antigen binding activity and recognition by secondary immunoglobulins.

Effect of Buffer Conditions on Photocrosslinking Efficiency.

The efficiency of photocrosslinking is also dependent on the additives and pH of the buffer used to incubate the immunoglobulin/IBA-ligand mixture. Therefore, we investigated the effect of pH while crosslinking with a constant UV energy of 2.0 J/cm$^2$ and keeping the immunoglobulin (20 µM) and ligand (300 µM) concentrations constant. This relatively higher UV energy was chosen to enhance the photocrosslinking yield in order to better elucidate the difference in photocrosslinking efficiency under various buffer conditions. When the pH was decreased from 7.4 to 5.5, we observed that the average number of IBA-ligand conjugations dropped by 41% from 2.9 to 1.7 (FIG. 19B). Increasing the pH to 10.5 resulted in a large increase in the non-specific photocrosslinking events to the immunoglobulin, ~6 conjugations (FIG. 19B). This result was consistent with the known enhanced photo-reactivity of specific amino acids, such as histidine and lysine, at elevated pH values. These results demonstrated that a pH of about 6-8 provides optimal conditions for selective photocrosslinking of an IBA-ligand to the NBS with minimal non-specific conjugations.

Tween 20 is often added to immunoglobulin formulations as a stabilizer to reduce undesired non-specific hydrophobic interactions between proteins. Including Tween 20 in the buffer, up to 1% V/V, had negligible impact on the resulting number of IBA-FITC molecules photocrosslinked to the immunoglobulin (FIG. 19C). This result revealed that Tween 20 did not interfere with IBA binding to the NBS. Although including Tween 20 in the conjugation buffer was deemed unnecessary for efficient IBA-FITC conjugation, certain larger ligands that contain hydrophobic regions, such as targeting peptides and cytotoxic drugs, may benefit greatly from the presence of a surfactant. Incorporating a surfactant in the photocrosslinking buffer can potentially reduce non-specific interactions between the ligand and the immunoglobulin, thereby inhibiting any non-site-specific conjugations.

Determination of the Photocrosslinking Site by Western Blot Analysis.

Figure 6:
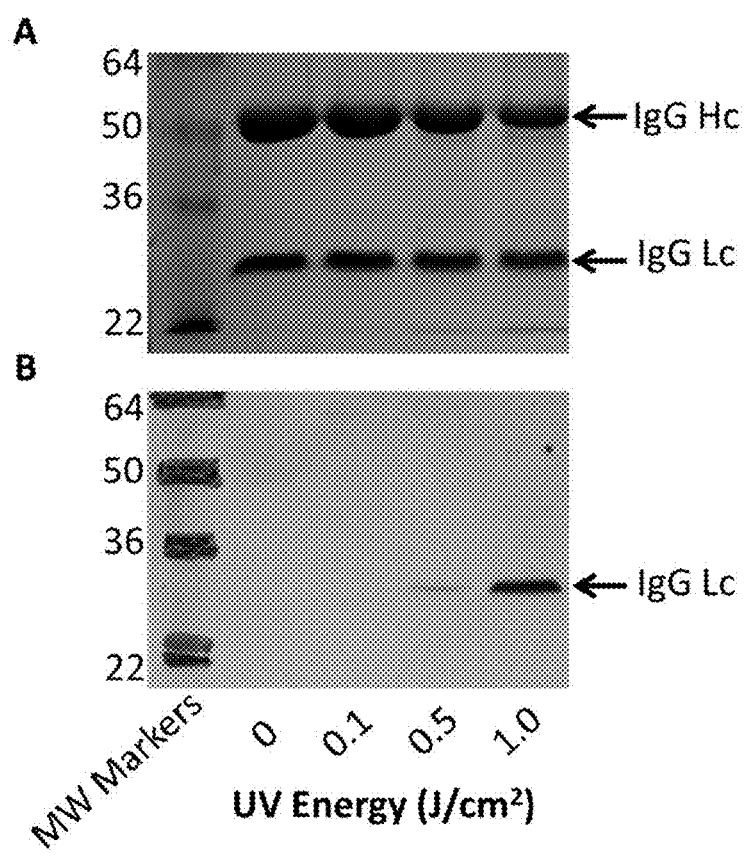
FIG. 6. Western blot analysis of UV-NBS photocrosslinking site on the immunoglobulin. IBA-biotin was crosslinked to the immunoglobulin (Rituximab) by exposure to UV energy from 0-1 J/cm$^2$ in PBS buffer. SDS-PAGE was run under reducing conditions and the proteins were transferred to a nitrocellulose membrane. A) The SDS-PAGE gel was stained by coomassie blue. B) Streptavidin-HRP was used to probe for covalently conjugated IBA-biotin. Blotted film shows that biotin tag only appears on the immunoglobulin light chain. Similar results were obtained using IgG$^{FITC}$ and IgG$^{DNP}$ (data not shown).
Figure 21:
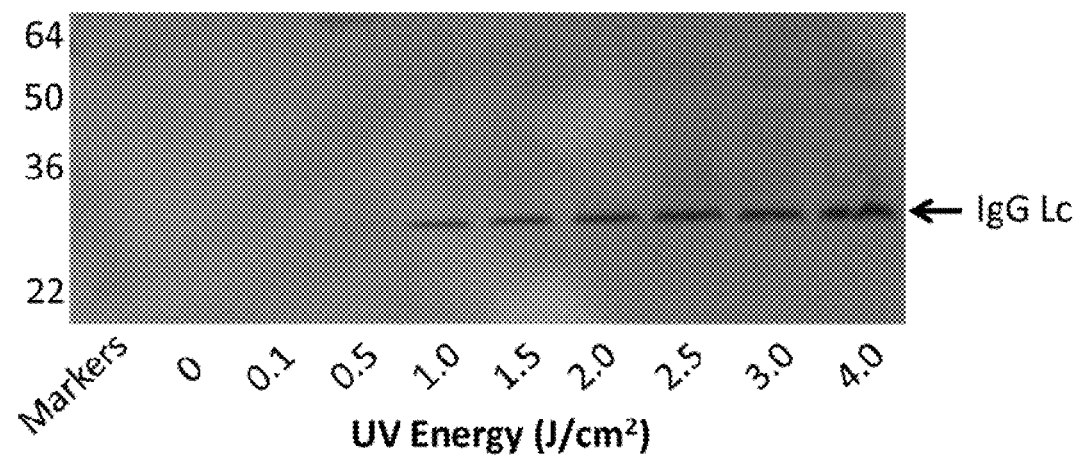
FIG. 21. Western blot displaying the photocrosslinking site at increasing UV energy exposures. IgG immunoglobulin (20 µM, Rituximab) was incubated with saturating IBA-biotin (300 µM) in PBS buffer, and exposed to UV energy from 0-4.0 $J/cm^2$.
Figure 39:
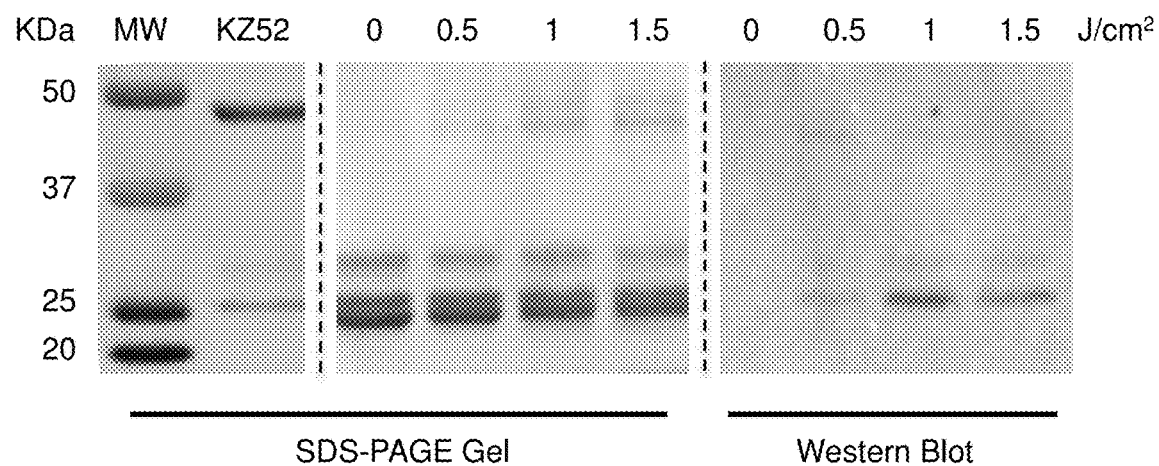
FIG. 39. Determination of site-specific conjugation of IBA-EG$_{11}$-Biotin to Fab fragment at the NBS via SDS-PAGE and Western Blot. The full length KZ52 immunoglobulin was run on the 10% SDS-PAGE gel in reducing conditions. The biotinylated Fab fragments exposed to increasing amounts of UV energy were also run on a 10% SDS-PAGE gel and the results were compared with the full length KZ52 immunoglobulin. The light chain of the full length KZ52 immunoglobulin matched with the upper band of the Fab fragment indicating that the upper band is the light chain and the lower band is the heavy chain of the Fab fragments. To show the specific location of biotinylation to the Fab fragment, a western blot assay was utilized by transferring the proteins from the gel to a nitrocellulose membrane and detection of the biotinylated Fab fragments was carried out with an HRP conjugated Streptavidin reporter. The results of the blotted film indicates that the biotinylation of Fab fragments at the NBS occurs specifically at the light chain confirming that the UV-NBS photo crosslinking methods can be utilized to site specifically modify Fab fragments similarly to full length immunoglobulin.

To verify the specificity of the IBA/NBS interaction and to demonstrate the site-selectivity of covalent bond formation at the NBS, a western blot analysis was carried out with IBA-biotin photocrosslinked immunoglobulin. Rituximab (20 μM) was incubated with a saturating concentration of IBA-biotin ligand (300 μM) in PBS for 1 h and then exposed to UV energy. The biotinylated immunoglobulins were run under reducing conditions on SDS-PAGE (FIG. 6A), transferred to a nitrocellulose membrane and biotinylated immunoglobulin fragments were probed by using HRP conjugated streptavidin (FIG. 6B). The developed film established that the biotinylation of the immunoglobulin occurred selectively at the light chain, and the yield of conjugation was dependent on the amount of UV energy exposure. While the NBS is comprised of residues that are both on the $V_L$ and $V_H$, the orientation of the non-covalent interactions between the IBA and the residues of the NBS yields crosslinking exclusively to the immunoglobulin light chain. This result was consistent across all three immunoglobulins tested (results not shown). At UV exposures up to 4.0 J/cm$^2$, biotinylation was still highly selective for the immunoglobulin light chain (FIGS. 21 and 39).

Determination of the Photocrosslinking Site Via Mass Spectrometry and Computational Docking Analysis.

Figure 22:
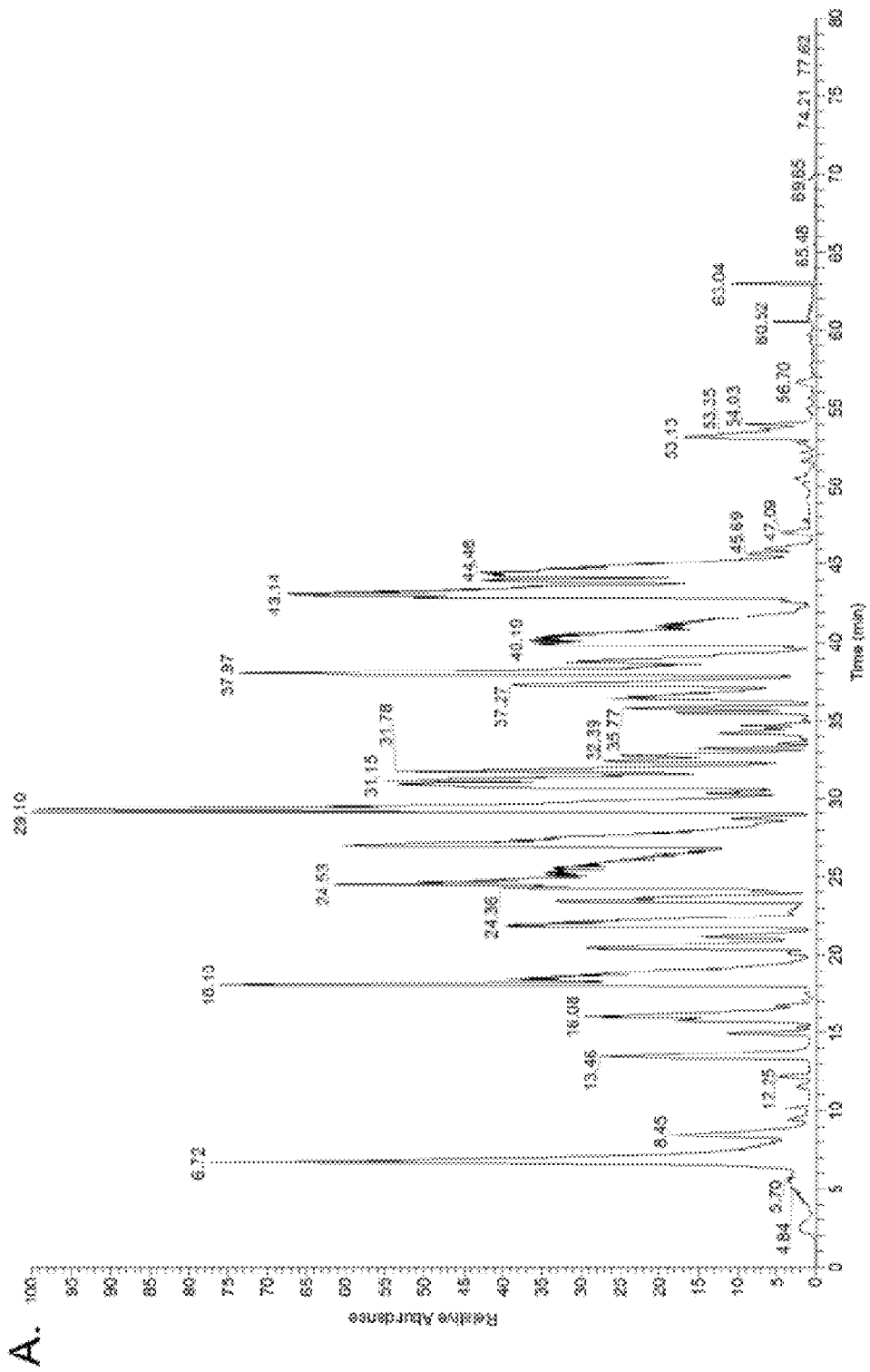
FIG. 22. A) Extracted LC/MS spectra from a tryptic digest of Rituximab in the presence of IBA-biotin (300 µM) with 2 $J/cm^2$ UV energy exposure. Base-peak chromatogram of the entire LC/MS separation is shown. B) Extracted MS spectra from the region where the modified and unmodified form of the ASSSVSYIHWFQQK fragment elute (30.54-31.42 min). Also shown is the m/z of the unmodified $[M+2H]^{2+}$ peptide at m/z 834.41 and the $[M+3H]^{3+}$ modified peptide at m/z 833.43 (inset). For reference, an unrelated peptide from the heavy chain that nearly co-elutes with this sequence at m/z 839.41 is also shown.
Figure 22:
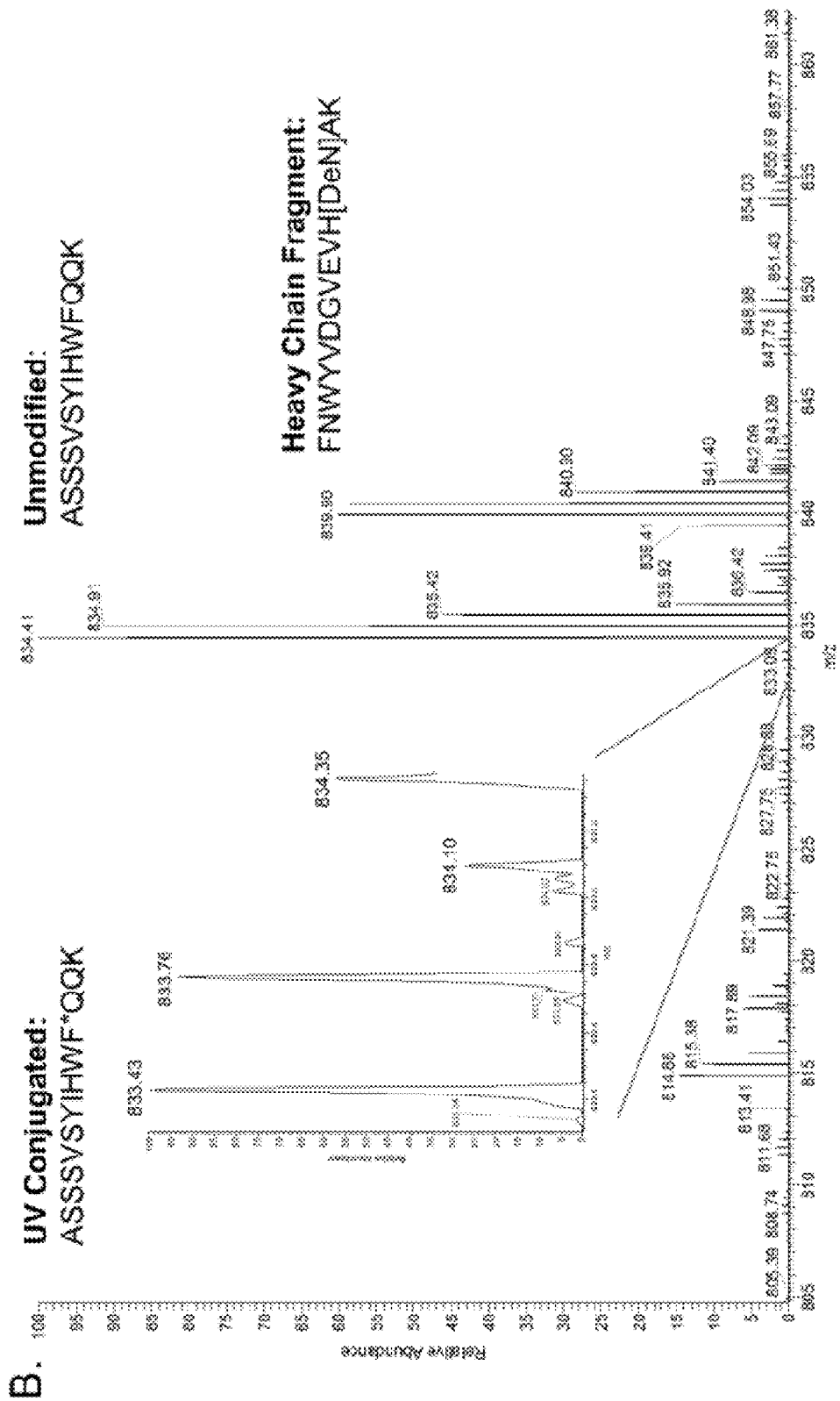
Figure 23:
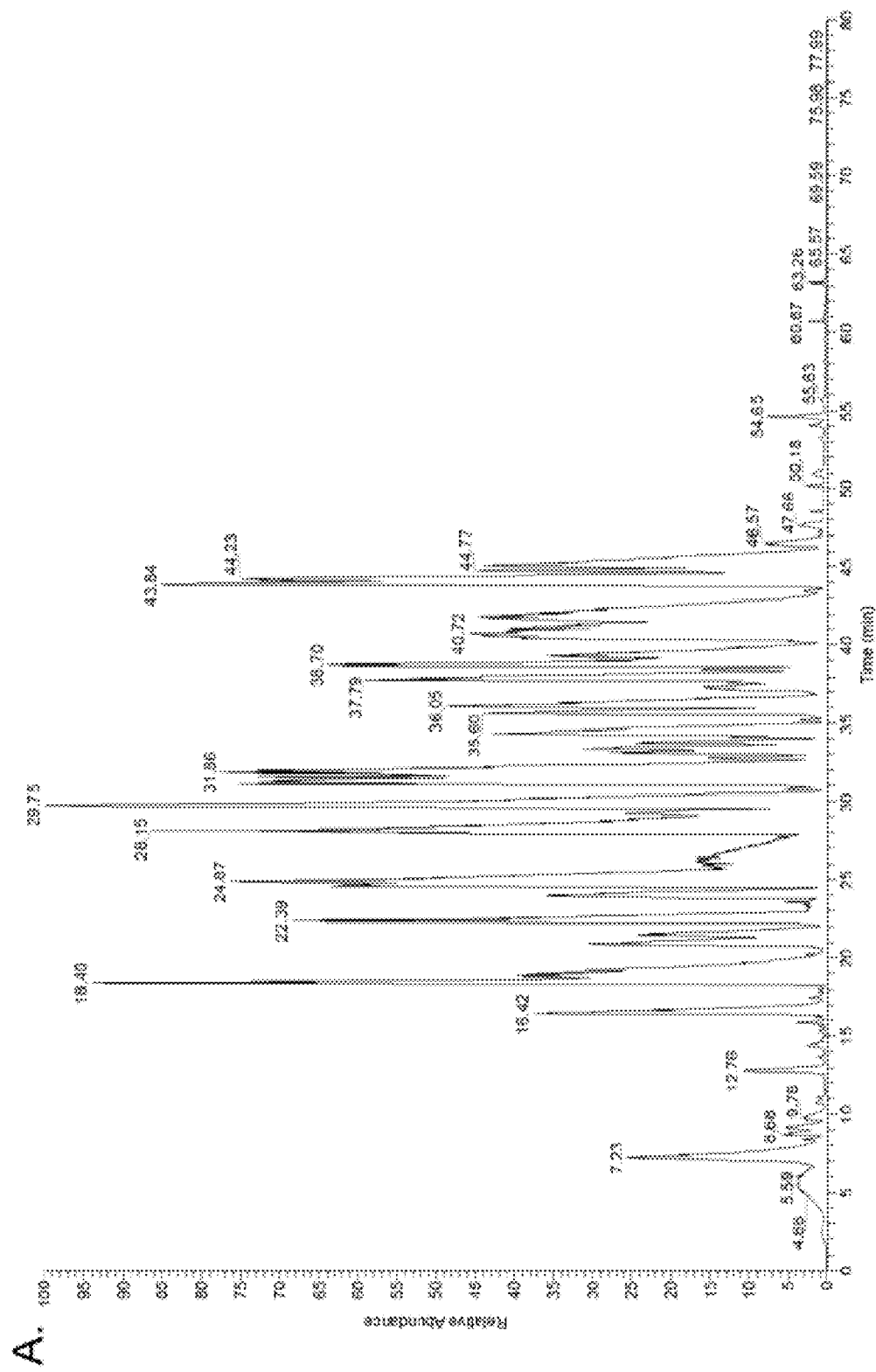
FIG. 23. A) Extracted LC/MS spectra from a tryptic digest of Rituximab in the absence of IBA-biotin. The base-peak chromatogram of the entire LC/MS separation of the unlabeled Rituximab sample is shown. B) Extracted MS spectra from the region where the modified and unmodified form of the ASSSVSYIHWFQQK fragment elute. The identical unmodified peptide at m/z 834.41 [M+2H]$^{2+}$ and reference fragment from the heavy-chain m/z 839.41 [M+2H]$^{2+}$ are present. Expectedly, the diagnostic ion m/z 833.43 that has been assigned as the modified peptide [M+3H]$^{3+}$ is not detected in the absence of IBA-biotin and in the absence of UV exposure (inset).
Figure 23:
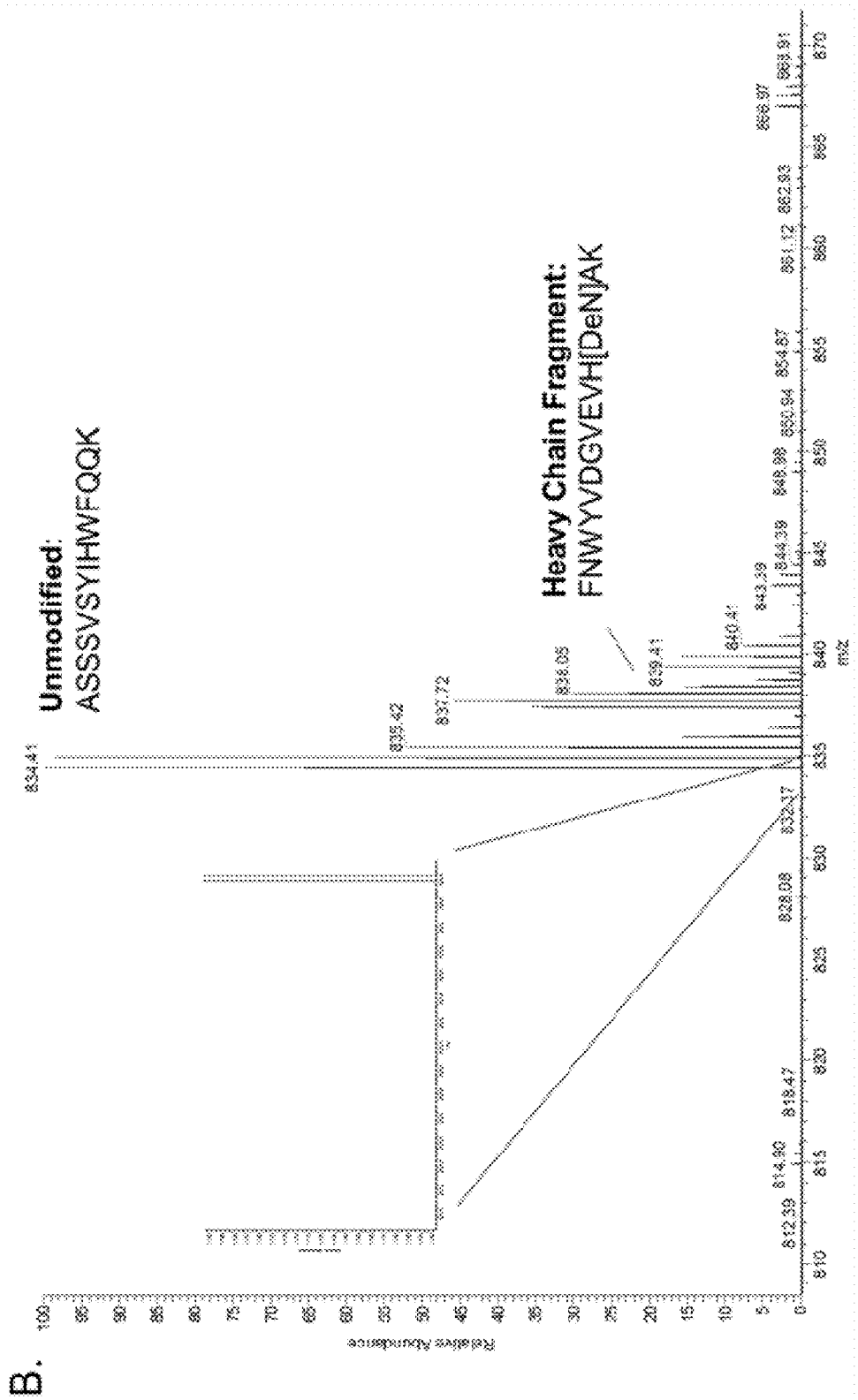

The western blot analysis revealed that the photocrosslinking of IBA-biotin was the result of a selective interaction between IBA and the immunoglobulin light chain. In order to discern the precise location of photocrosslinking via the UV-NBS method, we analyzed the IBA-biotin conjugated Rituximab using MS analysis. We chose Rituximab in our studies because it has a known amino acid sequence and an available crystal structure in the Protein Data Bank, both of which made analysis of the exact site of photocrosslinking possible. The IBA-biotin photocrosslinked Rituximab was first enzymatically digested into smaller peptide fragments in the presence of trypsin or pepsin using literature protocols. The digested immunoglobulin fragments were then separated on a C18 column and analyzed by an LTQ-Velos Orbitrap mass spectrometer. The biotinylated peptide fragment was then identified based on the presence of diagnostic precursor ions unique to internal fragmentation of the IBA-biotin molecule obtained under MS/MS conditions: 472.23, 679.50, and 714.27 m/z (indicative of intact IBA-biotin). These diagnostic ions were observed only in the biotinylated immunoglobulin samples and were used to identify the triply charged peptide fragment that IBA-biotin had been photocrosslinked to at 833.43 m/z (FIGS. 22 and 23). The presence of these diagnostic ions were found in at least one peptide digest from the trypsin and pepsin treated samples, further validating the photocrosslinking by orthogonal digestion methods. The sequence coverage was sufficient to allow for accurate screening of the entire immunoglobulin to assay all potential sites of conjugation (Table 3).

Figure 7:
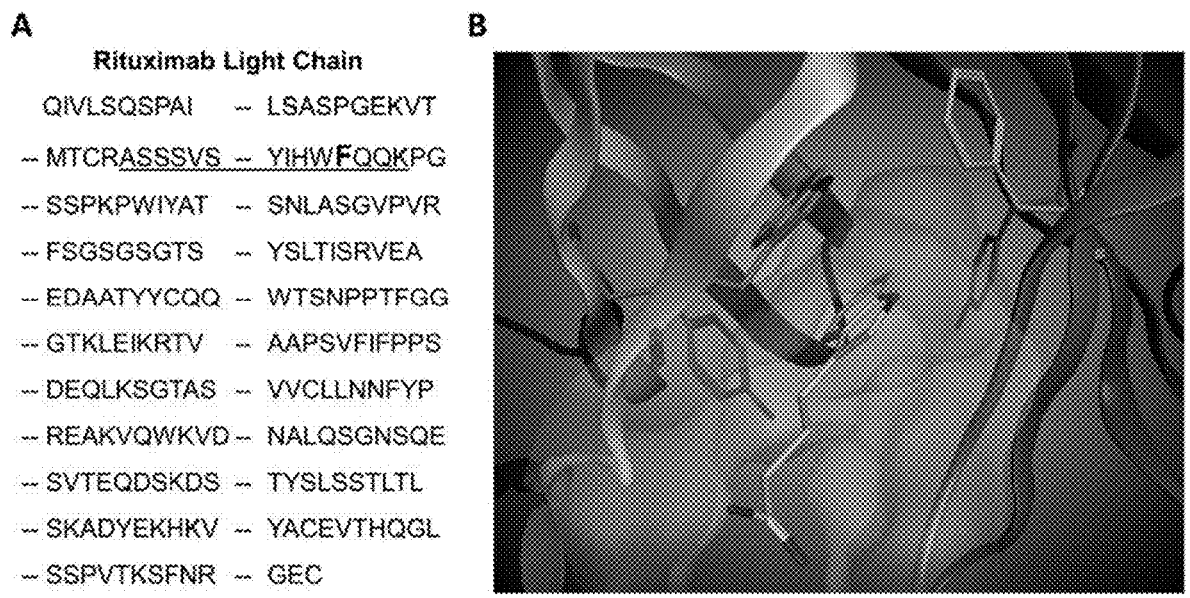
FIG. 7. A) Rituximab light chain sequence with UV modified peptide underlined and the proposed site of conjugation in bold (phenylalanine 42). B) Docking minimization of IBA in the Rituximab Fv demonstrating the orientation of the peptide and NBS side chains. NBS pocket shown as the central surface; IBA, V$_L$, V$_H$, NBS side chains, and Phe42 are also shown.
Figure 24:
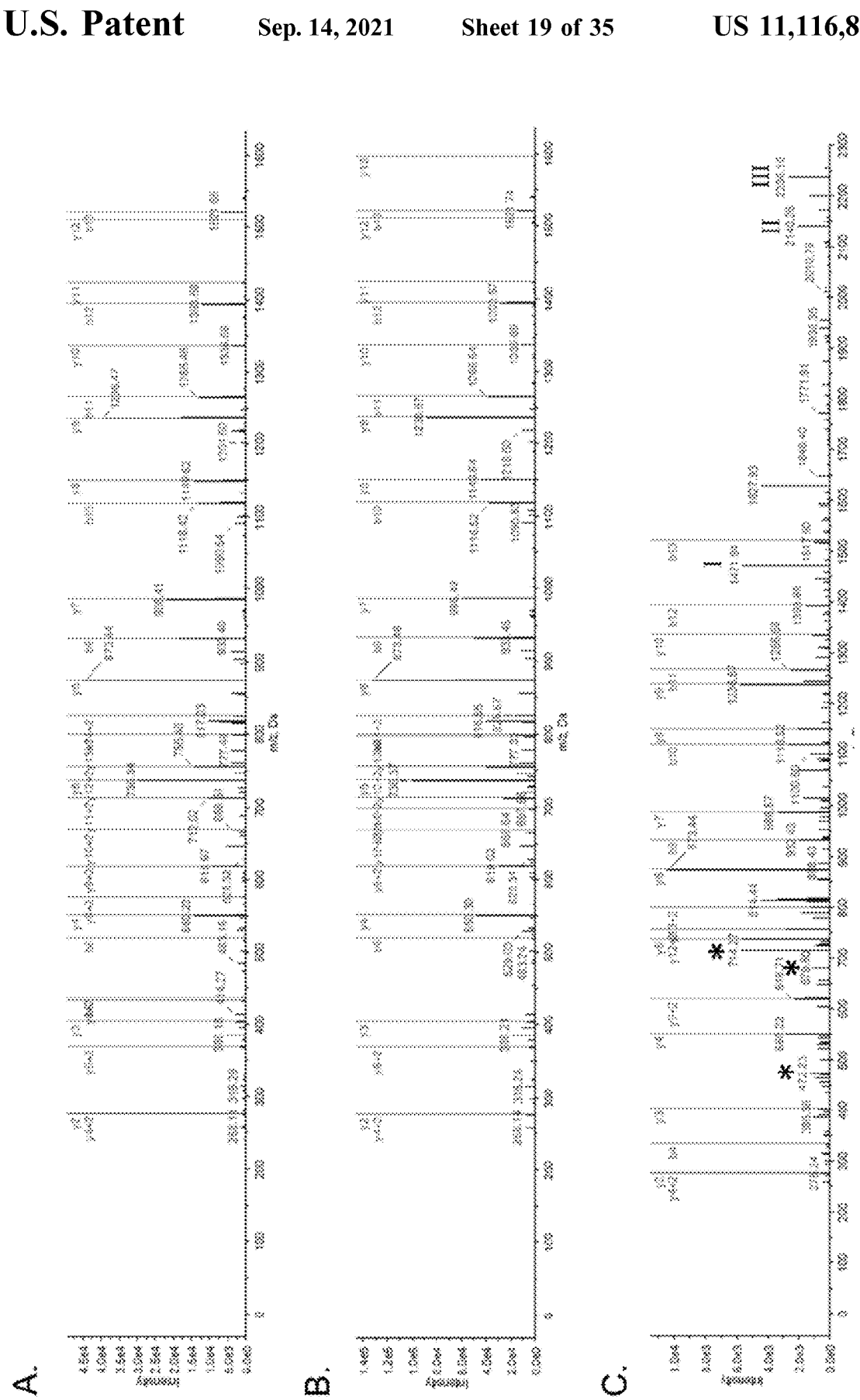
FIG. 24. A) Annotated MS/MS spectra from a tryptic digest of Rituximab in the presence and absence of IBA-biotin and UV exposure, illustrating the assigned MS/MS spectrum from the unlabeled and unirradiated Rituximab sample. B) Annotated spectrum from the unlabeled portion of the same peptide in the IBA-biotin UV exposed sample. C) Annotated MS/MS spectrum from the m/z 833.43 ion which we have determined has been photocrosslinked to IBA-biotin (ASSSVSYIHWFQQK). Highlighted by stars (*) are MS/MS ions that are diagnostic for the IBA-biotin modification: m/z 472.23 corresponds to cleavage after the 2nd peptide bond, m/z 679.5 was present as a +20 Da (indole) modification to a dominant m/z 659.5 m/z ion observed from the irradiated compound (data not shown), m/z 714.26 corresponds to a loss of the intact IBA-biotin from the peptide. (I) The m/z at 1471.94 corresponds to the y5 ion plus IBA-biotin with both indoles having kynurenine modifications and a single hydroxylation to the tyrosine (calculated m/z of 1471.7). (II) The m/z ion at 2140.26 corresponds to an IBA-biotin modified b12 fragment with a single N-formylkynurenine (+32 Da) modification, likely to the indole on the IBA-biotin peptide (calculated m/z of 2139.95). (III) The m/z ion at 2236.10 can be explained as an unmodified b13 fragment with an unmodified IBA-biotin UV conjugation (calculated m/z of 2236.07). This analysis narrows the site of UV modification to the bolded residues ASSSVSYIHWFQQK. Ions that are not annotated are likely internal fragments from the diverse population of modified ions present in the irradiated sample.
Figure 25:
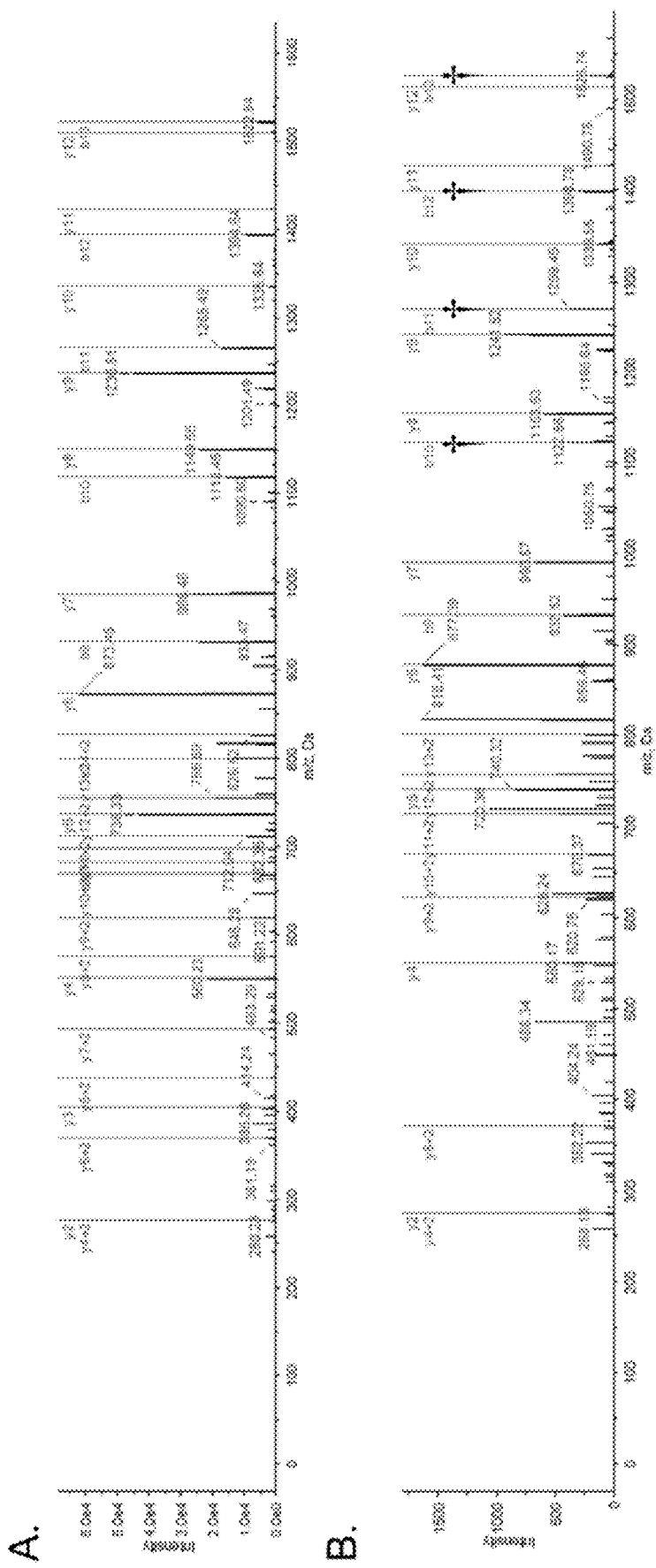
FIG. 25. A) Annotated MS/MS spectra from a tryptic digest of Rituximab in the presence and absence of UV exposure. Shown in (A) is an annotated MS/MS spectrum from the unmodified peptide in a 2 J/cm$^2$ irradiated sample in the absence of IBA-biotin. B) Highlights a common indole and tryptophan [W] modification observed upon UV exposure as a kynurenine conversion (+4 m/z); indicated by crosses (†) are the b ions that include tryptophan. Other modifications resulting from UV exposure were observed.
Figure 26:
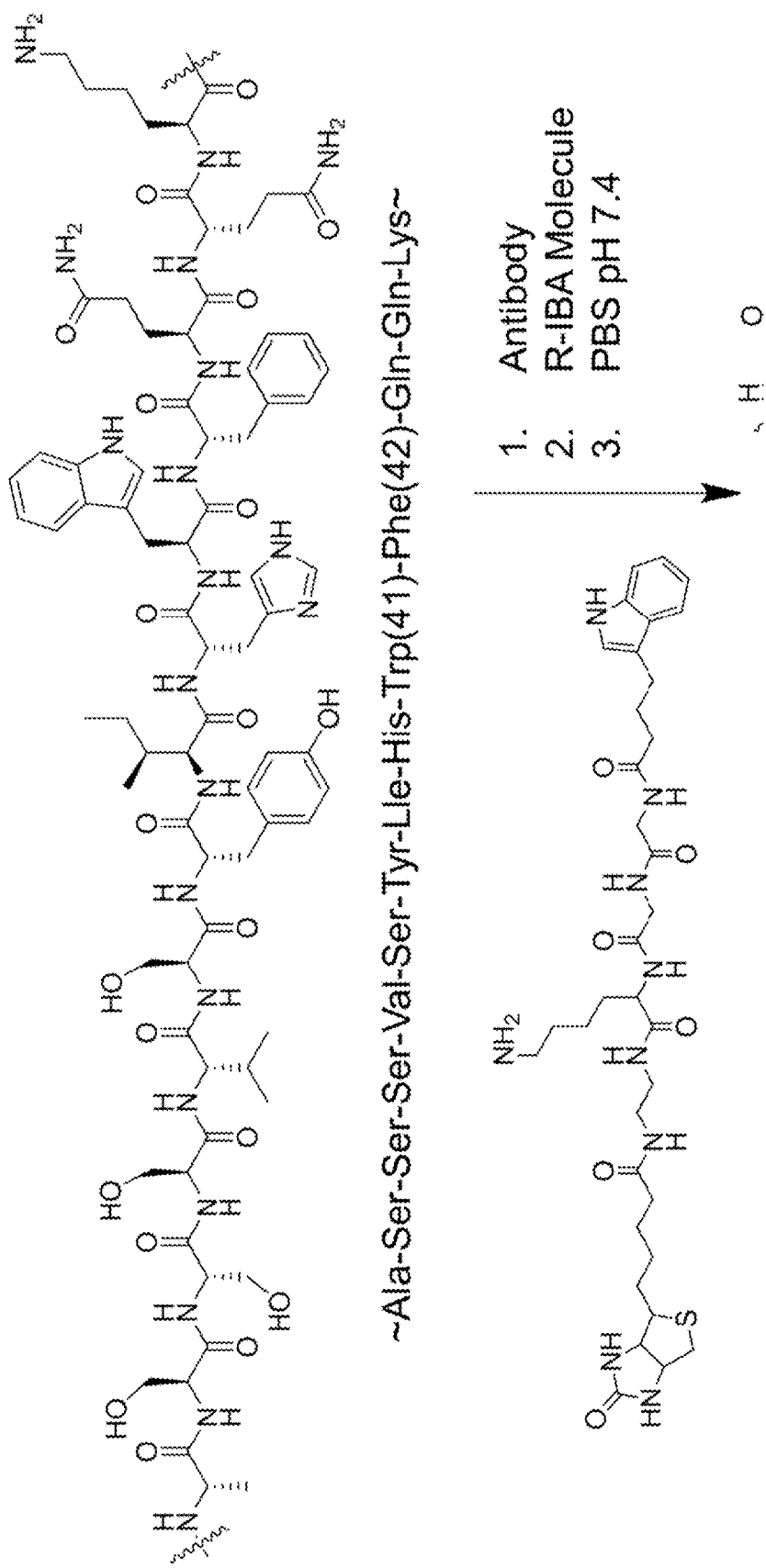
FIG. 26. A mechanism for UV covalent bond formation of IBA to the immunoglobulin NBS. Following incubation of the immunoglobulin with the IBA-biotin molecule and UV exposure, a covalent attachment of the IBA-biotin to the digested peptide fragment is observed. The digested peptide fragment that contains the UV site of conjugation is pictured at the top with phenylalanine at position 42 being one of the conserved NBS residues. When phenylalanine is exposed to UV light the final product is hydroxylation of the phenyl ring resulting in the formation of a tyrosine like amino acid derivative. This hydroxylation can occur at any site on the ring structure and is represented here as a hydroxylation at position G. UV exposure to NBS bound IBA causes the indole to become excited to the first triplet state ($^3$Trp, 8-20 μs lifetime) resulting in radical-cation formation and deprotonation giving rise to the neutral indolyl radical. From this state IBA most commonly undergoes photo-oxidation and through a complicated radical driven reaction pathway and associated decomposition results in kynurenine formation. When this reaction is carried out in the confined NBS the proposed result is covalent bond formation between the kynurenine and tyrosine derivative at position 42 on the immunoglobulin light chain. The crosslink is pictured here as a covalent bond formed between positions D and H but this bond may exist at any of the other ring locations. The specificity of conjugation was verified by comparison to carefully selected control digestions including: no UV exposure with incubated IBA-biotin, UV exposure in the absence of IBA-biotin, and UV exposure in the absence of IBA. The photo chemical products that result from UV exposure are highly dependent upon pH, solution ionic strength, the proximity of specific functional groups, hydrophobicity of the surrounding region, the presence of chromophores, and the wavelength of UV exposure. The sequence coverage was sufficient to allow for accurate screening of the entire immunoglobulin to assay for all potential sites of conjugation.
Figure 26:
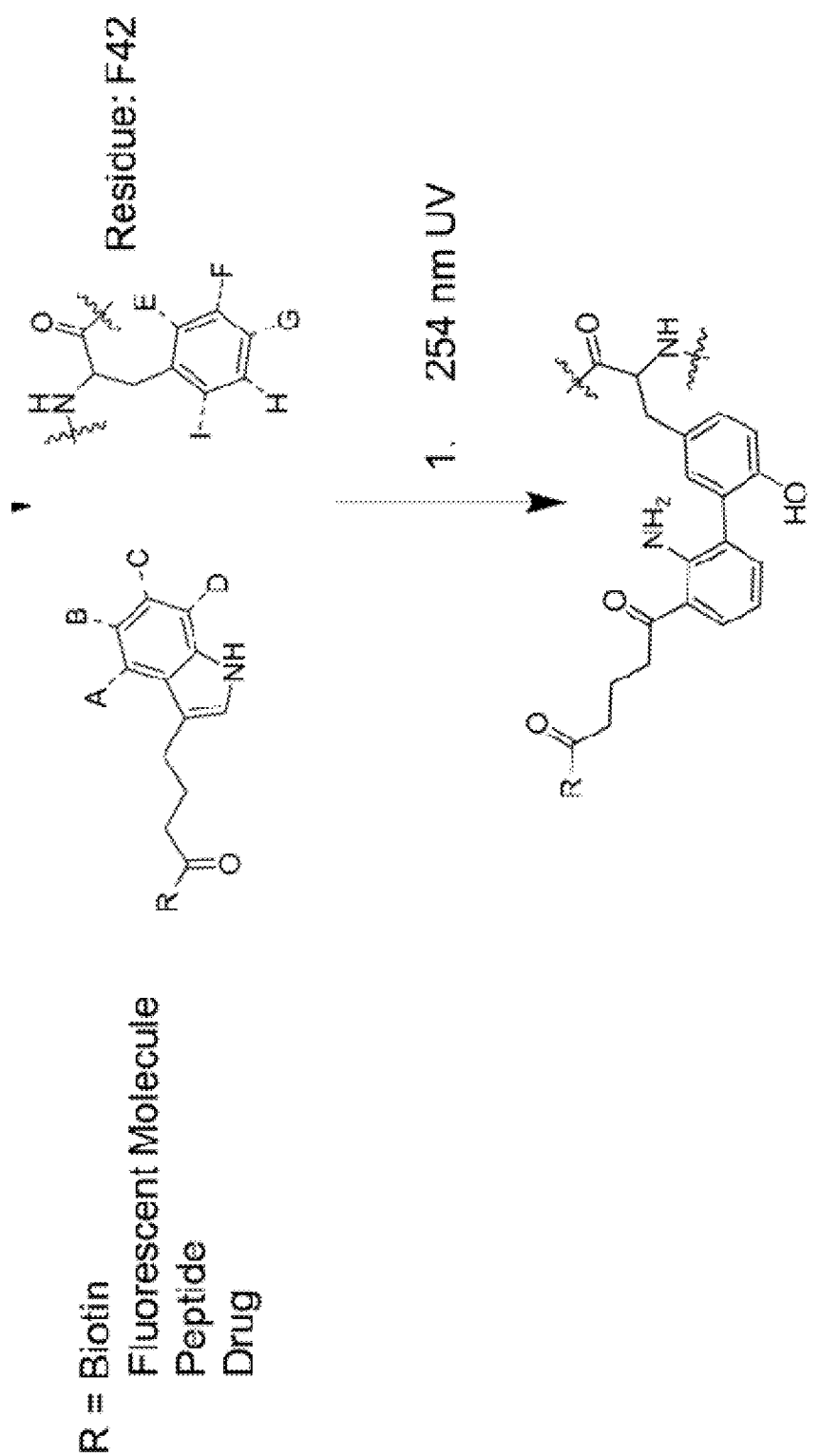
Figure 27:
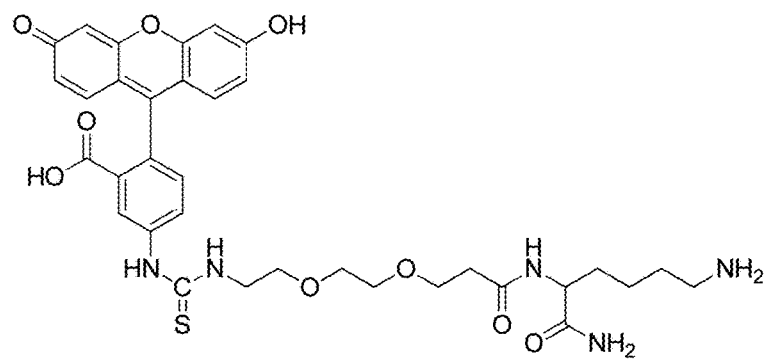
FIG. 27. The calculated exact mass for the FITC-amine ($C_{34}H_{39}N_5O_9S$) was 693.25 Da; found 694.20 Da. The FITC-amine molecule synthesized for this study was purified via reverse phase HPLC on a Zorbax 300SB-C18 semi-preparative 9.4×250 mm 5-micron column with increasing acetonitrile as the mobile phase. The purified fractions were collected and mass verified via MALDI-TOF-MS on a Bruker Autoflex III mass spectrometer in reflectron mode. The samples were spotted in 2,5-dihydroxy benzoic acid (DHB) on a stainless steel MALDI target plate. The exact masses were calculated using ChemBioDraw Ultra (Version: 12.0.2.1076). The purity was confirmed using RP-HPLC on an analytical Zorbax C18 column (>95%), and the yield was 80%.

The results of the MS analysis enabled the modified peptide fragments to be sequenced and the precise modified residue to be determined as the NBS residue F42 within the light chain variable fragment of the immunoglobulin (FIG. 7A). Identifying each fragment in the MS/MS data also allowed for the elucidation of a reaction mechanism incorporating common UV modifications to phenylalanine and indole rings (FIG. 1C). A detailed analysis of the MS/MS data can be found in FIGS. 24-26. Briefly, the analysis revealed that in the most simple conjugation mechanism, a covalent bond is formed directly between the phenylalanine at position 42 and the IBA with only a loss of two hydrogen atoms, m/z of 2236.10 (FIG. 24). In addition, UV exposure of IBA can cause the indole to become excited and result in the formation of an N-formylkynurenine as indicated by the m/z of 2140.26 corresponding to a covalent bond between the N-formylkynurenine and unmodified phenylalanine. Under continued UV exposure the N-formylkynurenine most commonly undergoes a photo decomposition reaction resulting in kynurenine formation (FIGS. 24 and 25). It is also well established that when phenylalanine is exposed to UV light, the dominant product is hydroxylation of the phenyl ring resulting in the formation of a tyrosine like amino acid derivative. The final identified MS/MS fragment indicates a covalent bond between the kynurenine and hydroxylated phenylalanine as indicated by an m/z of 1471.94 (FIG. 1C). These three diagnostic ions, when taken together, verify the site of conjugation to be F42 on the immunoglobulin $V_L$ and illustrate a reaction mechanism that is consistent with well-established UV modifications (FIG. 26).

To identify the binding mode of IBA to the NBS, we performed a computational docking analysis of IBA at the Rituximab NBS. A flexible receptor minimization was carried out to allow the IBA molecule to bind more deeply into the NBS, since we hypothesized that the indole ring might intercalate between the heavy and light chains of the Fab. The top-ranking ligand binding mode from the IBA docking was minimized using the MOE Energy Minimize program, which applies a series of minimization methods including Steepest Descents, Conjugate Gradient, and Truncated Newton until the system converged (gradient <0.05). The AMBER99 force field with a Generalized-Born implicit solvation model was used to model both the internal energy of the protein, the non-bonded interactions, and the solute-solvent interactions. The energy-minimized binding mode is shown in FIG. 7B. The docking analysis suggests a binding conformation where IBA stacks against the indole ring of the tryptophan at position 118 on the $V_H$, fixing the IBA within the pocket. Based on the orientation of the reactive aromatic side chains, the only accessible site for conjugation is the phenylalanine at position 42 on the light chain. This finding was in line with our MS analysis of the conjugation site and helped to determine the most likely site of covalent bond formation between IBA and phenylalanine (FIG. 26).

Utilization of the UV-NBS Method for Detection of Cell-Surface Antigens Via Flow Cytometry.

Figure 8:
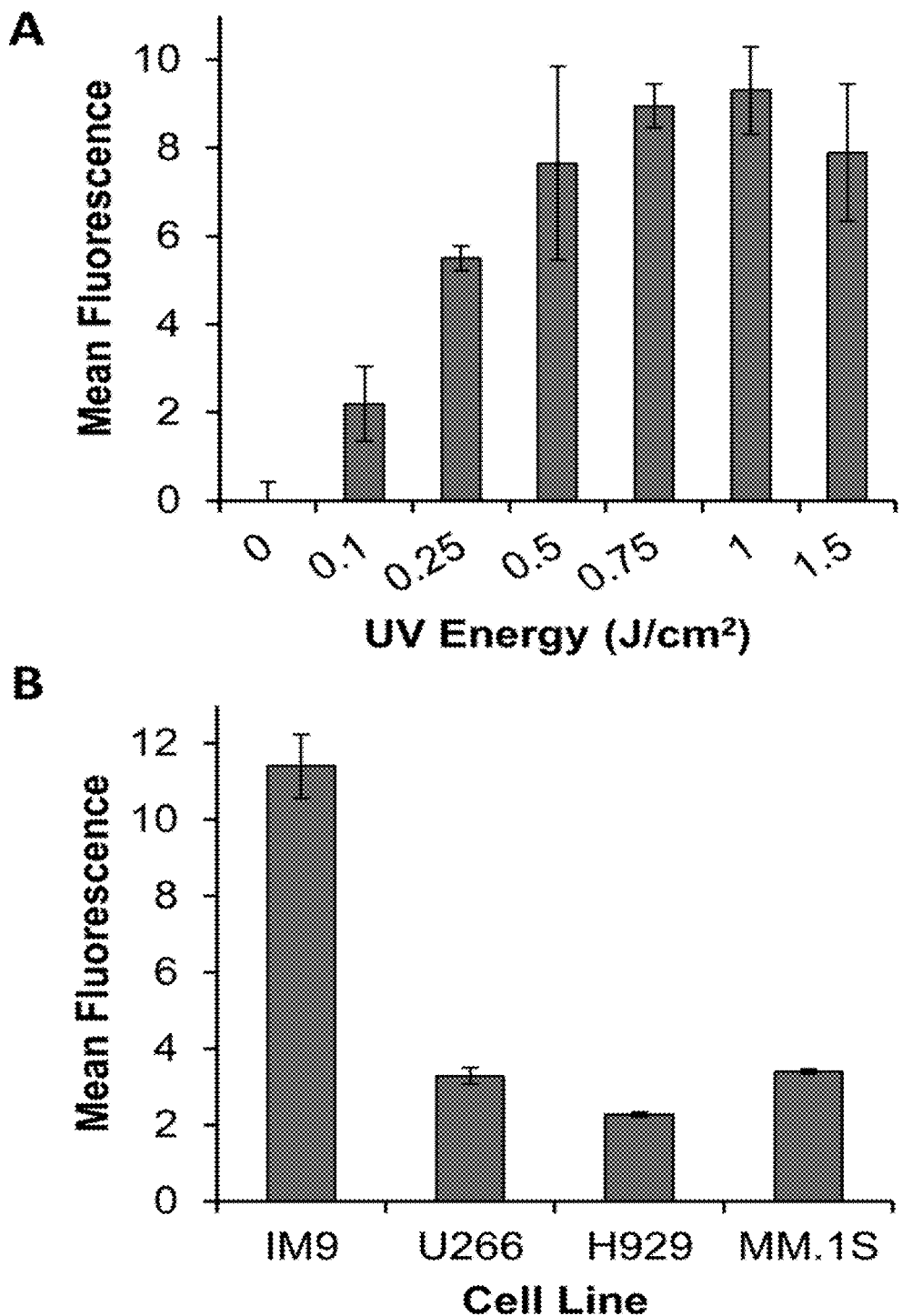
FIG. 8. A) The optimum UV energy exposure necessary to conjugate IBA-FITC to Rituximab as determined by an in vitro CD20 antigen detection flow cytometry assay on IM9 cells. B) Screening of various cell lines using IBA-FITC photocrosslinked Rituximab (1 J/cm$^2$ UV energy) to assess CD20 expression levels. All data represents means (±SD) of triplicate experiments.

FITC labeled immunoglobulins are commonly used in flow cytometry assays for determination of expression levels of cell surface receptors as well as for cell sorting. To demonstrate the utility of the UV-NBS method in flow cytometry applications, we photocrosslinked IBA-FITC to Rituximab site-specifically at the NBS and used this immunoglobulin to analyze CD20 expression levels on multiple myeloma cells. For this application, Rituximab (20 μM) was incubated with saturating levels of IBA-FITC and exposed to increasing amounts of UV energy to perform the site-specific photocrosslinking reaction. The IBA-FITC photocrosslinked Rituximab (200 nM) was then incubated with the CD20 positive IM9 cell line, and the CD20 expression levels were detected by flow cytometry. As can be seen in FIG. 8A, the fluorescent signal increased with increasing UV energy with an optimal UV exposure of 1 J/cm$^2$, consistent with previous results. To ensure that the interaction between the Rituximab and the IM9 cell line was due to specific binding of the immunoglobulin to the CD20 surface antigen, the Rituximab-IBA-FITC conjugate was incubated with three CD20 negative myeloma cell lines, U266, H929, and MM.1S. This resulted in negligible binding of the immunoglobulin, demonstrating specificity of the Rituximab-IBA-FITC conjugate for the CD20 antigen (FIG. 8B). These results validate the utility of the UV-NBS method in selective labeling of immunoglobulins with fluorescent molecules such as FITC for numerous applications that include flow cytometry.

Utilization of the UV-NBS Method in Photocrosslinking of Functional Peptides (iRGD) and Chemotherapeutic Agents (Paclitaxel) to Immunoglobulins.

Next, we demonstrated the utility of the UV-NBS photocrosslinking method in site-selective conjugation of functional peptides to immunoglobulins by conjugating the cyclic iRGD peptide to Rituximab and IgG$^{DNP}$. The cyclic iRGD peptide, first identified by Rouslahti and coworkers, reportedly enhances tumor penetration of immunoglobulins and nanoparticles by incorporating a cell internalization sequence in conjugation with an RGD tumor targeting motif. The iRGD cyclic peptide construct was covalently conjugated to IBA to enable photocrosslinking of the IBA-iRGD molecule to the immunoglobulins using the UV-NBS method. During the synthesis of IBA-iRGD, an ethylene glycol linker of two units was introduced between IBA and iRGD to provide flexibility. In addition, selectively protected lysine was also added which facilitated conjugation of FITC to the IBA-iRGD molecule (FIG. 13). The addition of FITC allowed for the quantification of the number of conjugations via absorbance at 494 nm by SEC peak integrations, as described previously.

Figure 9:
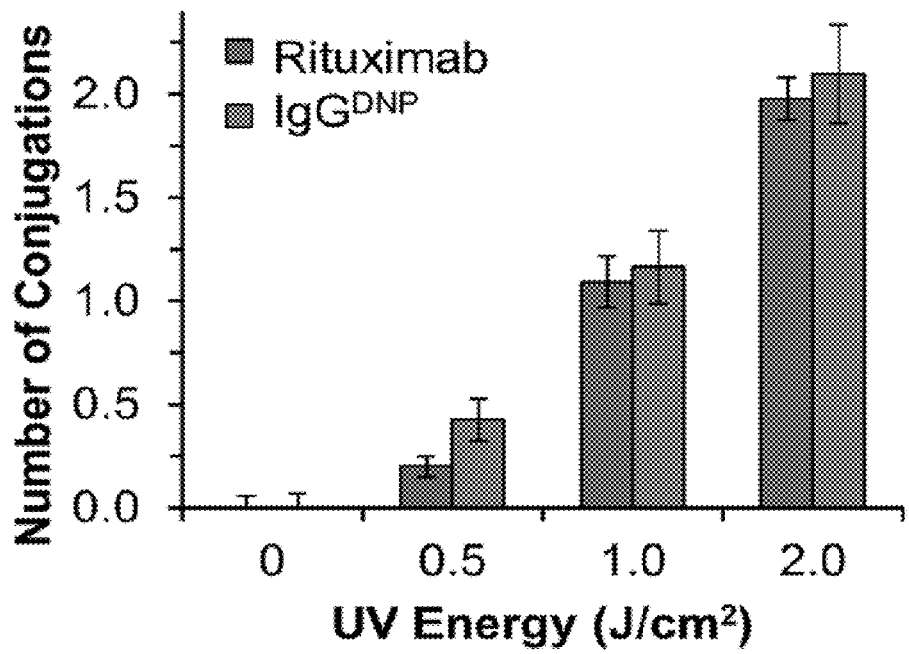
FIG. 9. A) The effect of UV energy on the average number of IBA-iRGD conjugations per immunoglobulin. B) The effect of UV energy on the average number of IBA-paclitaxel conjugations per immunoglobulin. The photocrosslinking was carried out in PBS pH 7.4 with 0.1% Tween 20 at fixed ligand and immunoglobulin concentrations of 300 µM and 20 µM, respectively. Conjugation number determined via SEC 494 nm peak integration. All data represents means (±SD) of triplicate experiments.
Figure 9:
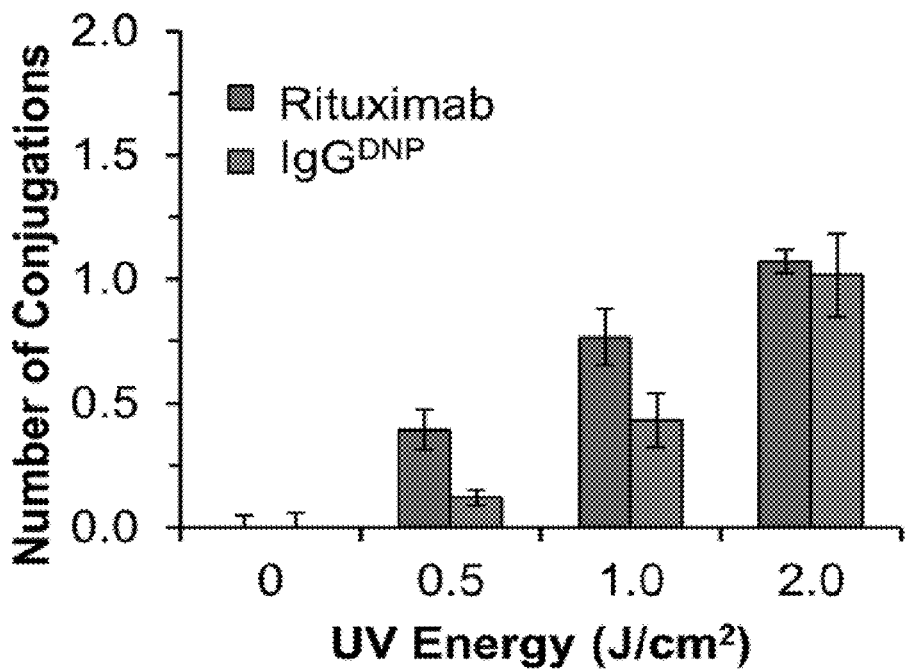

While keeping the immunoglobulin (20 µM) and IBA-iRGD ligand (300 µM) concentrations constant, the samples were exposed to increasing UV energies. The SEC analysis demonstrated successful conjugation of IBA-iRGD to both Rituximab and IgG$^{DNP}$ at 1 J/cm$^2$ with an average of ~0.75 peptide conjugations per immunoglobulin (FIG. 9A). It is noteworthy that based on the conjugation efficiency observed for the IBA-biotin molecule (FIG. 2) and the average number of conjugations of IBA-FITC (FIG. 4), ~2 IBA-iRGD conjugations per immunoglobulin was expected at this UV energy. We predict that the decreased number of conjugations at 1 J/cm$^2$ UV energy is a result of the iRGD peptide non-specifically associating with the immunoglobulin surface and sterically blocking the NBS due to its considerably large size. Alternatively, the conformation of the IBA-iRGD peptide construct in solution may render the IBA inaccessible for binding to the NBS. To minimize IBA-iRGD conformations as well as reduce the non-specific association of the peptide with the immunoglobulin, the photocrosslinking was carried out at an elevated temperature (50° C.). This resulted in nearly a 2-fold increase in the average number of conjugations to ~1.4 IBA-iRGD molecules per immunoglobulin. While increasing the temperature improved the coupling efficiency, high temperatures have the potential to negatively impact immunoglobulin activity through thermal denaturation of the secondary and tertiary structure (although we did not observe this under these relatively mild conditions). For this reason, we evaluated the addition of Tween 20 to the buffer, which is a more gentle method to inhibit the non-specific hydrophobic associations between the IBA-iRGD and help eliminate other steric restrictions due to non-specific interactions. Incorporating 0.1% Tween 20 in the conjugation buffer, and increasing the UV energy to 2 J/cm$^2$ at RT, yielded an average of 2.0 conjugations per immunoglobulin (FIG. 9A). The addition of 0.1% Tween 20 to the photocrosslinking buffer resulted in nearly a 100% conjugation efficiency of IBA-iRGD to all NBS, a 3 fold increase in conjugation efficiency when compared to PBS pH 7.4 in the absence of Tween 20.

Additionally, we also demonstrated the utility of the UV-NBS method in site-selective conjugation of chemotherapeutic agents via photocrosslinking of paclitaxel to IgG$^{DNP}$ and Rituximab. We synthesized paclitaxel in a prodrug form by conjugating it to IBA using an ethylene glycol linker via a hydrolysable ester bond (FIG. 14). This particular prodrug paclitaxel conjugation strategy has shown cytotoxic efficacy in literature, releasing active paclitaxel upon internationalization within the target cell. Due to the hydrophobic nature of the paclitaxel, two arginine residues were also included in the IBA-paclitaxel construct to increase charge and aid in solubility. While keeping the immunoglobulin (20 µM) and ligand (300 µM) concentrations constant, the samples were exposed to increasing UV energies. The SEC analysis demonstrated successful conjugation of IBA-paclitaxel to both Rituximab and IgG$^{DNP}$ at 1 J/cm$^2$ with an average of ~0.5 conjugations per immunoglobulin (FIG. 9B). This number of IBA-paclitaxel conjugations was less than the anticipated two conjugations per immunoglobulin at this UV energy. This was again likely a result of non-specific hydrophobic association of paclitaxel to the immunoglobulin surface, blocking the NBS. However, the addition of 0.1% Tween 20 to the IBA-paclitaxel photocrosslinking buffer did not provide an increase to the coupling yield, presumably because it was not sufficient to inhibit the hydrophobic association of paclitaxel to the immunoglobulin. The IBA-paclitaxel photocrosslinking reached a maximum of ~1 conjugation per immunoglobulin for both Rituximab and IgG$^{DNP}$ at 2 J/cm$^2$ (FIG. 9B). While the reason for the reduced overall coupling yield when photocrosslinking IBA-paclitaxel to the NBS is unclear, including a stronger surfactant may help improve the coupling by further reducing interactions of the IBA-paclitaxel to the immunoglobulin. The average number of IBA-iRGD and IBA-paclitaxel conjugations per immunoglobulin for the various UV energies are summarized in Table 4. Taken together, these results demonstrated that while optimal conditions may vary depending on the particular IBA-ligand being used, efficient photocrosslinking of peptides and chemotherapeutics can be attained utilizing the UV-NBS method.

While the UV-NBS photocrosslinking method can be applied broadly, there still remain some limitations. The UV-NBS method currently cannot be implemented for photocrosslinking of functional ligands that are UV sensitive. Some examples of UV sensitive functional ligands are hexa-histidine to his-tag an immunoglobulin facilitating capture via immobilized metal affinity chromatography (IMAC), DNA to facilitate surface immobilization on protein microarrays, and exceptionally photo-sensitive fluorophores that are prone to photo-bleaching. We are currently developing methods to site-specifically photocrosslink an orthogonal reactive group to the NBS to facilitate conjugation of UV sensitive moieties to the NBS through the intermediary UV-NBS conjugated reactive group.

Conclusions.

The results presented in this study establish the UV-NBS method as a practical, gentle, and reproducible method for site-specific conjugation of functional ligands to immunoglobulins at the NBS. Through an in depth mass spectrometry analysis and detailed computational docking study, we have located the precise site of photocrosslinking to be Phe42 within the Fv of the immunoglobulin light chain and have proposed a photocrosslinking mechanism. With high crosslinking efficiencies, the UV-NBS provides a site-specific covalent conjugation method that does not impact antigen or Fc binding interactions and can be implemented for nearly all immunoglobulin isotypes across various species, regardless of antigen specificity. We have validated the utility of the UV-NBS method by successfully functionalizing three different immunoglobulins with (i) biotin, (ii) FITC, (iii) iRGD peptide, and (iv) paclitaxel. Immunoglobulins that are functionalized with biotin or FITC via the UV-NBS method can be directly implemented for use in numerous immunoassays including western blotting, ELISA, FACS, and immunohistochemistry. UV-NBS functionalized immunoglobulins containing the iRGD targeting peptide results in the formation of a bispecific multivalent immunoglobulin conjugate with potential for enhanced tumor targeting and penetration, and paclitaxel conjugated immunoglobulins provide for targeted delivery of cytotoxic drugs. Provided in this study are just a few examples that validate the utility of the UV-NBS method for use in academic research, industry, and in the clinical setting. In summary, the UV-NBS method provides a universal, site-specific, and efficient method to functionalize immunoglobulins, with significant implications in various diagnostic and therapeutic applications.

Example 2. UV-NBS Photocrosslinking of Reactive Thiol Moieties

Figure 28:
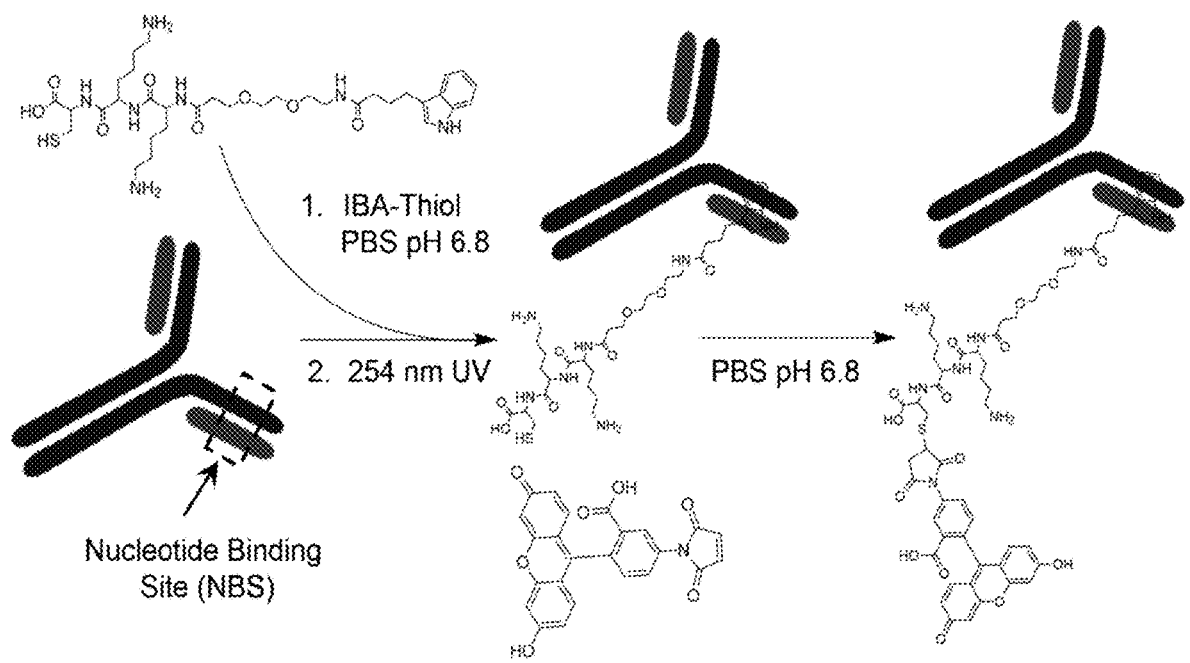
FIG. 28. A schematic representation of the method for UV photocrosslinking of reactive thiol ligands to immunoglobulins at the NBS. IBA-Thiol first associates with the immunoglobulin at the NBS and upon UV exposure a covalent bond forms between IBA and the immunoglobulin. The site-specific IBA-Thiol functionalized immunoglobulin can then be reacted to a maleimide bearing molecule such as maleimide-fluorescein.
Figure 32:
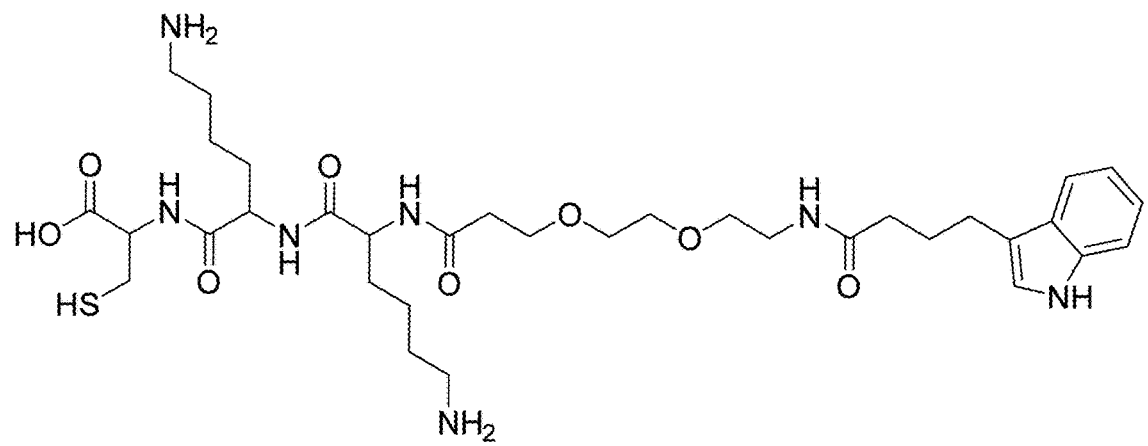
FIG. 32. The calculated exact mass for the IBA-Thiol ($C_{34}H_{55}N_7O_8S$) was 721.3 Da; found 722.45 Da. The IBA-Thiol molecule synthesized for this study was purified via reverse phase HPLC on a Zorbax 300SB-C18 semi-preparative 9.4×250 mm 5-micron column with increasing acetonitrile as the mobile phase. The purified fractions were collected and mass verified via MALDI-TOF-MS on a Bruker Autoflex III mass spectrometer in reflectron mode. The samples were spotted in 2,5-dihydroxy benzoic acid (DHB) on a stainless steel MALDI target plate. The exact masses were calculated using ChemBioDraw Ultra (Version: 12.0.2.1076). The purity was confirmed using RP-HPLC on an analytical Zorbax C18 column (>95%), and the yield was 60%.

The UV-NBS photocrosslinking technique requires exposure to UV energy that some functional ligands may not be stable to. In this study, we demonstrate the utility of the UV-NBS immunoglobulin functionalization strategy for conjugation of reactive thiol ligands to immunoglobulins at their NBS. By synthesizing an IBA conjugated version of cysteine (IBA-Thiol) a reactive thiol group can be site-specifically photocrosslinked to immunoglobulins at the NBS (FIG. 32). This thiol group can then be used as an orthogonally reactive site to conjugate UV sensitive functional ligands that possess either a thiol reactive group resulting in disulfide bond formation or subsequent reaction with a maleimide functionalized ligand (FIG. 28). The results detailed here provide a universal technique for the site-specific conjugation of UV sensitive functional ligands to immunoglobulins at the NBS, while preserving immunoglobulin activity.

Materials.

Indole-3-butyric acid (IBA), N-acetyl-L-cysteine, N,N-Diisopropylethylamine (DIEA), 5,5'-Dithiobis(2-nitrobenzoic acid), dithiothreitol (DTT), and fluorescein-5-maleimide were purchased from Sigma-Aldrich (St. Louis, Mo.). Streptavidin-HRP, HRP-conjugated IgG Fcγ specific goat anti-mouse, and HRP-conjugated IgG goat anti-fluorescein were purchased from Jackson ImmunoResearch (West Grove, Pa.). Heat shock isolated bovine serum albumin (BSA) and Amicon Ultra centrifugal filters (0.5 mL, 10K) were purchased from EMD Millipore (Billerica, Mass.). Amplex Red Assay Kit was purchased from Invitrogen (Grand Island, N.Y.). High binding 96-well ELISA plates were purchased from Thermo Scientific (Rockford, Ill.). NovaPEG Rink Amide resin, Biotin NovaTag resin, Fmoc-Cys(Trt)-Wang resin, and all other amino acids were purchased from Novabiochem (Billerica, Mass.). Fmoc-N-amido-dPEG$_2$-acid was purchased from Quanta Biodesign (Powell, Ohio). Mouse anti-PSA (IgG$^{PSA}$, clone: B731M) and purified free prostate specific antigen (PSA) were purchased from Meridian Life Science, Inc. (Memphis, Tenn.).

Synthesis of IBA-Thiol.

IBA-Thiol was synthesized using standard solid phase peptide synthesis protocols on a Fmoc-Cys(Trt) Wang resin and Fmoc chemistry. Fmoc-Lys(Boc)-OH was coupled to the resin following HBTU activation in DMF and DIEA at RT for 3.5 h while agitating. Fmoc was deprotected using 20% piperidine in DMF and the following residues were added in order: Fmoc-Lys(Boc)-OH, Fmoc-N-amido-dPEG$_2$-acid, and IBA. Kaiser tests were performed between coupling steps to monitor the synthesis progress. The peptide was cleaved from the resin in a solution of 4% triisopropylsilane, 4% D.I. water, 4% DTT and 88% TFA for 45 min at RT (FIG. 32). IBA-Thiol was purified via RP-HPLC on a Zorbax C18 column, and characterized using MALDI-TOF MS. The purity was confirmed using RP-HPLC on an analytical Zorbax C18 column (>95%), and the yield was 70%.

Assessing Antigen Binding Activity and Fc Stability of the Immunoglobulin Via ELISA.

Antigen coated ELISA plates were generated by adsorbing PSA (10 nM) to high binding 96-well ELISA plates in 0.05 M carbonate-bicarbonate coating buffer at pH 9.6 for 2 hours at RT. The plate surfaces were then blocked with BSA blocking buffer (200 μL of 5% BSA in PBS pH 7.4 with 0.1% Tween 20) for 1 h. The IgG$^{PSA}$ was then exposed to UV light (254 nm) in the presence or absence of IBA-Biotin or IBA-Thiol (300 μM) in PBS pH 6.8. Excess ligand was removed via Amicon spin concentrators and UV conjugated IBA-Thiol was then reacted with 5 equivalents of fluorescein-5-maleimide for 1 hour at RT. The UV coupled IgG$^{PSA}$ was then incubated on the antigen coated plate surfaces. The plates were washed to remove any unbound components using an automated plate washer (three cycles of 200 μL PBS with 0.05% Tween 20 at pH 7.4). The wells were incubated with a 1:5,000 dilution of HRP-anti-Fc immunoglobulin (1.0 mg/mL stock) in BSA blocking buffer for 1 h to quantify the total amount of antigen bound immunoglobulin (active Fc). Amplex red, the HRP substrate, was added and fluorescent product formation was observed on a Molecular Devices SpectraMax M5 plate reader (ex. 570 nm, em. 592 nm). Control experiments performed without capture immunoglobulin were used as background for the antigen and Fc stability detection measurements. The results are reported as relative fluorescence units (RFU). All data represents means (±SD) of triplicate experiments.

Assessing Immunoglobulin UV Biotinylation and Thiolation Via ELISA.

Antigen coated ELISA plates were generated by adsorbing PSA (10 nM) to high binding 96-well ELISA plates in 0.05 M carbonate-bicarbonate coating buffer at pH 9.6 for 2 hour at RT. The plate surfaces were then blocked with BSA blocking buffer for 1 h. The IgG$^{PSA}$ was then exposed to UV light (254 nm) in the presence or absence of IBA-Biotin or IBA-Thiol (300 μM) in PBS pH 6.8. Unreacted ligand was removed via Amicon spin concentrators and UV conjugated IBA-Thiol was then reacted with 5 equivalents of fluorescein-5-maleimide for 1 hour at RT. The UV coupled IgG$^{PSA}$ was then incubated on the antigen coated plate surfaces. The plates were washed to remove any unbound components using an automated plate washer (three cycles of 200 μL PBS with 0.05% Tween 20 at pH 7.4). The degree of UV immunoglobulin thiolation, via fluorescein-5-maleimide, for each sample was determined by incubating with a 1:5,000 dilution of HRP conjugated goat anti-fluorescein immunoglobulin (1.0 mg/mL stock) in BSA blocking buffer for 1 h. To assess the degree of UV immunoglobulin biotinylation for each sample the wells were incubated with a 1:10,000 dilution of streptavidin-HRP (1.0 mg/mL stock) in BSA blocking buffer for 1 h. Amplex red was added and fluorescent product formation was observed on a Molecular Devices SpectraMax M5 plate reader. Control experiments performed without IBA-ligand were used as background for the IBA-Biotin and IBA-Thiol detection measurements. The results are reported as relative fluorescence units (RFU). All data represents means (±SD) of triplicate experiments.

Determination of Average Number of UV Conjugations Via Size Exclusion Chromatography (SEC).

A Tosoh Biosciences G4000SW$_{XL}$ (7.8 mm ID×30 cm) size exclusion column was used to assess the average number of UV conjugations of IBA-FITC and IBA-Thiol, via fluorescein-5-maleimide, to the immunoglobulin over a range of UV energies (0-1.5 J/cm$^2$). Immunoglobulin samples were prepared as indicated, and 20 µL of each sample were analyzed on the SEC column. Each SEC run was achieved using a 25 min isocratic gradient of 50 mM PBS at pH 6.8 with 370 mM NaCl and 0.1% Tween 20. All samples were analyzed at 220 and 280 nm to detect immunoglobulin content and at 494 nm to detect covalently bound IBA-FITC and IBA-Thiol, via fluorescein-5-maleimide. Each absorbance spectrum was integrated on Chemstation LC software and used to calculate total immunoglobulin content and total nmoles of covalently bound fluorescein compared to a calibration curve to determine the average number of fluorescein conjugations per immunoglobulin.

Reactive Cysteine Quantification Using Ellman's Reagent.

To quantify the number of reactive thiol groups in solution 20 µL of sample was added to 50 µL of 2 mM Ellman's Reagent (5,5'-dithiobis(2-nitrobenzoic acid)) in 50 mM sodium acetate buffer, 100 µL of 1 M Tris at pH 8.0, and 130 µL of dH$_2$O. The mixture was incubated at RT, protected from light, for 20 min and absorbance was read at 412 nm ($\varepsilon$=13,600), 1 cm path length. A calibration curve was created using known dilutions of N-acetyl-L-cysteine (y=0.0008x, R$^2$=0.9983) shown in FIG. 33.

Results and Discussion.

Figure 33:
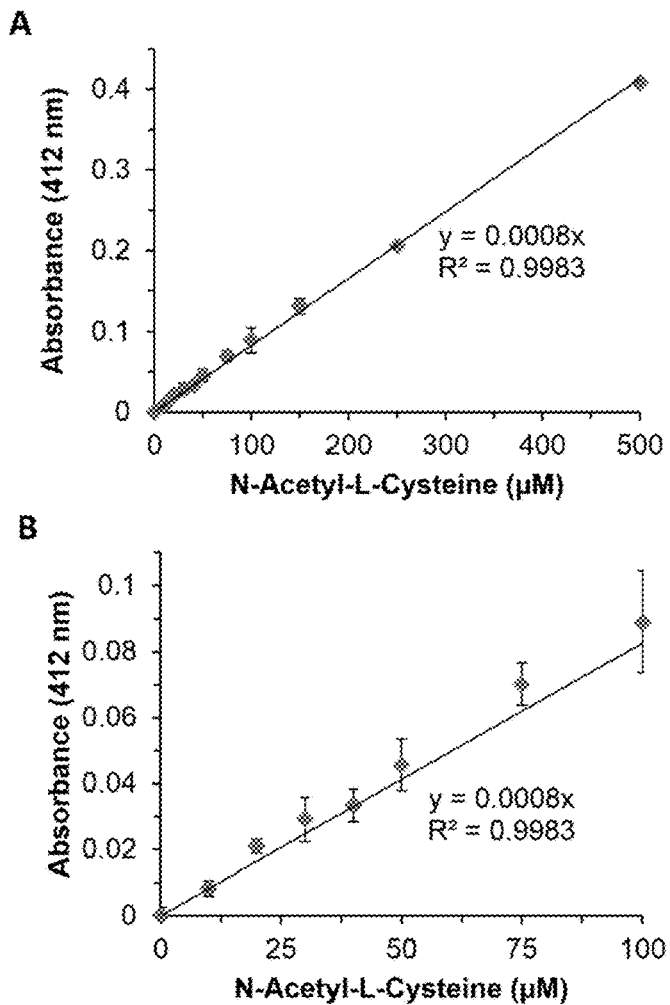
FIG. 33. Calibration curve utilizing N-acetyl-L-cysteine to quantify the number of reactive thiols by converting the 412 nm absorbance from the Ellman's reagent to known concentrations of thiol in solution. A) Demonstrates the full range of linearity using the Ellman's reagent with panel (B) showing a zoomed in view of the 0-100 μM lower range of detection linearity. Using this calibration curve, the concentration of reactive thiols was determined in the presence of various concentrations of ligand and over a range of UV energies and buffer conditions.
Figure 34:
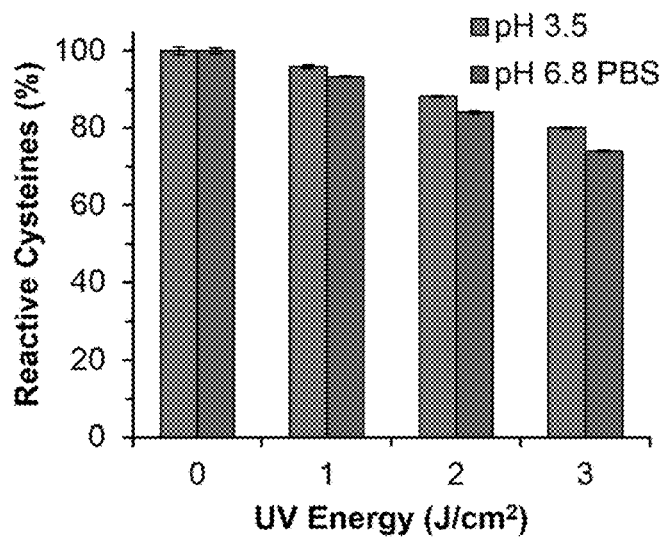
FIG. 34. Determination of the effects of UV energy exposure on IBA-Thiol reactivity at pH 3.5 and pH 6.8 in the absence of immunoglobulin. IBA-Thiol (300 μM) in a total volume of 30 μL was exposed to a range of UV energies from 0-3 J/cm$^2$. Ellman's reagent was used to quantify the amount of reactive thiols in solution normalized to the no UV energy sample. At increasing UV energy exposures the amount of reactive thiols present in solution decreased with only slightly reduced UV effect at pH 3.5 over pH 6.8. UV exposure at 254 nm is known to facilitate disulfide bond formation causing a reduction in reactive thiols in solution. This UV effect is highly dependent on the buffer conditions, pH (increasing disulfide bond formation at higher pH) and the presence of sensitizers. All data represents means (±SD) of triplicate experiments.
Figure 35:
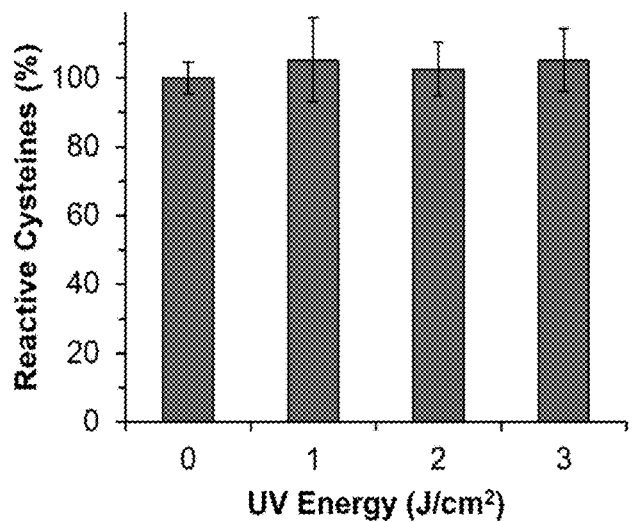
FIG. 35. Determination of the effects of UV energy exposure on IBA-Thiol reactivity in PBS at pH 6.8 in the presence of IgG$^{PSA}$. IBA-Thiol (300 μM) and IgG$^{PSA}$ (20 μM) in a total volume of 30 μL was exposed to a range of UV energies from 0-3 J/cm$^2$. Ellman's reagent was used to quantify the amount of reactive thiols in solution normalized to the no UV energy sample. At increasing UV energy exposures the amount of reactive thiols present in solution remained constant over the entire range of UV energies. The presence of IgG$^{PSA}$ reduced the formation of disulfide bonds at high UV energy exposures. All data represents means (±SD) of triplicate experiments FIG. 36. Determination of the rate of disulfide bond formation in PBS at (A) pH 6.8 and (B) pH 9. IBA-Thiol (300 μM) in a total volume of 30 μL was incubated in the indicated buffer and was allowed to react at room temperature, protected from light, for the indicated period of time. Ellman's reagent was used to quantify the amount of reactive thiols in solution normalized to the t=0 h sample. The rate of disulfide bond formation at pH 9 was much greater than at pH 6.8 with 85% and 2.7% reactive thiols remaining in solution after 24 h, respectively. All data represents means (±SD) of triplicate experiments.

We first evaluated the effect of UV energy exposure to the IBA-Thiol ligand used in the photocrosslinking reaction, in the presence and absence of immunoglobulin. Both IBA and thiol moieties are UV reactive and can function as sensitizers upon UV exposure. Therefore, it is important to demonstrate that the thiol remains active post UV exposure and that the IBA/NBS interaction still results in efficient photocrosslinking. A fixed concentration of IBA-Thiol was exposed to a range of UV energies (0-3 J/cm$^2$) and reactive thiol groups were quantified utilizing Ellman's Reagent, a chromogenic substrate that absorbs light at 412 nm ($\varepsilon$=13,600) upon binding to thiols (FIG. 33). In the absence of immunoglobulin, 3 J/cm$^2$ of UV energy resulted in 74% reactive thiol moieties remaining in solution (FIG. 34). When IBA-Thiol (300 µM) and immunoglobulin (20 µM) are both present in solution the same UV energy exposure results in no appreciable reduction in thiol reactivity (FIG. 35). This result is in part due to a UV shielding effect by the immunoglobulins in solution preventing full exposure to the IBA-Thiol ligand as well as much of the UV energy being adsorbed and transferred into the IBA/immunoglobulin crosslinking reaction itself.

Figure 36:
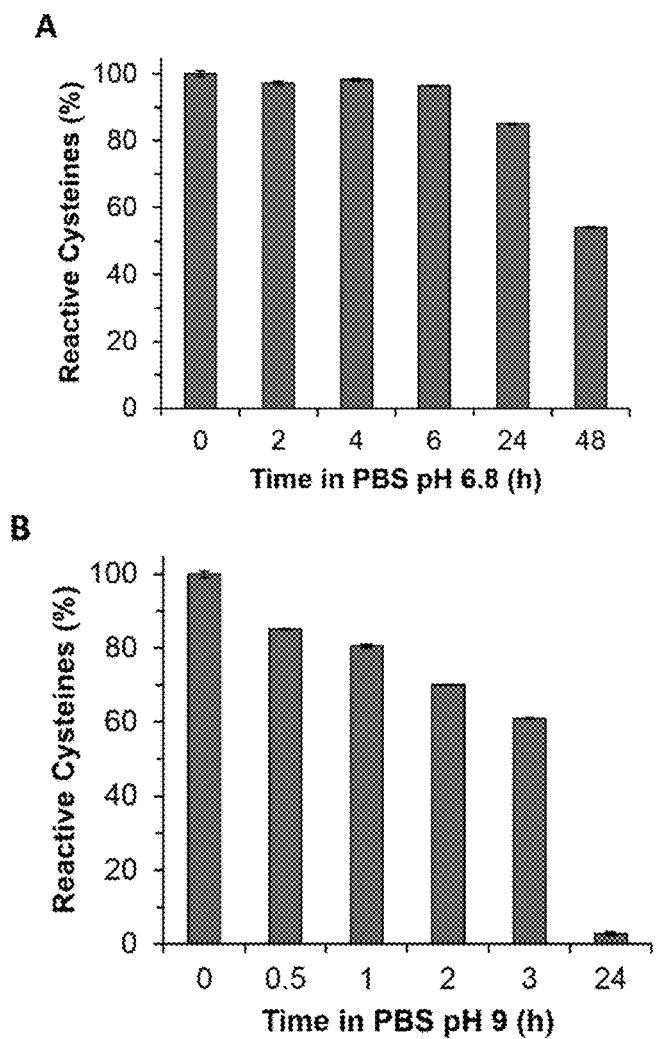

It was then necessary to test the UV effects of the IBA-Thiol conjugation to the immunoglobulin to verify that the ligand does not have a negative effect on the immunoglobulin antigen binding activity upon UV exposure. To simultaneously test for IBA-Thiol crosslinking to the immunoglobulin and thiol reactivity post UV exposure maleimide-fluorescein was utilized. An immunoglobulin against prostate specific antigen (IgG$^{PSA}$) was used to validate the site-specific conjugation of IBA-Thiol to immunoglobulin NBS. IgG$^{PSA}$ was exposed to increasing UV energies (0-5 J/cm$^2$) in the presence of a saturating concentration of IBA-Thiol (300 µM) in PBS pH 6.8 to allow for covalent photocrosslinking between the IBA and NBS. PBS pH 6.8 was selected due to the reduced rate of disulfide bond formation providing for 97% free thiols remaining after 6 h at room temperature and 85% remaining after 24 hours (FIG. 36). This pH also provides for efficient IBA/NBS binding and maintains a high level of site-specific photocrosslinking efficiency.

Figure 29:
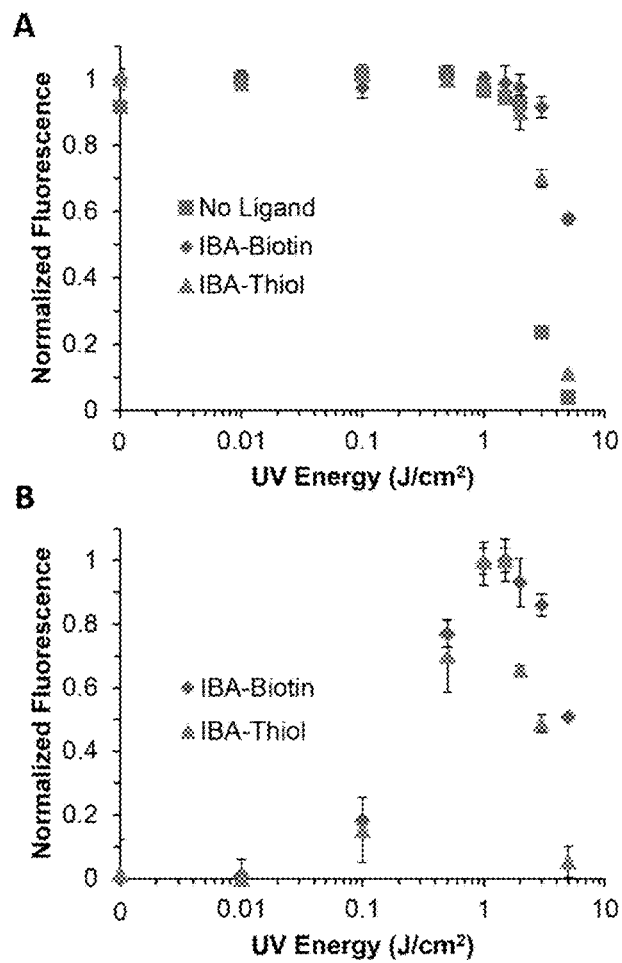
FIG. 29. A) The effects of UV energy exposure on antigen binding activity combined with Fc recognition as determined by an ELISA assay. UV exposed IgG$^{PSA}$, in the presence or absence of 300 μM IBA-Biotin or IBA-Thiol, via subsequent maleimide-fluorescein reaction, was allowed to bind to surface immobilized PSA. The total amount of bound immunoglobulin was quantified using an Fc-specific, HRP conjugated immunoglobulin. B) Photocrosslinking efficiency of IBA-Biotin or IBA-Thiol to IgG$^{PSA}$ at the NBS was determined by an indirect ELISA assay, where the total biotinylation or thiolation, via reacted maleimide-fluorescein, was detected post binding to surface immobilized PSA by streptavidin-HRP or an anti-fluorescein HRP conjugated immunoglobulin. All data represents means (±SD) of triplicate experiments.

The excess IBA-Thiol was removed via membrane filtration and the UV-exposed immunoglobulins were then incubated with a 5-fold excess of maleimide-fluorescein to react to all conjugated reactive thiols. The conjugated immunoglobulins were then allowed to bind to surface immobilized prostate specific antigen (PSA). Total immunoglobulin activity was determined by an Fc-specific HRP conjugated secondary immunoglobulin (FIG. 29A) and IBA-Thiol photocrosslinking efficiency was determined by an anti-fluorescein HRP conjugated secondary immunoglobulin (FIG. 29B). The IBA-Thiol ligand provides some UV shielding that protects the immunoglobulin from damage at high UV energies similarly to IBA-Biotin with an immunoglobulin activity level of 95% at 1.5 J/cm$^2$ UV (FIG. 29A and FIG. 11). The photocrosslinking efficiency and thiol reactivity post UV exposure follows a similar trend as IBA-Biotin with an increased UV sensitivity above 1.5 J/cm$^2$. These results demonstrate that IBA-Thiol was successfully photocrosslinked to IgG$^{PSA}$ with the thiol moiety and antigen binding remaining active post conjugation.

Figure 30:
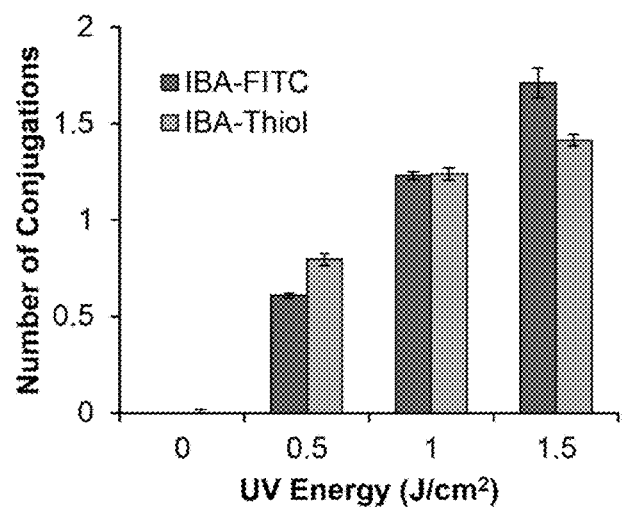
FIG. 30. The effect of UV energy on the average number of conjugations per immunoglobulin of IBA-FITC and IBA-Thiol, via maleimide-fluorescein detection. Number of conjugations was determined from absorbance at 494 nm SEC peak integrations at fixed ligand and immunoglobulin concentrations of 300 μM and 20 μM, respectively. All data represents means (±SD) of triplicate experiments.
Figure 31:
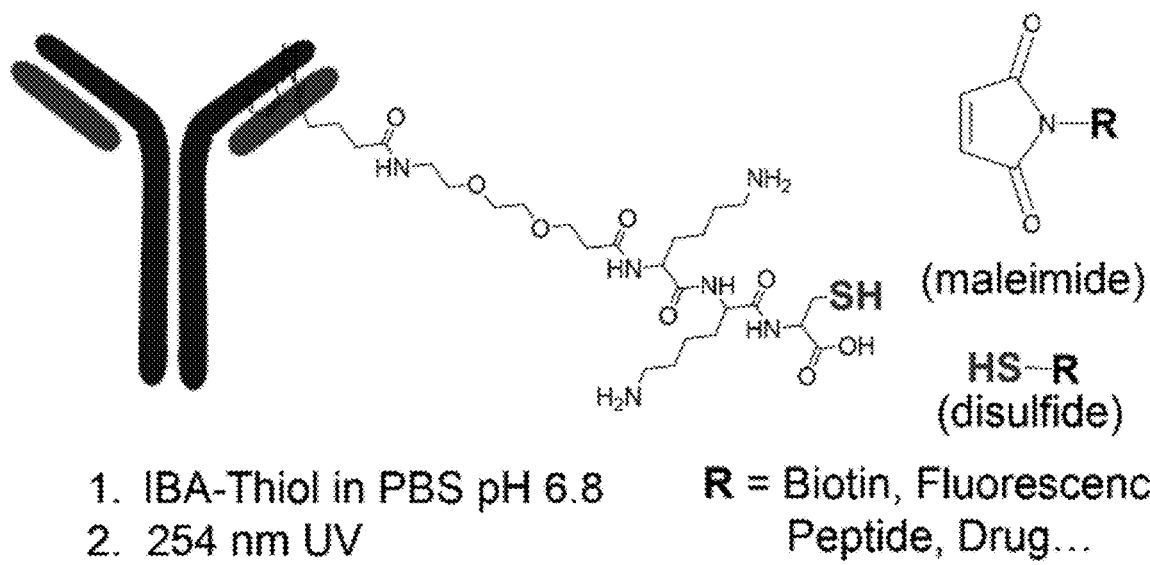
FIG. 31. Schematic diagram of IBA-thiol conjugated immunoglobulin reacting with a reactive group (a maleimide or a sulfide) to for a conjugate, according to various embodiments.

The effect of UV energy on the average number of IBA conjugations per immunoglobulin was then evaluated. IBA-FITC at 300 µM (FIG. 12) was incubated with IgG$^{PSA}$, providing for complete non-covalent association of IBA-FITC to all NBS, and was then exposed to the indicated UV energies. The IBA-FITC conjugated immunoglobulin was then injected on a size exclusion chromatography (SEC) column where non-conjugated IBA-FITC ligand eluted separately from the immunoglobulin conjugate. Utilizing a fluorescein calibration curve, based on SEC elution peak integrations of known amounts of fluorescein (494 nm) the average number of IBA-FITC conjugations per immunoglobulin was calculated (FIG. 30). Increasing UV energy resulted in an increase in the number of conjugations, reaching a maximum of 1.71 conjugations per immunoglobulin at 1.5 J/cm$^2$ UV exposure. Since the IgG$^{PSA}$ immunoglobulin activity was greatly reduced above 1.5 J/cm$^2$ higher UV energies were not investigated. No crosslinking was observed in the absence of IBA or in the absence of UV energy.

A similar analysis of the average number of active IBA-Thiol conjugations per immunoglobulin at increasing UV energies was also investigated. Immunoglobulin was incubated with a saturating concentration of IBA-Thiol and then exposed to the indicated UV energies. Maleimide-fluorescein was again employed to react to all reactive thiol groups and the mixture was analyzed via SEC injection. Utilizing the same peak integration method and fluorescein calibration curve, the number of reactive IBA-Thiol conjugations was quantified, reaching a maximum of 1.41 conjugations at 1.5 J/cm$^2$ UV (FIG. 30). The average number of IBA-FITC and IBA-Thiol conjugations per immunoglobulin followed a very similar UV energy dependence with very comparable conjugation efficiencies (Table 4 above). This result demonstrates that the UV energies necessary to provide for efficient photocrosslinking have no effect on thiol reactivity or IBA/NBS photocrosslinking. Taken together, these results demonstrate that IBA-Thiol can be photocrosslinked to the immunoglobulin NBS providing for the site-specific incorporation of an orthogonally reactive thiol moiety to the immunoglobulin.

Conclusion.

Figure 37:
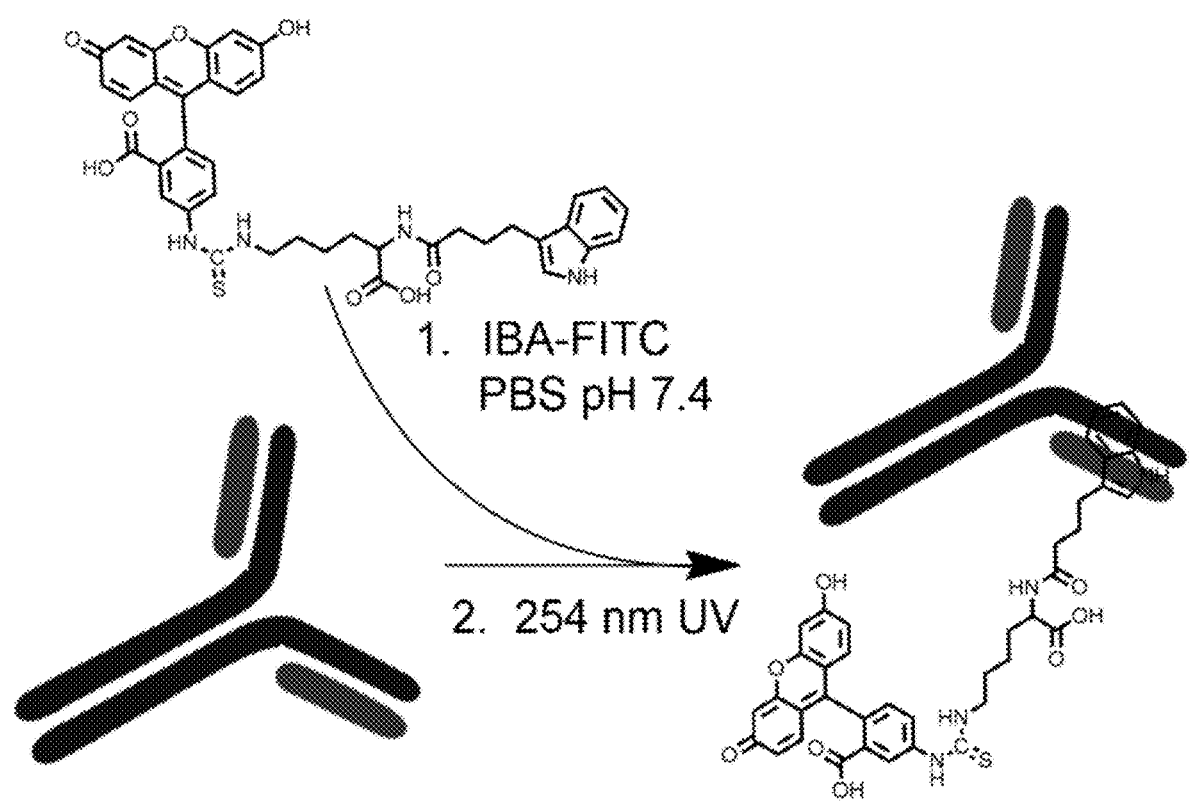
FIG. 37. This is a schematic representation of the method for UV photocrosslinking of IBA-FITC to immunoglobulins at the NBS. Immunoglobulins associate with IBA-FITC at the NBS, and upon UV exposure a covalent bond forms between IBA and the immunoglobulin. The site-specific conjugation of the immunoglobulin through its NBS preserves immunoglobulin's antigen binding activity.

In this example we have particularly demonstrated the site-specific functionalization of $IgG^{PSA}$ with biotin (IBA-Biotin), fluorescein (IBA-FITC, see FIG. 37), and reactive thiol ligand (IBA-Thiol) using the UV-NBS photocrosslinking method. Through the coupling of maleimide-fluorescein the proof of concept for site-specific photocrosslinking of reactive thiol groups to the immunoglobulin NBS via an IBA functionalized ligand has been established. Utilizing the IBA-Thiol ligand allows for an efficient means of site-specifically conjugating UV sensitive functionalities via subsequent maleimide or disulfide bond formation that would otherwise not have been amenable by the UV-NBS photocrosslinking method.

Example 3. UV-NBS Photocrosslinking of Biotin

Figure 40:
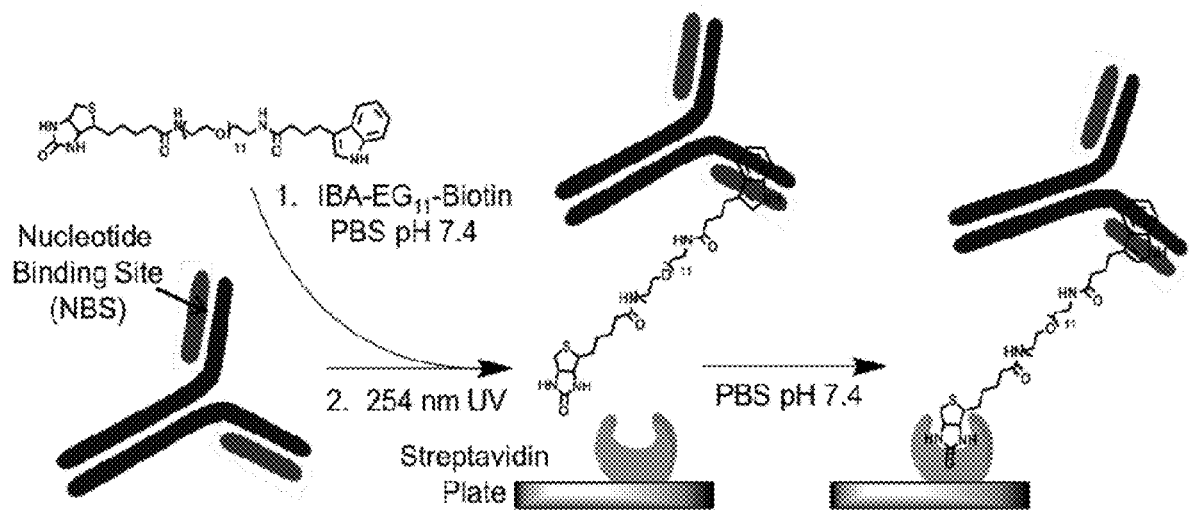
FIG. 40. Schematic representation of the UV-NBS$^{Biotin}$ immobilization method. Immunoglobulins associate with IBA-EG$_{11}$-Biotin ligand at the NBS, and upon UV exposure a covalent bond forms between IBA and the immunoglobulin. The IBA-EG$_{11}$-Biotin functionalized immunoglobulin then binds to a streptavidin functionalized plate, tethering the immunoglobulin to the surface. The oriented, site-specific conjugation of the immunoglobulin through its NBS preserves immunoglobulin's antigen binding activity.

Here, we describe an alternate photochemistry based NBS-specific immunoglobulin immobilization method that utilizes biotin for oriented immobilization to streptavidin-functionalized surfaces (UV-NBS$^{Biotin}$, FIG. 40). We predicted that site-specifically conjugating a biotin molecule to the immunoglobulin NBS prior to immobilization would allow for nearly 100% immunoglobulin functionalization to overcome the poor immobilization efficiency of the previously reported UV-NBS method while still maintaining maximum immunoglobulin activity.

1.

Materials. IBA, Biotin N-hydroxysuccinimide ester (NHS-Biotin), N,N-Diisopropylethylamine (DIEA), were purchased from Sigma-Aldrich (St. Louis, Mo.). Streptavidin-HRP and HRP-conjugated IgG Fcγ specific goat anti-mouse were purchased from Jackson ImmunoResearch (West Grove, Pa.). Heat shock isolated bovine serum albumin (BSA), Amicon Ultra centrifugal filters (0.5 mL, 10K) and Coomassie R-250 were purchased from EMD Millipore (Billerica, Mass.). Amplex Red Assay Kit was purchased from Invitrogen (Grand Island, N.Y.). Maleic anhydride amine reactive 96-well plates and streptavidin coated 96-well plates were purchased from Thermo Scientific (Rockford, Ill.). NovaPEG Rink Amide resin, and all other amino acids were purchased from Novabiochem (Billerica, Mass.). Fmoc-N-amido-dPEG$_2$-acid was purchased from Quanta Biodesign (Powell, Ohio). Tris-gly running buffer, transfer buffer, and tris buffered saline (TBS) were purchased from Boston Bioproducts (Ashland, Mass.). Mouse anti-PSA ($IgG^{PSA}$ capture immunoglobulin, clone: B731M), mouse anti-PSA (det-$IgG^{PSA}$ detection immunoglobulin, clone: 5A6) and purified free prostate specific antigen (PSA) were purchased from Meridian Life Science, Inc. (Memphis, Tenn.).

2. Photocrosslinking of IBA-Conjugated Ligands (IBA-Ligand) to Immunoglobulins.

All immunoglobulins undergoing photocrosslinking were purchased as purified immunoglobulins with no protein stabilizers. Sodium azide, a very UV reactive preservative, and other small molecule additives were removed prior to UV exposure via membrane filtration. Immunoglobulins were incubated with the IBA-ligands for 1 h prior to UV exposure at room temperature (RT). Control over the UV energies delivered to the samples was achieved using a Spectroline UV Select Series Crosslinker from Spectronics at a wavelength of 254 nm.

3. Assessing Antigen Binding Activity, Fc Stability, and Biotinylation of the Immunoglobulin Via ELISA.

Antigen coated ELISA plates were generated by adsorbing PSA (10 nM or 0.34 mg/mL) to high binding 96-well ELISA plates in 0.05 M carbonate-bicarbonate coating buffer at pH 9.6 for 2 h at RT. The plates were washed to remove any unbound components using an automated plate washer with three cycles of 200 μL PBS with 0.05% Tween 20 at pH 7.4 (MDS Aquamax 2000). All plate surfaces were then blocked with BSA blocking buffer (200 μL of 5% BSA in PBS pH 7.4 with 0.1% Tween 20) for 1 h. Antigen Binding Activity and Fc Stability: The $IgG^{PSA}$ capture immunoglobulin was exposed to UV in the presence or absence of 300 μM IBA-EG$_{11}$-Biotin and was then incubated on the antigen coated plates. The wells were then incubated with a 1:5,000 dilution of HRP-anti-Fc immunoglobulin (1.0 mg/mL stock) in BSA blocking buffer for 1 h to quantify the total amount of antigen bound immunoglobulin (active Fc). $IgG^{PSA}$ Biotinylation: To assess the degree of UV biotinylation for each sample, the antigen bound IBA-EG$_{11}$-Biotin UV exposed $IgG^{PSA}$ immunoglobulin wells were incubated with a 1:10,000 dilution of streptavidin-HRP (1.0 mg/mL stock) in BSA blocking buffer for 1 h. Amplex red, the HRP substrate, was added and fluorescent product formation was observed on a Molecular Devices SpectraMax M5 plate reader (ex. 570 nm, em. 592 nm) for all ELISA assays. Control experiments performed without IBA-EG11-Biotin were used as background for the biotinylation detection measurements. The results are reported as relative fluorescence units (RFU). All data represents means (±SD) of triplicate experiments.

4. Determination of Average Number of UV Conjugations Via Size Exclusion Chromatography (SEC).

A Tosoh Biosciences G4000SW$_{XL}$ (7.8 mm ID×30 cm) size exclusion column was used to assess the average number of IBA-FITC conjugations to the immunoglobulin over a range of UV energies (0-1.5 J/cm$^2$). Immunoglobulin samples were prepared as indicated, and 20 μL of each sample were analyzed on the SEC column. Each SEC run was achieved using a 25 min isocratic gradient of 50 mM PBS at pH 6.8 with 370 mM NaCl and 0.1% Tween 20. All samples were analyzed at 220 and 280 nm to detect immunoglobulin content and at 494 nm to detect covalently bound IBA-FITC. Each absorbance spectrum was integrated on Chemstation LC software and used to calculate total immunoglobulin content and total nmoles of covalently bound IBA-FITC compared to a calibration curve (y=836.94x, R$^2$=0.9876). The nmoles of FITC divided by the nmoles of immunoglobulin gives the average number of IBA-FITC conjugations per immunoglobulin.

5. Western Blot Analysis for Determination of the Photocrosslinking Site.

$IgG^{PSA}$, at 20 μM, was incubated with excess IBA-EG11-Biotin (300 μM) in PBS buffer at pH 7.4 and exposed to the indicated amount of UV energy (0-1.5 J/cm$^2$). The samples were run on a 10% SDS-PAGE gel with a tris-glycine running buffer under reducing conditions at 110 V for 1 h and were transferred to a nitrocellulose membrane at 110 V for 90 min in a 10% MeOH transfer buffer. The membrane was blocked with 10% dry milk in TBS for 1 h and was then blotted with 1:10,000 dilution of streptavidin-HRP for 1 h at RT. A chemiluminescent HRP substrate was used to detect the location where IBA-EG$_{11}$-Biotin was covalently conjugated to the immunoglobulin. The SDS-PAGE gel was coomassie blue stained in a solution of 10% acetic acid, 20% methanol, 0.15% Coomassie R-250 for 30 min and destained in a solution of 20% acetic acid, 20% methanol, 60% D.I.

water for 1.5 h. Control experiments performed in the absence of UV exposure, or in the absence of IBA-EG11-Biotin did not yield any detectable bands.

6. UV-NBS$^{Biotin}$ Immunoglobulin Immobilization Method.

IgG$^{PSA}$ incubated with 300 μM IBA-EG$_{11}$-Biotin in PBS was exposed to 1 J/cm$^2$ of UV energy. The unbound IBA-EG$_{11}$-Biotin was removed via membrane filtration. The purified, biotinylated IgG$^{PSA}$ was then incubated on streptavidin coated ELISA plates in PBS pH 7.4 for 2 h at RT. In all cases, unbound immunoglobulin was then washed using an automated plate washer. Immunoglobulin immobilized wells were then blocked with BSA blocking buffer for 1 h to prevent non-specific adhesion/interactions.

7. Non Site-Specific Immobilization Methods.

Physical adsorption immobilization method: was carried out by incubating immunoglobulin on high bind ELISA plate surfaces in 0.05 M carbonate-bicarbonate coating buffer at pH 9.6 for 2 h at RT. ε-NH$_3^+$ immobilization method: lysine side-chains present on the immunoglobulin surface were reacted to amine reactive maleic anhydride 96-well plates for 2 h at RT in PBS buffer at pH 8.0. Any remaining reactive sites were then quenched with 50 mM Tris buffer with 100 mM NaCl at pH 8.0 for 1 h. NHS-Biotin immobilization method: immunoglobulin was biotinylated with NHS-Biotin following the manufacturer suggested protocol and unreacted NHS-Biotin was removed via membrane filtration prior to incubation on streptavidin coated plate surfaces in BSA blocking buffer for 2 h at RT. All surfaces were then washed and blocked using BSA blocking buffer for 1 h.

8. Determination of Total Immunoglobulin Content of Immunoglobulin Immobilized Surfaces.

Quantification of the total surface immobilized immunoglobulin for each of the four immobilization techniques with initial immunoglobulin amounts of 0-50 fmole (0-0.5 nM) were performed using an HRP conjugated Fc-specific secondary immunoglobulin from goat at a 1:5,000 dilution (1.0 mg/mL stock) in BSA blocking buffer for 1 h. Amplex red was used as the enzymatic substrate and the results are reported as RFU. The resulting immunoglobulin immobilization signal at different starting immunoglobulin amounts was fit by linear regression. The slope of the linear regression line was determined to be the immunoglobulin immobilization efficiency for each of the immobilization methods. Control experiments performed without immobilized immunoglobulin were used as background.

9. Determination of Antigen Detection Efficiency, Assay Sensitivity and Limit of Detection.

The antigen detection capabilities for all four immobilization methods were determined by ELISA. Briefly, IgG$^{PSA}$ immobilized surfaces (1 or 5 fmole, 0.01 or 0.05 nM, of initial immunoglobulin) were incubated with PSA (0-1,000 fmole or 0-10 nM) in 100 μL of BSA blocking buffer for 1.5 h. Unbound PSA was washed and the wells were incubated with a 1:2,500 dilution of det-IgG$^{PSA}$ (5A6, 1.0 mg/mL stock) in BSA blocking buffer for 1 h. An Fc-specific HRP conjugated immunoglobulin (1:2,500 dilution) was then used to detect the presence of the IgG$^{PSA}$ detection immunoglobulin bound to PSA. Amplex red was then added and fluorescent product formation was observed, results are reported as RFU. The resulting antigen detection signal vs. amount of antigen plots were fit by natural log regression. Sensitivity was determined from the coefficient of the natural log multiplier from the regression line. The limit of detection (LOD) for each immobilization method was determined to be the antigen concentration at 3 standard deviations to the mean of the zero PSA standard. Control experiments performed without PSA, and without detection immunoglobulin were used as background for the antigen detection measurements.

Results and Discussion

1. Effect of UV Energy on Immunoglobulin Binding Activity and Fc Recognition.

Figure 41:
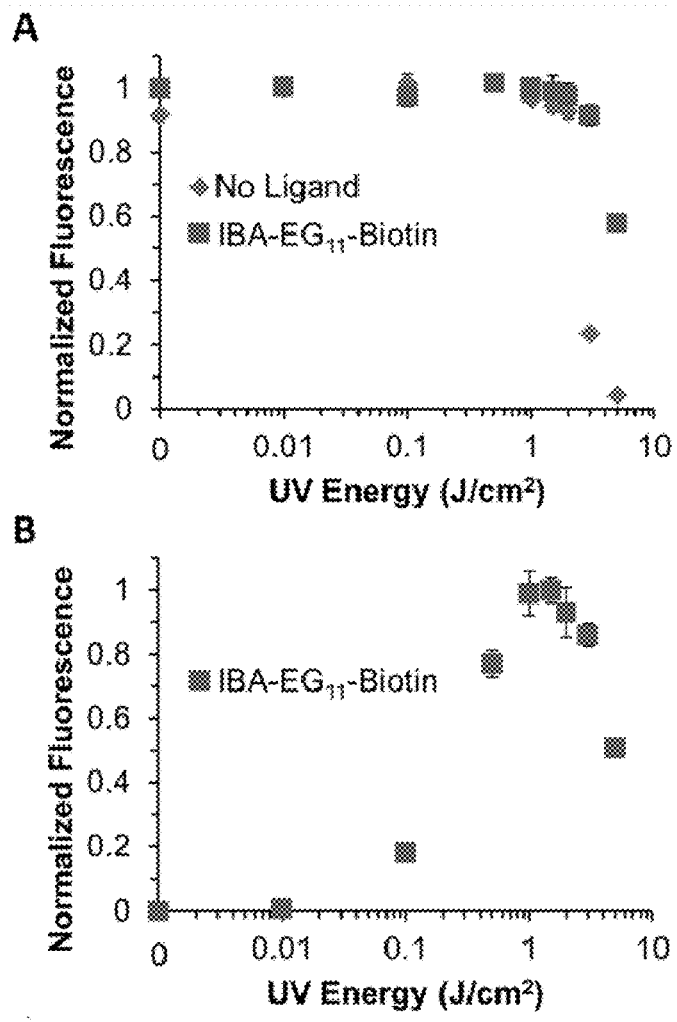
FIG. 41. The effects of UV energy exposure on antigen binding activity, Fc recognition and biotinylation efficiency as determined by ELISA assays. A) UV exposed IgG$^{PSA}$, in the presence or absence of 300 μM IBA-EG$_{11}$-Biotin, was allowed to bind to surface immobilized PSA and the total amount of bound immunoglobulin was detected using an Fc-specific, HRP conjugated immunoglobulin. B) Photocrosslinking efficiency of IBA-EG$_{11}$-Biotin to the immunoglobulin at the NBS was determined by an indirect ELISA assay, where the total biotinylation levels of IgG$^{PSA}$ were detected by streptavidin-HRP after binding to surface immobilized PSA. All data represents means (±SD) of triplicate experiments.
Figure 45:
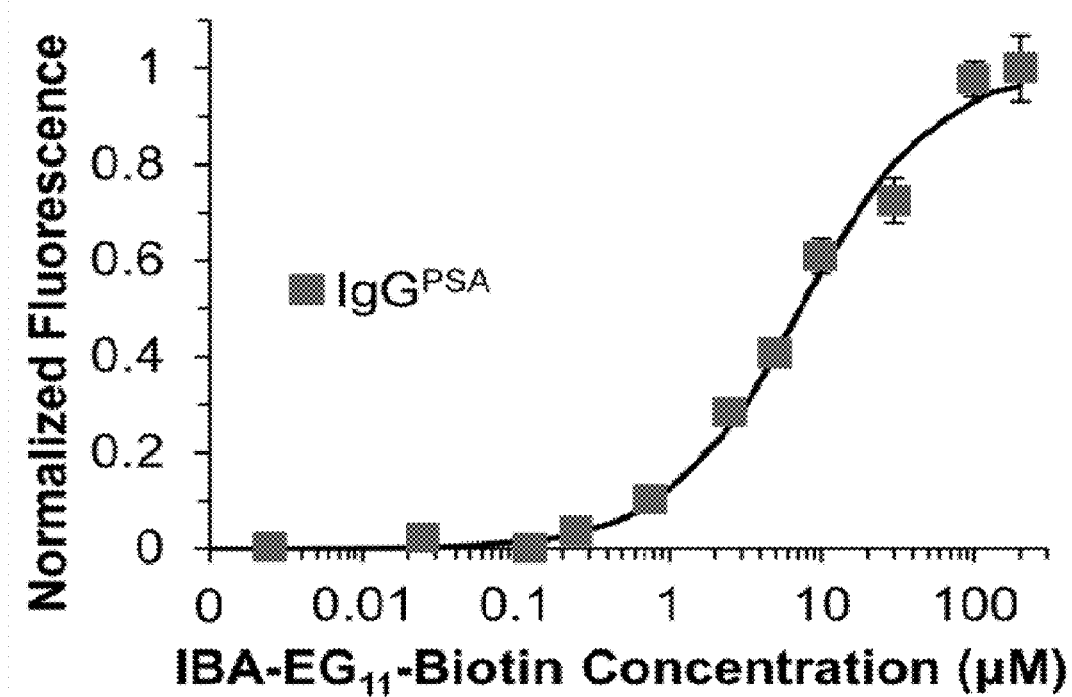
FIG. 45. Effect of IBA-EG$_{11}$-Biotin concentration on photocrosslinking efficiency. IgG$^{PSA}$ was incubated with increasing concentrations of IBA-EG$_{11}$-Biotin (0-200 μM) and exposed to 1 J/cm$^2$ UV. IBA-EG$_{11}$-Biotin photocrosslinking efficiency at the NBS was determined by directly adsorbing the biotinylated immunoglobulins to a high binding ELISA plate surface and using streptavidin-HRP as a reporter. All data represents means (±SD) of triplicate experiments. The incubated IBA-EG$_{11}$-Biotin concentration plays a critical role in the efficiency of photocrosslinking since it determines the extent to which all NBS are bound to IBA prior to UV exposure. Increasing the ligand concentration resulted in an increase in the UV crosslinking efficiency reaching a plateau at ~100 μM. The curve was then fit to a sigmoid and an EC$_{50}$ (half maximum effective concentration) value was determined. The EC$_{50}$ value for IgG$^{PSA}$ was 7.1±0.52 μM, which was in-line with previous EC$_{50}$ and K$_d$ values of various immunoglobulins tested (1-8 μM). Based on the photocrosslinking efficiency of IBA-EG$_{11}$-Biotin we have verified that a concentration ≥100 μM is sufficient to allow for maximum photocrosslinking.

We first evaluated the effect of increasing UV energies on IBA photocrosslinking to the immunoglobulin by using IBA-EG$_{11}$-Biotin via an ELISA assay. UV exposure initiates the site-specific photocrosslinking of the IBA-ligand to the immunoglobulin NBS but can potentially have damaging effects to the antigen recognition site as well as Fc structure. For this reason, the effects of UV exposure to the IgG$^{PSA}$ were evaluated to ensure immunoglobulin activity was preserved at the UV exposures necessary to utilize the UV-NBS$^{Biotin}$ method. IgG$^{PSA}$ was exposed to increasing UV energies (0-5 J/cm$^2$) in the presence and absence of a saturating concentration of IBA-EG$_{11}$-Biotin (300 μM) in PBS pH 7.4 (FIG. 45). PSA was directly immobilized onto high binding ELISA plates through physical adsorption. The UV-exposed IgG$^{PSA}$ was then incubated on the plate surface and allowed to bind to PSA. Both antigen recognition and Fc stability were assessed simultaneously by binding of an HRP conjugated Fc-specific secondary immunoglobulin, evaluating the total amount of antigen-bound immunoglobulin at increasing UV energies. In this assay, a reduction in the signal intensity at high UV energies is indicative of damage to either the antigen binding sites preventing IgG$^{PSA}$ from binding its surface immobilized antigen or damage to the Fc region preventing detection by the Fc-specific HRP conjugated secondary immunoglobulin. Our results demonstrated nearly no observable reduction in immunoglobulin antigen binding activity or Fc recognition up to UV energies of 2.0 J/cm$^2$, with a slight increase in UV damage to the immunoglobulin in the absence of IBA-EG$_{11}$-Biotin (FIG. 41A). This result was expected since the presence of IBA-EG$_{11}$-Biotin in solution effectively screens the immunoglobulin from full exposure by partially adsorbing the UV energy. These results demonstrate that UV energies <2.0 J/cm$^2$ can be utilized during the UV-NBS$^{Biotin}$ immobilization of IgG$^{PSA}$ as there is minimal impact on both antigen binding activity and recognition of the immunoglobulin Fc by secondary immunoglobulins at these UV energies.

2. Determination of the Optimal UV Energy for IBA-EG$_{11}$-Biotin Photocrosslinking.

To determine the photocrosslinking efficiency of IBA-EG$_{11}$-Biotin to IgG$^{PSA}$, photocrosslinked immunoglobulin was incubated on plates coated with antigen and the degree of immunoglobulin biotinylation was determined by quantifying streptavidin-HRP binding. IBA-EG$_{11}$-Biotin photocrosslinking efficiency increased with increasing UV energy, with a maximum immunoglobulin biotinylation occurring between 1.0-2.0 J/cm$^2$ (FIG. 41B). A plateau in immunoglobulin biotinylation was observed that is indicative of a specific conjugation site becoming saturated. Since this assay did not depend upon Fc recognition for detection of antigen bound immunoglobulin it was determined that UV damage at the immunoglobulin antigen recognition sites, inhibiting immunoglobulin binding to the surface, was the main contributor to the decline in the biotinylation signal intensity at UV energies >2.0 J/cm$^2$. Based on the results presented in these two ELISA assays (FIG. 41A, 41B) we determined 0.5-1.5 J/cm$^2$ to be an effective UV exposure range that can be used for the efficient photocrosslinking of IBA-EG$_{11}$-Biotin to IgG$^{PSA}$, without reducing antigen binding or Fc activity. This UV range was consistent with our previous results.

3. Effect of UV Energy on the Number of Conjugations Per Immunoglobulin.

Figure 42:
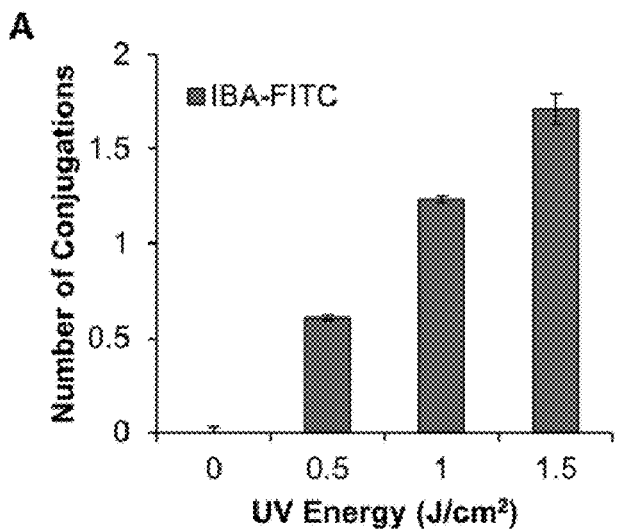
FIG. 42. The effect of UV energy on the average number, and location, of IBA-FITC conjugations per immunoglobulin. A) Number of conjugations was determined from absorbance at 494 nm SEC peak integrations at fixed ligand and immunoglobulin concentrations of 300 μM and 20 μM, respectively. All data represents means (±SD) of triplicate experiments. B) Western blot analysis of UV-NBS photocrosslinking site on IgG$^{PSA}$. IBA-EG$_{11}$-Biotin was photocrosslinked to the immunoglobulin by exposure to UV energy from 0-1.5 J/cm$^2$ in PBS buffer. SDS-PAGE was run under reducing conditions and the proteins were transferred to a nitrocellulose membrane. The SDS-PAGE gel was stained by coomassie blue. Streptavidin-HRP was used to probe for covalently conjugated IBA-EG$_{11}$-Biotin. Blotted film shows that biotin tag only appears on the immunoglobulin light chain.
Figure 42:
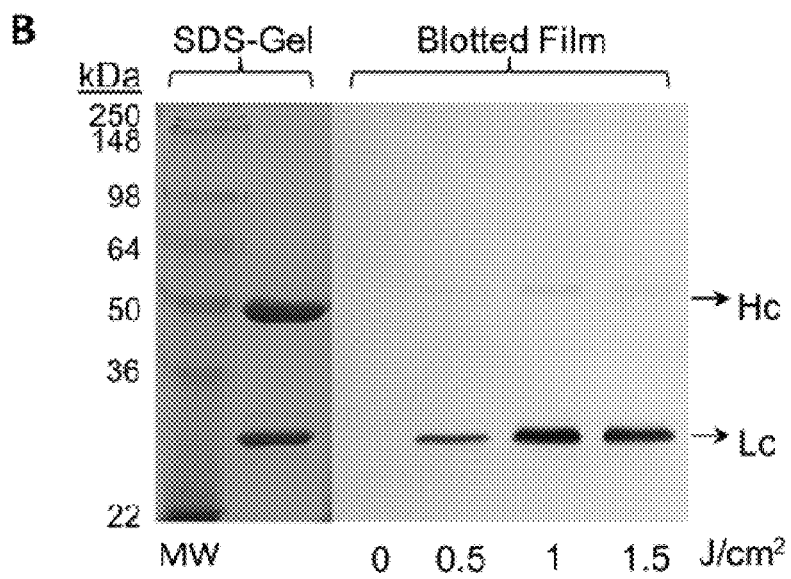

When utilizing the UV-NBS photocrosslinking method we anticipate a maximum of two IBA-ligand conjugations per immunoglobulin as there are two NBS per immunoglobulin. IBA-FITC was selected to quantify the average number of conjugations per immunoglobulin (FIG. 45). FITC was selected as it has a maximum absorbance (494 nm) well outside the range of typical protein adsorption (220 and 280 nm) allowing for accurate quantitation of the number of conjugations. IgG$^{PSA}$ was exposed to increasing UV energies in the presence of saturating levels of IBA-FITC (300 μM), providing for complete non-covalent association of IBA-FITC to all NBS prior to UV exposure (FIG. 42A). The IBA-FITC conjugated immunoglobulin was then injected on a size exclusion column to effectively separate non-conjugated IBA-FITC ligand from the conjugated immunoglobulin. By integrating the 494, 220 and 280 nm elution profiles and correlating the values to molar calibration curves, the average number of IBA-FITC conjugations per immunoglobulin was calculated by dividing nmoles of FITC by nmoles of immunoglobulin injected on the column (FIG. 42A). Increasing UV energy resulted in an increase in the number of conjugations, reaching a maximum of 1.71 conjugations per immunoglobulin at 1.5 J/cm$^2$ UV exposure. For maximum surface immobilization efficiency a single biotin per immunoglobulin was desired and therefore a UV energy of 1.0 J/cm$^2$ was selected, with an average of 1.23±0.02 conjugations per immunoglobulin. Since the immunoglobulin biotinylation occurs site-specifically and there are only two NBS sites that conjugation can occur at, we estimate that >90% of the IgG$^{PSA}$ possesses at least a single biotin conjugation at an average of 1.23 biotins per immunoglobulin. No crosslinking was observed in the absence of IBA or in the absence of UV energy.

4. Determination of the Photocrosslinking Site by Western Blot Analysis.

Figure 46:
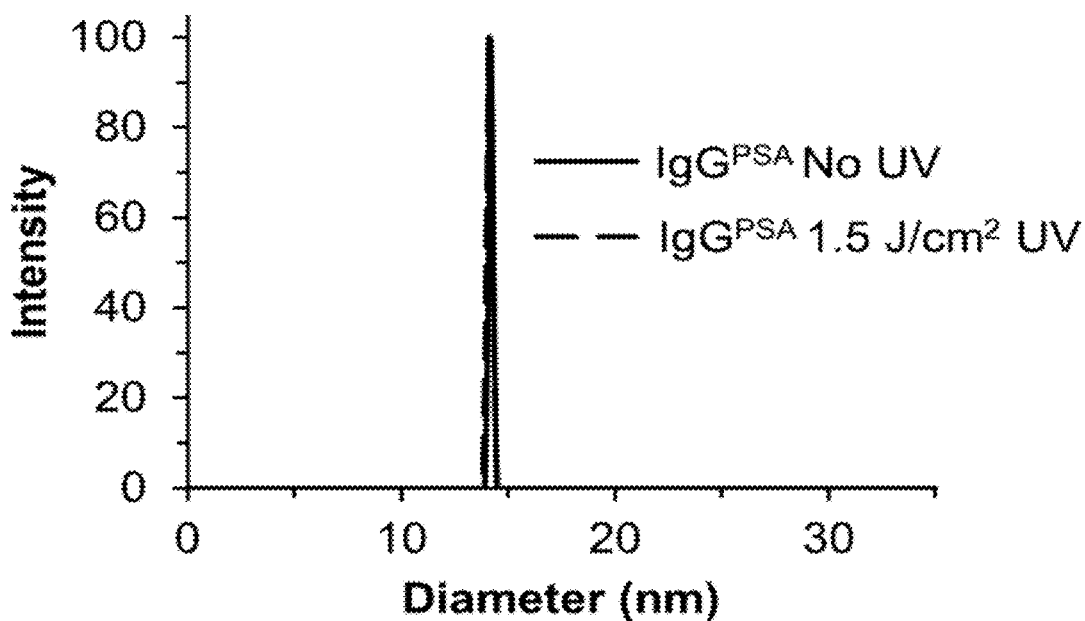
FIG. 46. Dynamic light scattering (DLS) of mouse IgG$^{PSA}$ before and after UV exposure. The hydrodynamic diameter of monomeric immunoglobulin is approximately 14 nm before UV exposure, and remains the same after 1.5 J/cm$^2$ UV indicating no inter-immunoglobulin crosslinking occurred. DLS experiments were carried out using 100⏀ of 100 nM IgG$^{PSA}$ in PBS at pH 7.4. Data was collected on a Brookhaven ZetaPlus instrument and was averaged from five 1 minute measurements.

To verify the specificity of IBA for the NBS site on IgG$^{PSA}$ a western blot analysis was carried out with IBA-EG$_{11}$-Biotin photocrosslinked immunoglobulin under reducing conditions. The HRP-streptavidin probed film established that biotinylation occurred selectively to the immunoglobulin light chain, with the yield of conjugation being dependent on the amount of UV energy exposure (FIG. 42B). This result was consistent across all other immunoglobulins that have been tested. The IgG$^{PSA}$ immunoglobulin was also evaluated by dynamic light scattering post 1.5 J/cm$^2$ UV exposure to verify that UV exposure did not cause inter-immunoglobulin crosslinking or effect the global immunoglobulin structure (FIG. 46).

5.

Figure 47:
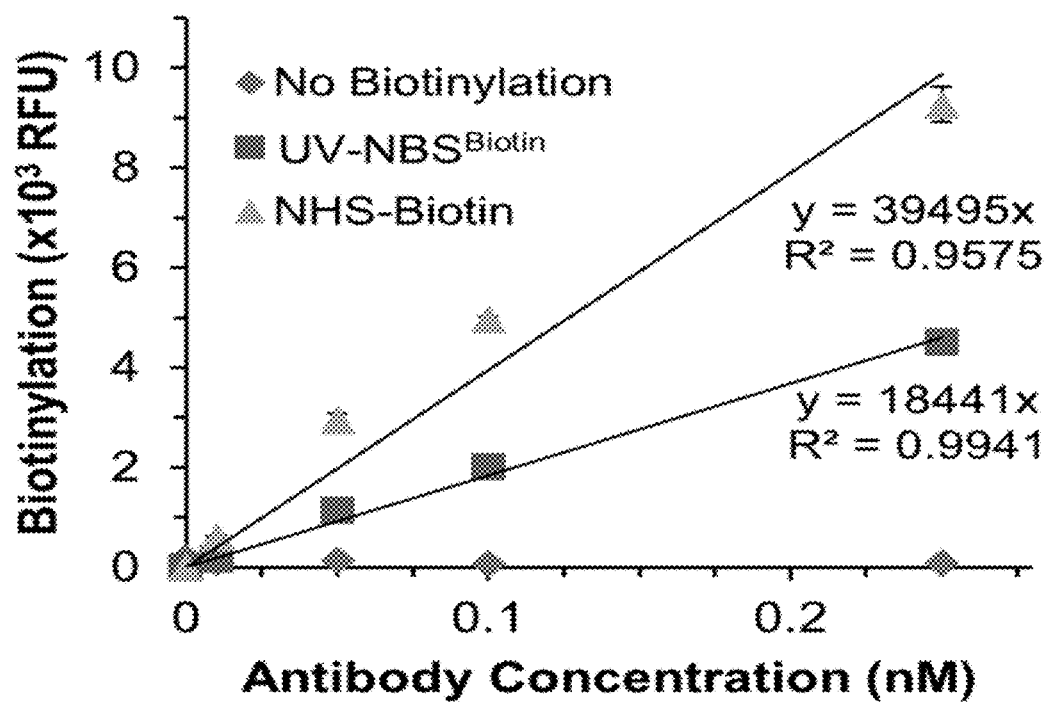
FIG. 47. Determination of the amount of biotinylation using the UV-NBS$^{Biotin}$ method with 1 J/cm$^2$ UV exposure compared to biotinylation using the manufactures recommended protocol for immunoglobulin biotinylation with NHS-Biotin. Biotinylated IgG$^{PSA}$, 0-0.25 nM in 100 μL carbonate bicarbonate coating buffer at pH 9.6, was directly adsorbed to high bind 96-well ELISA plates. Total biotinylation of the surface immobilized immunoglobulin was quantified using streptavidin-HRP. The slope of the linear regression lines were used to determine the relative degree of biotinylation for each method with NHS-Biotin (S=39,495) having 2.14 fold more biotinylation compared to the UV-NBS$^{Biotin}$ (S=18,441). Based on the quantified number of conjugations for the UV-NBS$^{Biotin}$ method of 1.23 conjugations per immunoglobulin (FIG. 3A) the average number of conjugations with NHS-Biotin was determined to be 2.63 biotins per IgG$^{PSA}$. Data represents means (±SD) of triplicate experiments.

Immunoglobulin Immobilization Efficiency. Having determined the optimal UV biotinylation conditions for IgG$^{PSA}$ we then compared the UV-NBS$^{Biotin}$ site-specific immobilization method to three other commonly employed immunoglobulin immobilization techniques: NHS-Biotin, lysine side chain immobilization (ε-NH$_3^+$), and physical adsorption. Utilizing the NHS-Biotin procedure provided by the manufacturer IgG$^{PSA}$ was biotinylated with an average of 2.63 biotins per immunoglobulin, as determined by comparison of the UV-NBS$^{Biotin}$ biotinylated IgG$^{PSA}$ at 1 J/cm$^2$ UV energy to the NHS-Biotinylated IgG$^{PSA}$ via an ELISA assay (FIG. 47). The NHS-Biotin, ε-NH$_3^+$ and physical adsorption immobilization techniques result in highly disordered immunoglobulin immobilization through biotinylation or surface conjugation at random lysine side chains or weak non-specific hydrophobic surface interactions. We compared these three commonly used non-site-specific immobilization techniques to the UV-NBS$^{Biotin}$ method for immunoglobulin immobilization efficiency, antigen detection sensitivity of the functionalized surface, LOD and dynamic antigen detection range.

Figure 43:
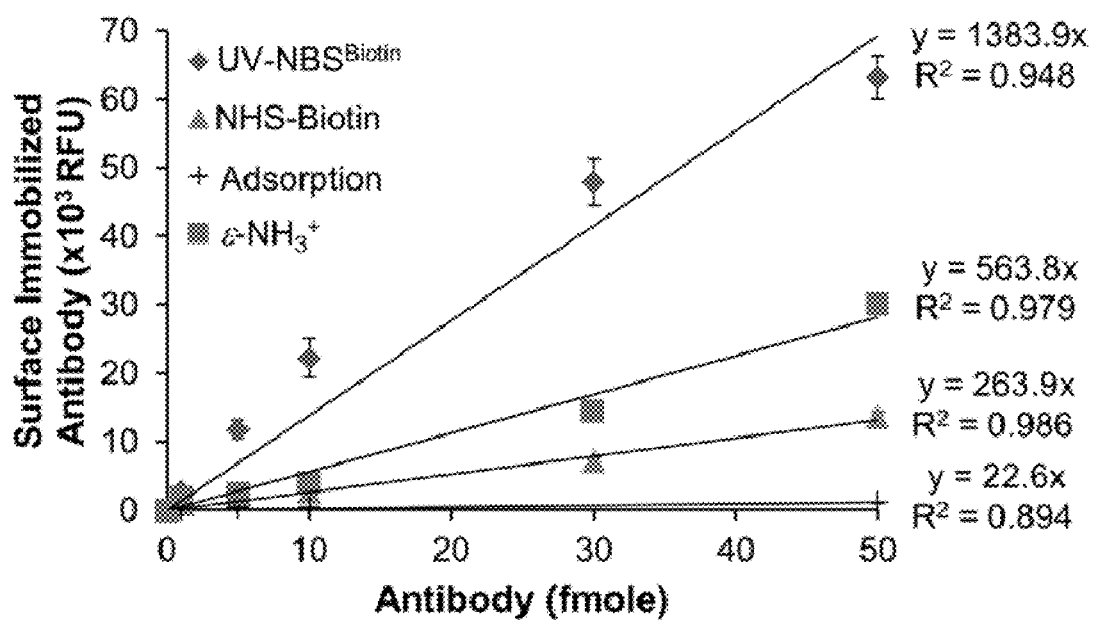
FIG. 43. Immunoglobulin immobilization efficiency of the UV-NBS$^{Biotin}$ method in comparison to NHS-Biotin, ε-NH$_3^+$ and physical adsorption methods using IgG$^{PSA}$/PSA (immunoglobulin/antigen) system. 96-well plates were functionalized with IgG$^{PSA}$ using all four methods. Total surface immobilized immunoglobulin was quantified using an HRP linked anti-Fc secondary immunoglobulin. X-axis shows the starting amount of immunoglobulin used to generate the surface, 0-50 fmole (0-0.5 nM).
Figure 44:
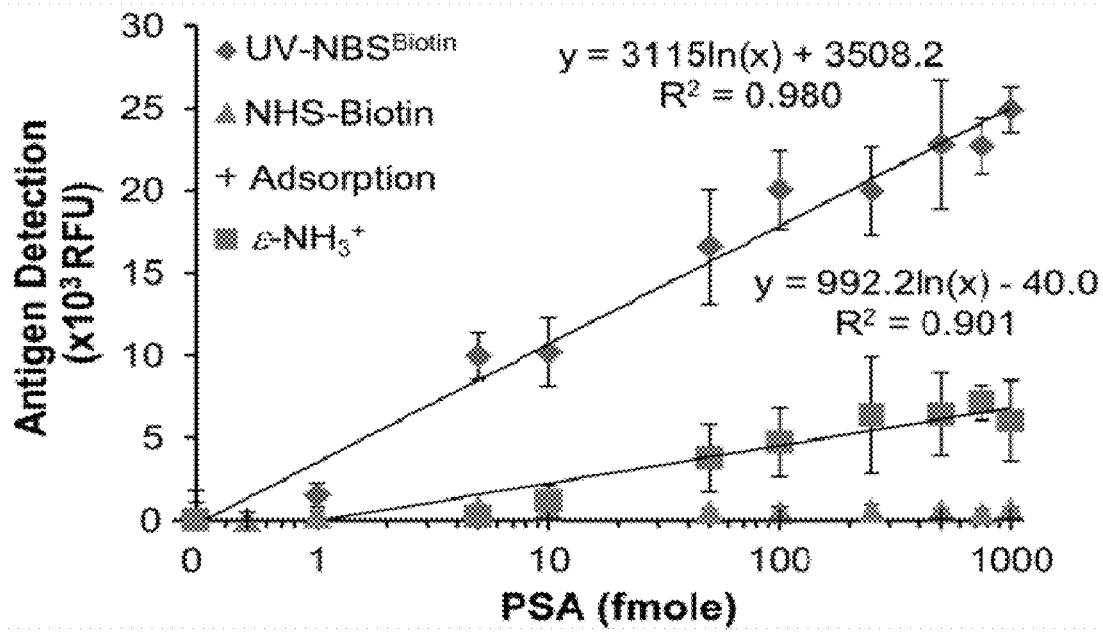
FIG. 44. Antigen detection intensities of the UV-NBS$^{Biotin}$ method in comparison to NHS-Biotin, ε-NH$_3^+$ and physical adsorption methods using IgG$^{PSA}$/PSA (immunoglobulin/antigen) system. 96-well plates were functionalized with IgG$^{PSA}$ (5 fmole, 0.05 nM) using all four methods. Antigen detection sensitivity was determined using increasing concentrations of PSA, 0-1,000 fmole (0-10 nM) as the antigen, det-IgG$^{PSA}$ and quantified by an HRP linked anti-Fc immunoglobulin as the reporter. Data represents means (±SD) of triplicate experiments.

96-well plates were functionalized using the four respective methods with initial immunoglobulin amounts ranging from 0 to 50 fmole (0-0.5 nM) of IgG$^{PSA}$ to generate the immunoglobulin coated surfaces. The amount of surface immobilized immunoglobulin was then determined by binding of an HRP conjugated Fc-specific secondary immunoglobulin to the immobilized IgG$^{PSA}$ capture immunoglobulin. The immobilization efficiency of IgG$^{PSA}$, determined by the slope of the immunoglobulin immobilization curve, using the UV-NBS$^{Biotin}$ method demonstrated a 2.45, 5.24, and 61.12 fold enhancement in immunoglobulin immobilization when compared to the ε-NH$_3^+$, NHS-Biotin and physical adsorption methods, respectively (FIG. 43). These results demonstrate that the UV-NBS$^{Biotin}$ method provides an effective immunoglobulin immobilization technique to generate the highest level of immunoglobulin functionalized surfaces.

6. Determination of Antigen Detection Capabilities and Assay Sensitivity.

Figure 5:
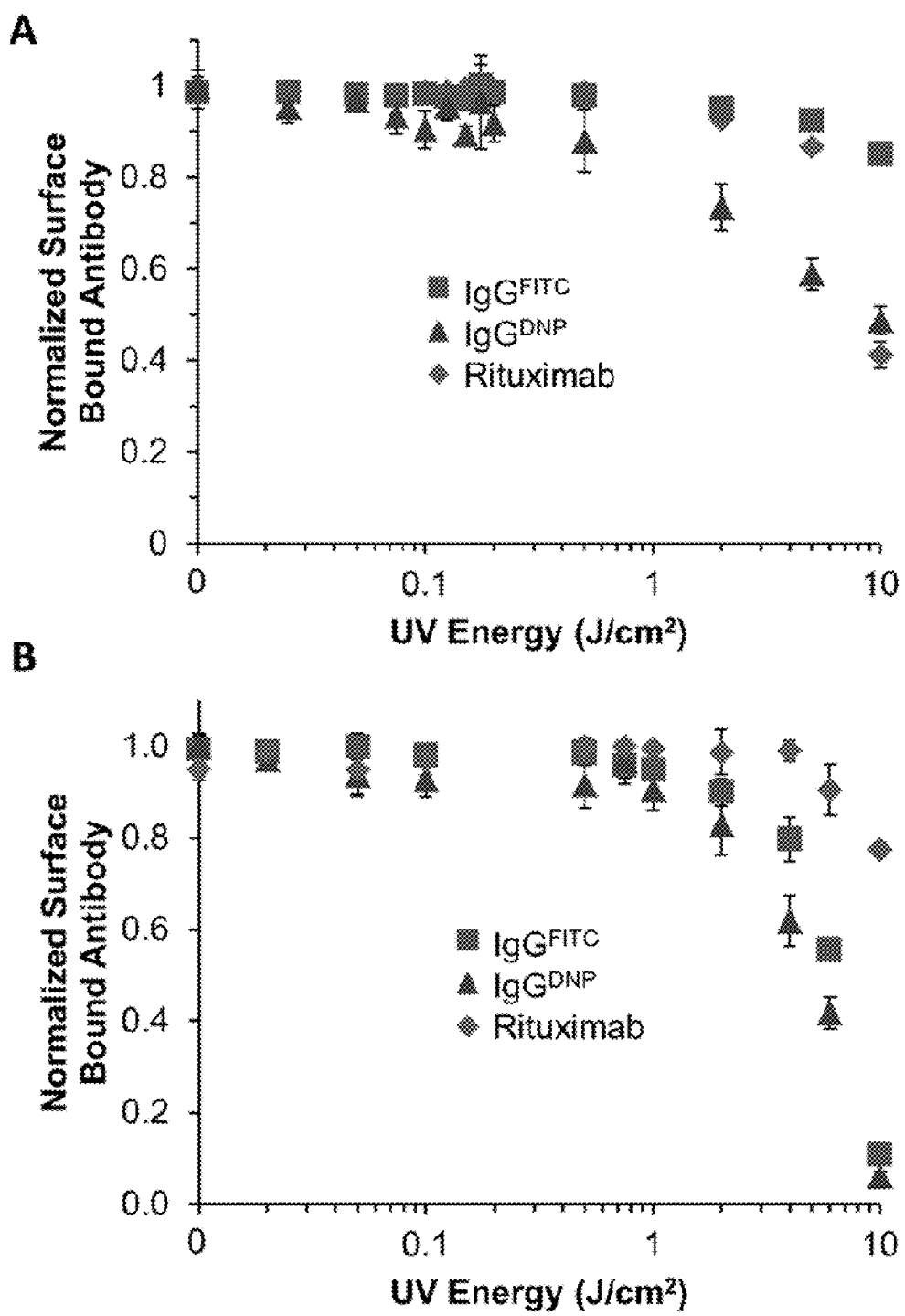
FIG. 5. A) The effects of UV energy exposure on immunoglobulin binding activity combined with Fc recognition were determined by an ELISA assay. UV exposed immunoglobulin (Rituximab, IgG$^{DNP}$, IgG$^{FITC}$) was allowed to bind to its surface immobilized antigen and the total amount of immobilized immunoglobulin was detected using an Fc-specific, HRP conjugated immunoglobulin. B) The effects of UV energy exposure on Fc recognition was determined by directly adsorbing the UV exposed immunoglobulins to a high binding ELISA plate surface and quantified by an Fc-specific, HRP conjugated secondary immunoglobulin. All data represents means (±SD) of triplicate experiments.
Figure 48:
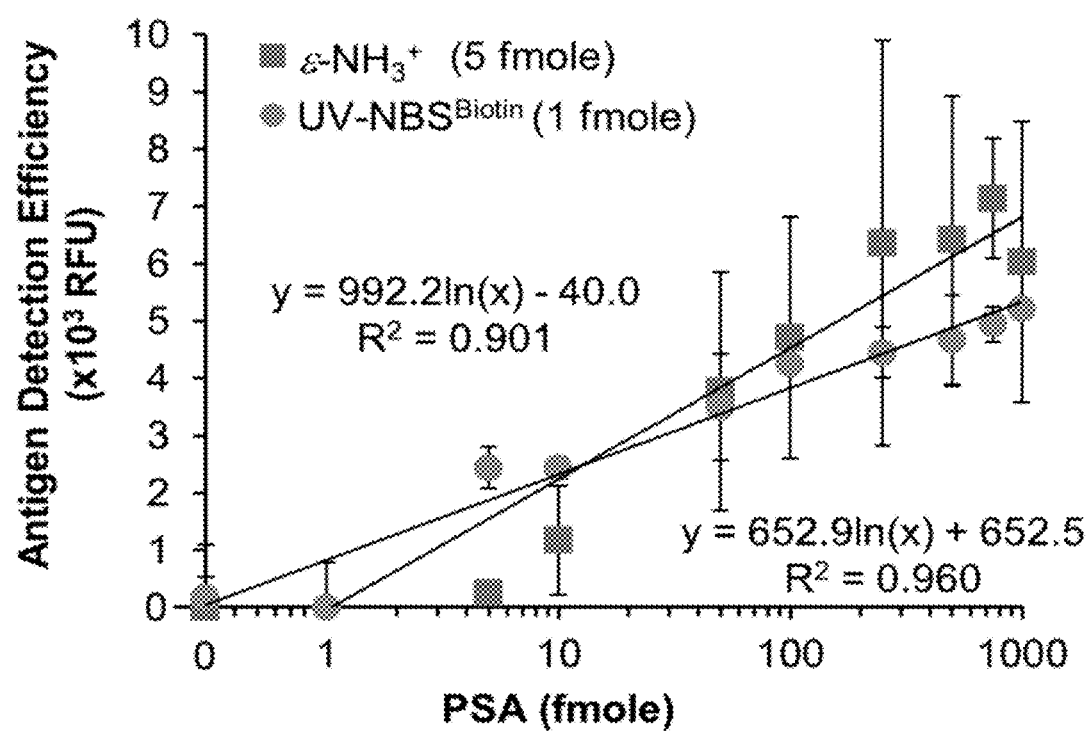
FIG. 48. Comparison of antigen detection efficiency for the UV-NBS$^{Biotin}$ method with 1 mole (0.01 nM) of IgG$^{PSA}$ initial capture immunoglobulin to the ε-NH$_3^+$ immobilization method with 5 fmole (0.05 nM) of IgG$^{PSA}$ initial capture immunoglobulin. Antigen detection efficiency was determined using increasing concentrations of PSA 0-1,000 fmole (0-10 nM) as the antigen, a secondary PSA detection immunoglobulin and an HRP linked anti-Fc immunoglobulin as the reporter. Data represents means (±SD) of triplicate experiments.

Antigen detection and assay sensitivity for the immunoglobulin coated surfaces from each of the immobilization methods was also assessed. Assay sensitivity (S) is typically determined by the slope of the linear regression line obtained by plotting detection signal versus antigen concentration. The assay sensitivity was calculated and compared for all four immobilization techniques using 5 fmole (0.05 nM) of initial IgG$^{PSA}$ as the capture immunoglobulin, free PSA as antigen, det-IgG$^{PSA}$ and an Fc-specific HRP conjugated immunoglobulin as the reporter. A fluorescent HRP substrate was employed to determine the antigen-response curve of a range of standard antigen concentrations from 0 to 1,000 mole (0-10 nM). These PSA antigen levels were below the limit of detection for the physical adsorption, and NHS-Biotin immobilization methods. The UV-NBS$^{Biotin}$ immobilization method displayed the highest antigen detection intensities with the highest assay sensitivity (S=3,115.0, R$^2$=0.980) and the ε-NH$_3^+$ immobilization method demonstrated significantly lower antigen detection intensities with a lower sensitivity (S=992.2, R$^2$=0.901) (FIG. 5). From another perspective, surfaces generated using only 1 fmole (0.01 nM) of immunoglobulin via the UV-NBS$^{Biotin}$ method delivered comparable antigen detection sensitivity (S=652.9, R$^2$=0.960) when compared to surfaces generated using 5 fold more immunoglobulin via the ε-NH$_3^+$ method (FIG. 48). No antigen detection was observed with 1 fmole (0.01 nM) of starting immunoglobulin utilizing the ε-NH$_3^+$ immobilization method. The difference in assay sensitivity can best be explained by the enhanced binding efficiency of the UV-NBS$^{Biotin}$ surface, resulting from improved immobilization of active immunoglobulin. Combined, these results demonstrate that surfaces generated by the UV-NBS$^{Biotin}$ method produced a 3.14 fold higher sensitivity in antigen detection than the ε-NH$_3^+$ method.

7. Determination of the Limit of Detection (LOD) and Dynamic Antigen Detection Range.

The exceptional immunoglobulin immobilization efficiency achieved with the UV-NBS$^{Biotin}$ method provided enhanced sensitivity and a significant improvement to the limit of detection of PSA (3SD to the mean of the zero standard) compared to the $\varepsilon$-$NH_3^+$ immobilization method. The LOD for the UV-NBS$^{Biotin}$ method at starting immunoglobulin amounts of 1 and 5 fmole (0.01 and 0.05 nM) were comparable at 1.97 and 1.88 fmole of PSA (~0.02 nM), respectively. These LOD values signify a 15.63 fold reduction in the LOD of PSA when compared to the $\varepsilon$-$NH_3^+$ LOD of 29.36 fmole (0.29 nM) with 5 fmole (0.05 nM) of initial IgG$^{PSA}$. The UV-NBS$^{Biotin}$ immobilization technique also demonstrated a 4.52 fold broader dynamic detection range for PSA, 1.88-1,000 fmole (0.019-10 nM), compared to the $\varepsilon$-$NH_3^+$ detection range of 29.36-250 fmole (0.29-2.5 nM).

Conclusions.

By site-specifically conjugating a biotin to the NBS of IgG$^{PSA}$ prior to immobilization (UV-NBS$^{Biotin}$ method) the low immunoglobulin immobilization efficiency associated with the previously described UV-NBS method was overcome by ensuring an average of ~1 biotin conjugation per immunoglobulin while still maintaining the highest level of immunoglobulin activity. Surfaces functionalized by the UV-NBS$^{Biotin}$ method displayed significantly enhanced immunoglobulin immobilization efficiency, heightened antigen detection sensitivity, reduced LOD, and improved dynamic antigen detection range resulting in an overall increase in assay sensitivity compared to other commonly used immunoglobulin immobilization methods. Due to the limited detection area on the ever shrinking medical diagnostic devices it is critical that every immunoglobulin immobilized on the detection surface is capable of binding its intended antigen. With high crosslinking efficiencies, the UV-NBS$^{Biotin}$ method provides for a site-specific covalent conjugation method that does not impact antigen or Fc binding interactions. By site-specifically conjugating a biotin molecule to immunoglobulins, oriented immobilization can be carried out on any surface that bears streptavidin, regardless of antigen specificity. Taken together, the UV-NBS$^{Biotin}$ method provides a universal, site-specific immobilization method that is amenable to any available assay detection modality with potential significant implications in the development of miniaturized medical diagnostics and lab on a chip technologies.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method of site specific photo crosslinking of an orthogonally reactive functional group to an immunoglobulin, the method comprising:
   a) providing an immunoglobulin, the immunoglobulin having a conserved nucleotide binding site located away from the antigen binding site of the Fv domain of the immunoglobulin; and
   b) providing a hetero-bifunctional crosslinker having at least a first functional group and at least a second functional group where the first functional group is a heterocyclic photo reactive functional group and the second functional group is a thiol functional group;
   c) mixing the immunoglobulin with the hetero-bifunctional crosslinker to provide a mixture;
   d) exposing the mixture to ultra-violet light so that the first functional group is covalently coupled within the nucleotide binding site of the immunoglobulin; and
   e) reacting the thiol functional group with a thiol reactive functionalized ligand comprising a maleimide moiety or a sulfide moiety such that the thiol functional group is covalently coupled to the maleimide moiety or the sulfide moiety;
   thereby providing a functionalized immunoglobulin having site specific thiolation.

2. The method of claim 1 wherein the heterocyclic photo reactive functional group is an indole compound.

3. The method of claim 1 wherein the heterocyclic photo reactive functional group is indole-3-butyric acid.

4. The method of claim 1 wherein the thiol functional group is a cysteine residue.

5. The method of claim 1 wherein after step e, the thiol reactive functionalized ligand is coupled to a functionalized ligand coated surface in an orientation specific manner whereby the antigen binding sites are oriented away from the surface and available for antigen binding such that the immunoglobulin retains about 90% to about 100% antigen binding activity.

6. The method of claim 5 wherein the functionalized ligand coated surface is the surface of a nanoparticle, a bead, a microfluidic device, an ELISA plate, or a microarray device.

7. The method of claim 5 wherein the functionalized ligand coated surface is a drug delivery system.

8. The method of claim 7 wherein the drug delivery system comprises a liposome, a micelle, a nanoparticle, a quantum dot, or a dendrimer.

9. The method of claim 1 wherein the functionalized ligand is a labeling molecule, an affinity tag, a chemotherapeutic, a cytotoxic agent, an active peptide, a contrast agent, a radiolabel, DNA, or a small molecule inhibitor.

10. The method of claim 9 wherein the active peptide is selected from the group consisting of cell internalization sequences, receptor targeting sequences, and mimotopes.

11. The method of claim 9 wherein the labeling molecule has fluorescent, absorbent, contrast, or radiolabel function.

12. The method of claim 9 wherein the affinity tag is biotin, wherein the biotin is bound to streptavidin, where the streptavidin at least partially coats a surface.

13. The method of claim 12 wherein the surface is the surface of a nanoparticle, a bead, a microfluidic device, an ELISA plate, or a microarray device.

14. A method of site specific photo crosslinking of an orthogonally reactive functional group to an immunoglobulin, the method comprising:
   a) providing an immunoglobulin, the immunoglobulin having a conserved nucleotide binding site located away from the antigen binding site of the Fv domain of the immunoglobulin; and
   b) mixing a hetero-bifunctional crosslinker having at least a first functional group and at least a second functional group wherein the first functional group comprises an indole-3-butyric acid moiety and the second functional group is a thiol functional group;
   c) exposing the mixture to ultra-violet light so that the first functional group is covalently coupled within the nucleotide binding site of the immunoglobulin; and d) after step c, reacting the thiol functional group with a thiol reactive functionalized ligand, wherein the thiol reactive functionalized ligand comprises a maleimide moiety or a sulfide moiety, such that the thiol functional group is conjugated to the maleimide moiety or the sulfide moiety; and after step d, binding the thiol reactive functionalized ligand to a functional ligand coated surface such that the thiol reactive functional ligand is coupled to the functionalized ligand coated surface in an orientation specific manner whereby the antigen binding sites are oriented away from the surface and available for antigen binding such that the immunoglobulin retains about 90% to about 100% antigen binding activity;

thereby providing a functionalized immunoglobulin having site specific thiolation.

15. The method of claim 1 wherein a concentration of the hetero-bifunctional photo-reactive crosslinker in the mixture is 100 μM to 1,600 μM.

16. The method of claim 15 wherein the concentration of the hetero-bifunctional photo-reactive crosslinker in the mixture is 100 μM to 400 μM.

17. The method of claim 1 wherein the immunoglobulin and the hetero-bifunctional photo-reactive crosslinker is present in the mixture in a ratio of about 1:10 to about 1:80.

18. The method of claim 1 wherein the immunoglobulin fragment comprises a Fab fragment, a F(ab') fragment, a F(ab')2 fragment, a Fv fragment, a scFv fragment, a Fd fragment, or a Fc fragment.

19. The method of claim 1 wherein step d is performed after step c, and step e is performed after step d.

* * * * *